US012416013B2

(12) United States Patent
Gao et al.

(10) Patent No.: US 12,416,013 B2
(45) Date of Patent: Sep. 16, 2025

(54) METHOD FOR IMPROVING PLANT GENETIC TRANSFORMATION AND GENE EDITING EFFICIENCY

(71) Applicants: Institute of Genetics and Developmental Biology, Chinese Academy of Sciences, Beijing (CN); Tianjin Genovo Biotechnology Co., Ltd., Tianjin (CN)

(72) Inventors: Caixia Gao, Beijing (CN); Yanpeng Wang, Beijing (CN); Fengti Qiu, Beijing (CN); Yidong Ran, Tianjin (CN); Hu Xu, Tianjin (CN); Kang Zhang, Tianjin (CN)

(73) Assignees: Institute of Genetics and Developmental Biology, Chinese Academy of Sciences, Beijing (CN); Tianjin Genovo Biotechnology Co., Ltd., Tianjin (CN)

( * ) Notice: Subject to any disclaimer, the term of this patent is extended or adjusted under 35 U.S.C. 154(b) by 0 days.

(21) Appl. No.: 17/912,786

(22) PCT Filed: Mar. 19, 2021

(86) PCT No.: PCT/CN2021/081829
§ 371 (c)(1),
(2) Date: Jun. 5, 2023

(87) PCT Pub. No.: WO2021/185358
PCT Pub. Date: Sep. 23, 2021

(65) Prior Publication Data
US 2024/0018535 A1    Jan. 18, 2024

(30) Foreign Application Priority Data

Mar. 19, 2020 (CN) .......................... 202010194837.X
Sep. 4, 2020 (CN) .......................... 202010925874.3

(51) Int. Cl.
*C12N 15/82* (2006.01)
*C12N 5/04* (2006.01)

(52) U.S. Cl.
CPC .......... *C12N 15/8262* (2013.01); *C12N 5/04* (2013.01); *C12N 2310/20* (2017.05); *C12N 2310/3519* (2013.01)

(58) Field of Classification Search
None
See application file for complete search history.

(56) References Cited

U.S. PATENT DOCUMENTS 9,890,388 B2    2/2018   Palatnik et al.

FOREIGN PATENT DOCUMENTS

| CN | 104093844 A | * | 10/2014 | .......... C07K 14/415 |
| WO | WO 1997/43427 | | 11/1997 | |
| WO | WO-2005063990 A2 | * | 7/2005 | .......... C07K 14/415 |
| WO | WO-2005075655 A2 | * | 8/2005 | .............. A01H 1/08 |
| WO | WO 2019/177976 | | 9/2019 | |
| WO | WO-2021007284 A2 | * | 1/2021 | .......... C07K 14/415 |

OTHER PUBLICATIONS

Translated version of CN 104093844, dated Oct. 8, 2014, Debernandi J M (Year: 2014).*
Harding, Ellen W., et al. "Expression and maintenance of embryogenic potential is enhanced through constitutive expression of Agamous-Like 15." Plant Physiology 133.2 (2003): 653-663. (Year: 2003).*
Lowe, Keith, et al. "Morphogenic regulators Baby boom and Wuschel improve monocot transformation." The Plant Cell 28.9 (2016): 1998-2015. (Year: 2016).*
Hu, H., Xiong, L. & Yang, Y. Rice SERK1 gene positively regulates somatic embryogenesis of cultured cell and host defense response against fungal infection. Planta 222, 107-117 (2005). https://doi.org/10.1007/s00425-005-1534-4 (Year: 2005).*
Goedhart, Joachim, et al. "Quantitative co-expression of proteins at the single cell level—application to a multimeric FRET sensor." PloS one 6.11 (2011): e27321. (Year: 2011).*
Svitashev, S., Schwartz, C., Lenderts, B. et al. Genome editing in maize directed by CRISPR-Cas9 ribonucleoprotein complexes. Nat Commun 7, 13274 (2016). https://doi.org/10.1038/ncomms13274 (Year: 2016).*
GenBank Accession XP_028236185.1 "growth-regulating factor 7-like isoform X1 [Glycine soja]" dated Mar. 12, 2019 https://www.ncbi.nlm.nih.gov/protein/XP_028236185.1?report=genbank&log$=prottop&blast_rank=2&RID=JMGCUS5W013 (Year: 2019).*
GenBank Accession AQK41203.1 "Putative leucine-rich repeat receptor-like protein kinase family protein [*Zea mays*]" dated Feb. 6, 2017 https://www.ncbi.nlm.nih.gov/protein/AQK41203.1?report=genbank&log$=protalign&blast_rank=1&RID=WBGVKGWK013 (Year: 2017).*
GenBank Accession RZC22383.1 "GRF1-interacting factor 1 isoform A [Glycine soja]" dated Feb. 13, 2019 https://www.ncbi.nlm.nih.gov/protein/RZC22383.1?report=genbank&log$=protalign&blast_rank=2&RID=360H5R70013 (Year: 2019).*
GenBank Accession XP_028236185.1 "growth-regulating factor 7-like isoform X1 [Glycine soja]" dated Mar. 12, 2019 https://www.ncbi.nlm.nih.gov/protein/XP_028236185.1?report=genbank&log$=prottop&blast_rank=2&RID=JMGCUS5W013 (Year: 2019) (Year: 2019).*
GenBank Accession AK330792.1 "Triticum aestivum cDNA, clone: SET5_F03, cultivar: Chinese Spring" dated Jun. 25, 2009 https://www.ncbi.nlm.nih.gov/nucleotide/AK330792.1?report=genbank&log$=nucltop&blast_rank=3&RID=JMGW8AVD013 (Year: 2009).*
Chen et al. CN-108822217-A, SEQ ID No. 16 (Year: 2019).*

(Continued)

*Primary Examiner* — Charles Logsdon
*Assistant Examiner* — Kelsey L Mcwilliams
(74) *Attorney, Agent, or Firm* — Jenkins, Taylor & Hunt, P.A.

(57) ABSTRACT

The present invention provides a method for improving plant genetic transformation and gene editing efficiency. Specifically, the method improves the regeneration efficiency of plant genetic transformation and/or improves the efficiency of plant gene editing by expressing genes that promote plant cell division, especially meristematic cell division.

12 Claims, 11 Drawing Sheets

Specification includes a Sequence Listing.

(56) References Cited

OTHER PUBLICATIONS

International Search Report for PCT International Patent Application Serial No. PCT/CN2021/081829 dated Jun. 23, 2021 (English Translation).

Kim (2019) Biological roles and an evolutionary sketch of the GRF-GIF transcriptional complex in plants. BMB Reports 52(4):227-238.

Méndez-Hernández et al. (2019) Signaling Overview of Plant Somatic Embryogenesis. Frontiers in Plant Science vol. 10, Article 77.

\* cited by examiner

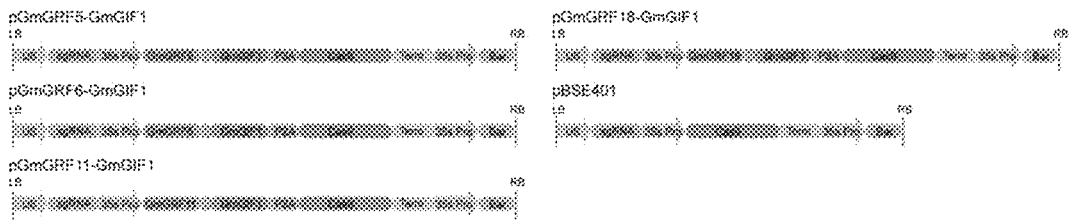
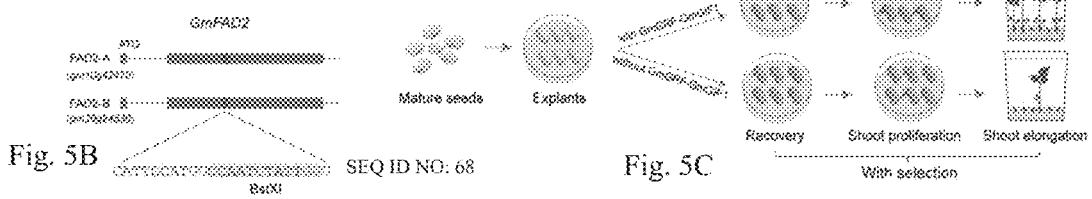
Fig. 5A
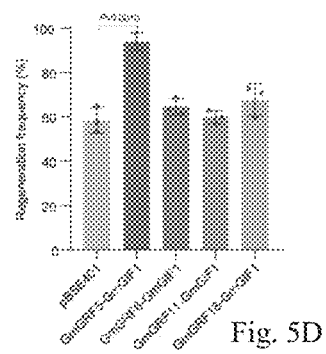
Fig. 5B
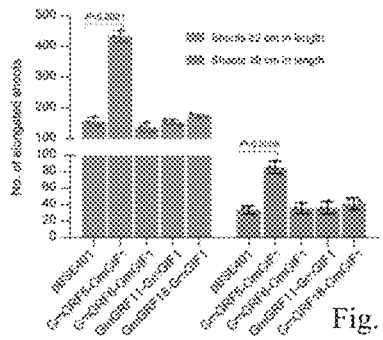
Fig. 5C
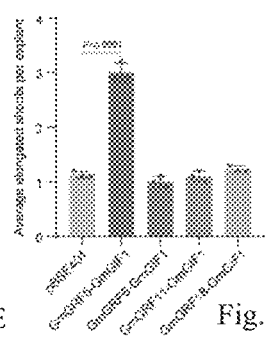
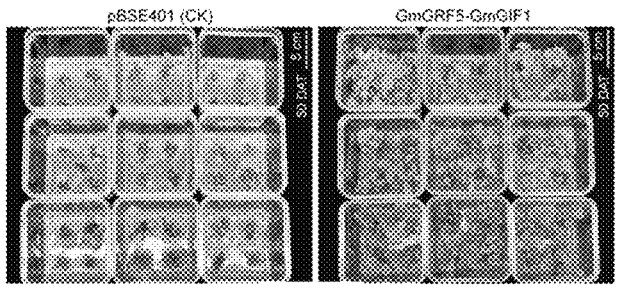
Fig. 5D          Fig. 5E          Fig. 5F
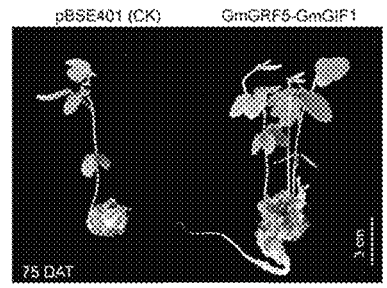
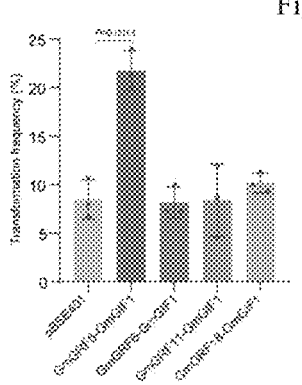
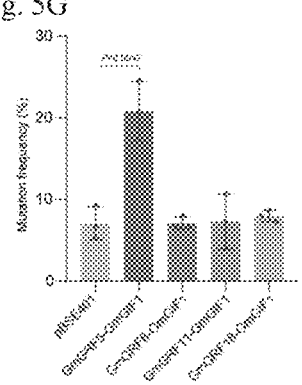
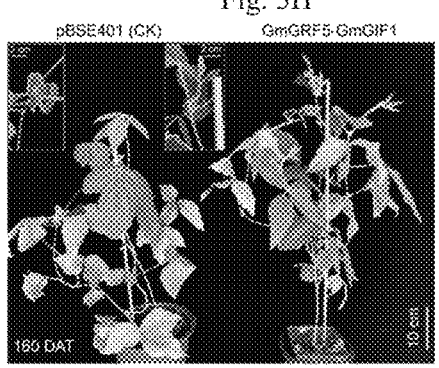
Fig. 5G          Fig. 5H
Fig. 5I          Fig. 5J          Fig. 5K

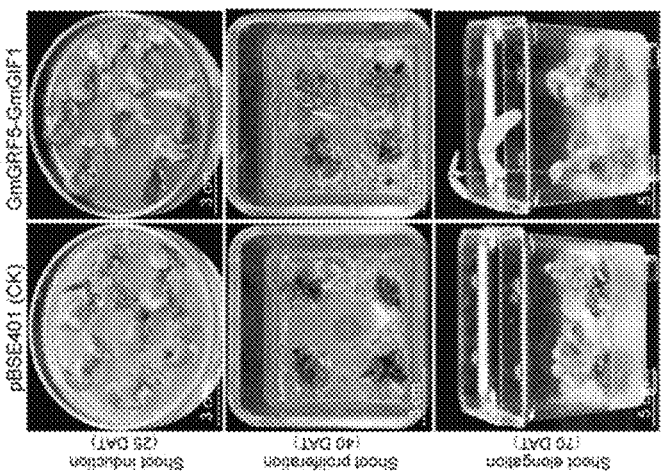
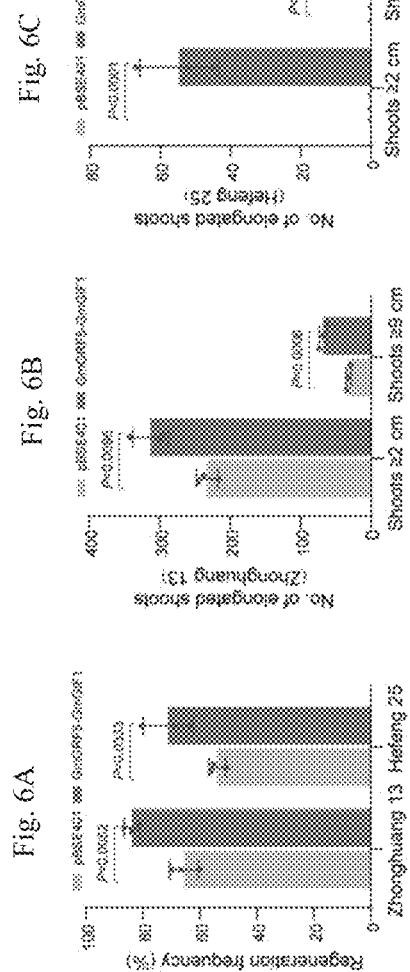
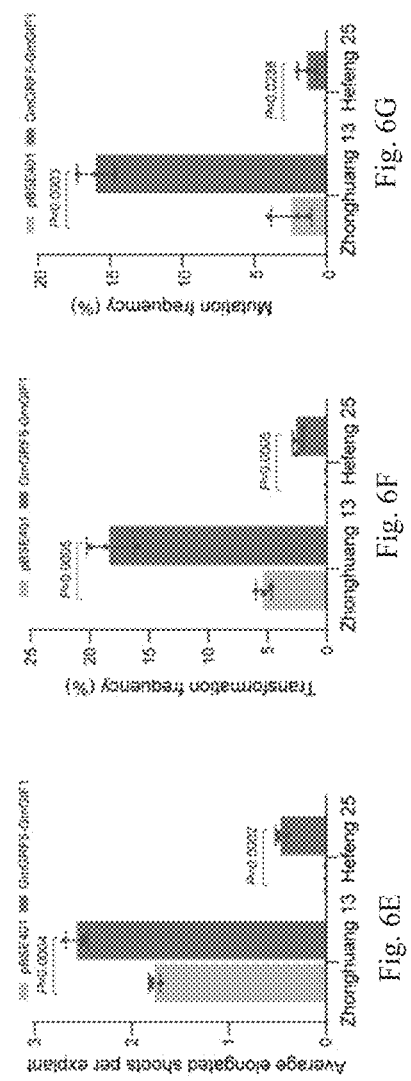
Fig. 6A Fig. 6B Fig. 6C Fig. 6D
Fig. 6E Fig. 6F Fig. 6G

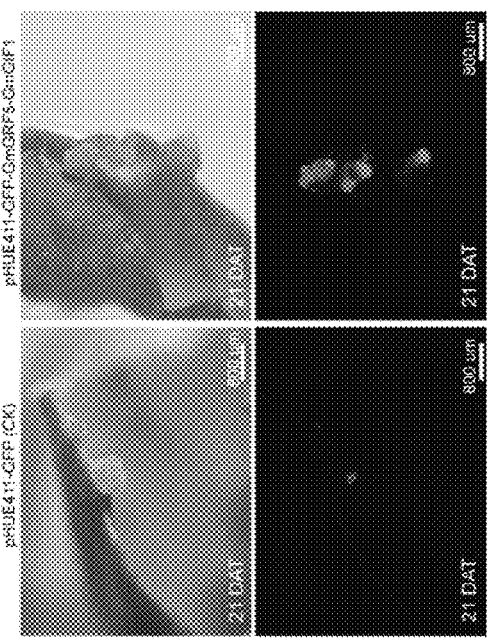
Fig. 7A
Fig. 7B
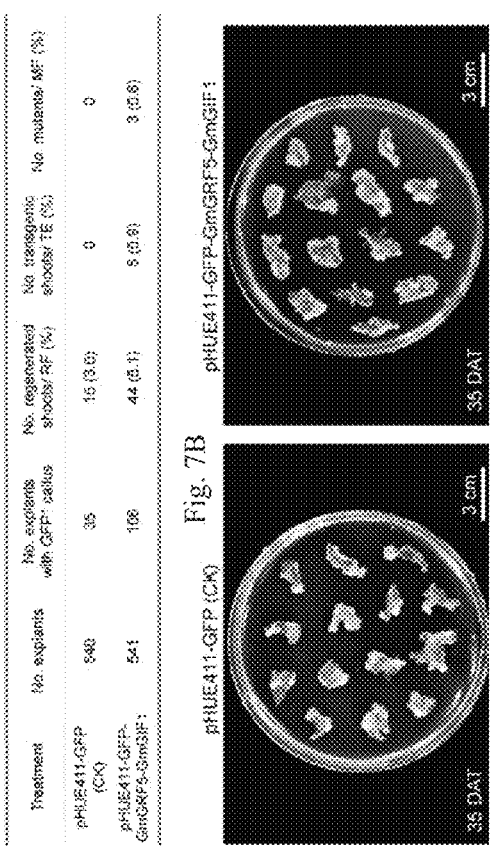
Fig. 7C
Fig. 7D

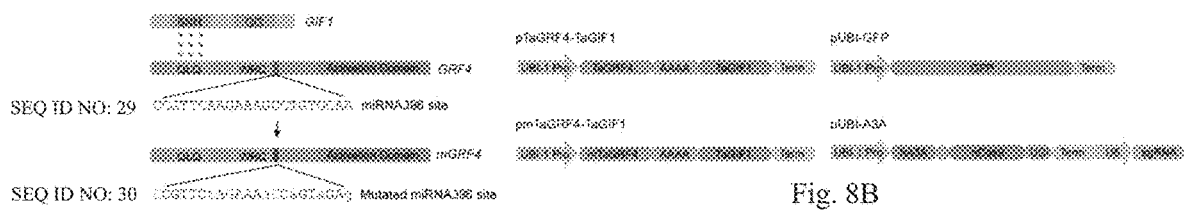
Fig. 8A
Fig. 8B
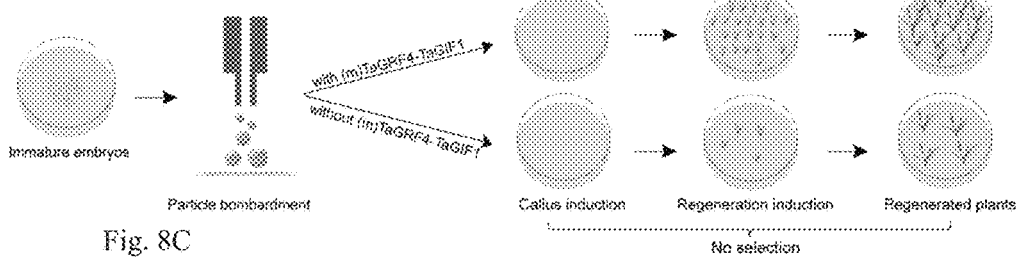
Fig. 8C
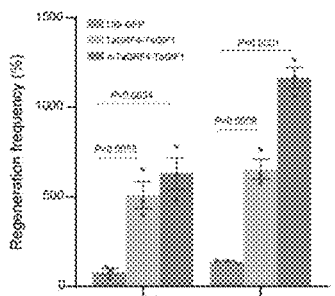
Fig. 8D
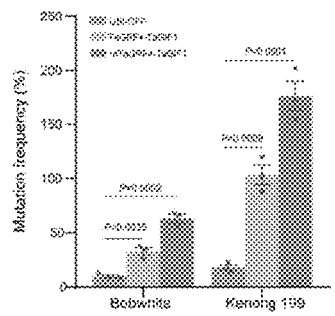
Fig. 8E
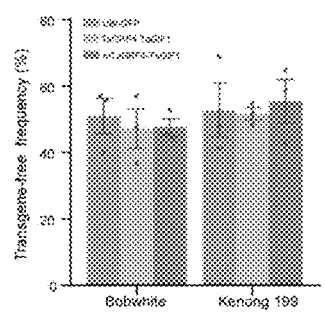
Fig. 8G
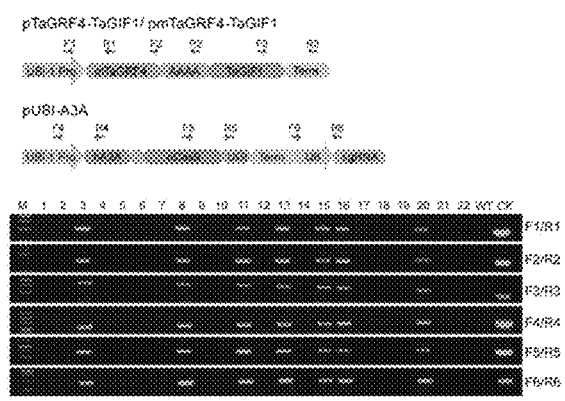
Fig. 8F
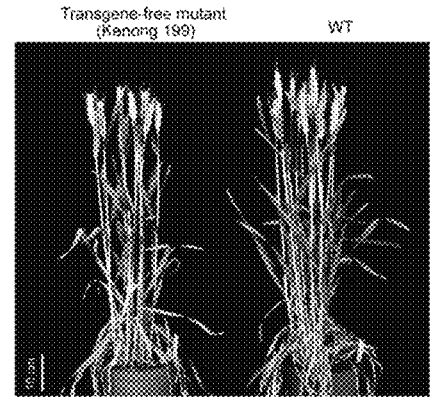
Fig. 8H

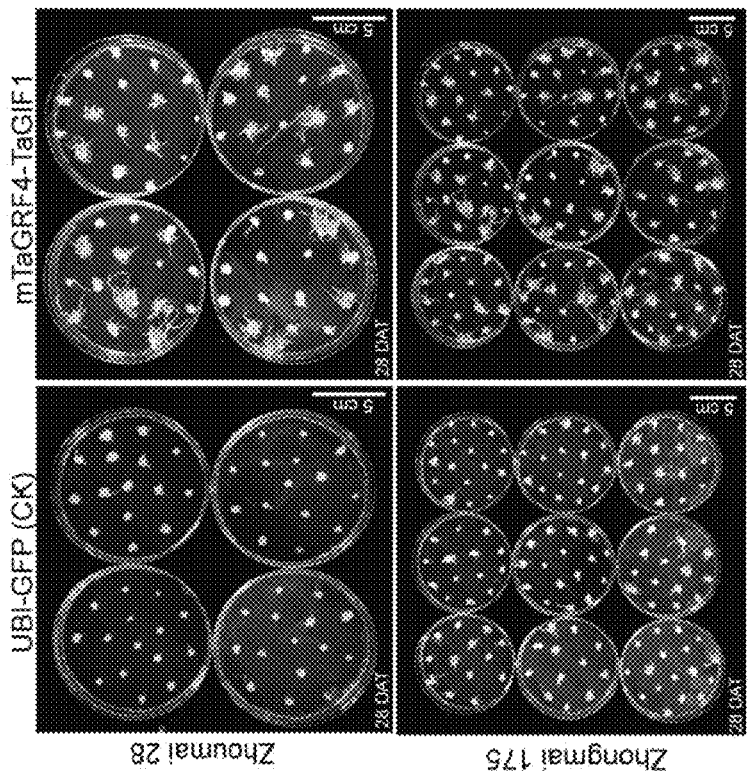
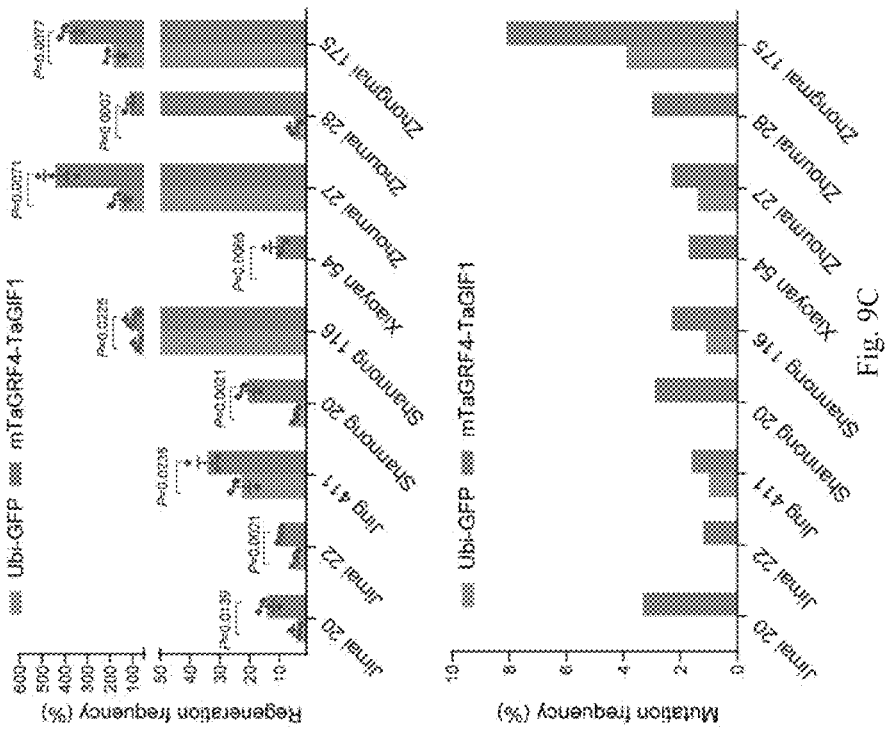

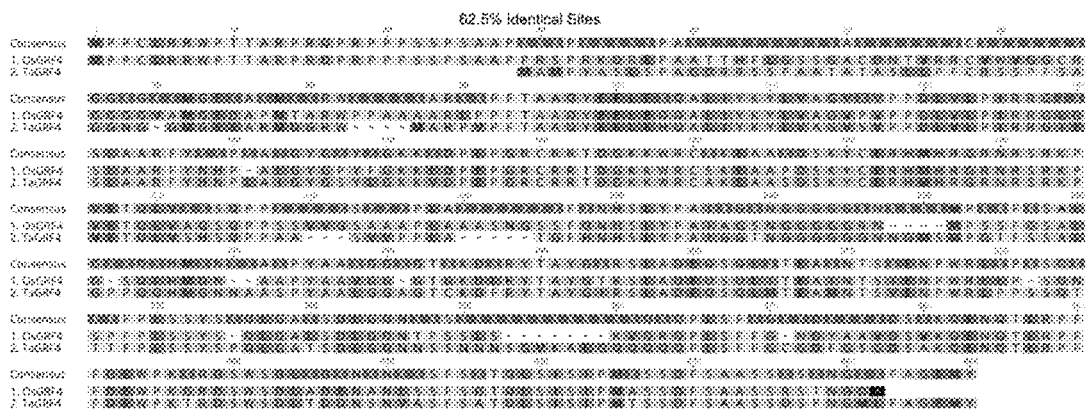
Fig. 12A
Fig. 12B
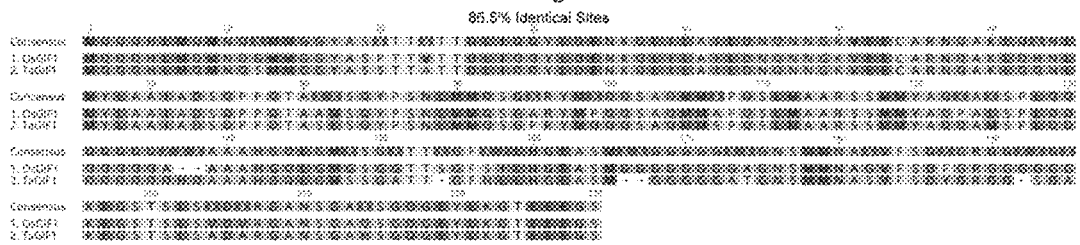
CAGGTCCCCCGCCGCATGATCGG SEQ ID NO: 67
EcoO109I
Fig. 13

METHOD FOR IMPROVING PLANT GENETIC TRANSFORMATION AND GENE EDITING EFFICIENCY

REFERENCE TO SEQUENCE LISTING TEXT FILE

The Sequence Listing text file associated with the instant disclosure has been electronically submitted to the United States Patent and Trademark Office via EFS as a 123.118 byte UTF-8-encoded text file created on Jul. 5, 2023 and entitled "1547_48_PCT_US_ST25.xml". The Sequence Listing submitted via EFS is hereby incorporated by reference in its entirety.

TECHNICAL FIELD

The present invention belongs to the field of plant genetic engineering. Specifically, the present invention relates to a method for improving plant genetic transformation and gene editing efficiency. More specifically, the present invention relates to improving regeneration efficiency of plant genetic transformation and/or improving efficiency of plant gene editing by expression of genes which can promote division of plant cells, especially meristematic cells.

BACKGROUND OF THE INVENTION

Development of crop genetic breeding includes artificial selection breeding, cross breeding, mutation breeding and molecular marker assisted breeding using molecular technology. As the variety genetic diversity is gradually reduced, the bottleneck effect of traditional breeding is more and more obvious: it is difficult to use conventional breeding technology to obtain breakthrough new varieties to meet the requirement of human and sustainable agricultural development. The rapid development of life sciences makes it possible to enter the post-genome era from the "read" phase of the biological genetic information, and the accurate "rewriting" of the genome and the "new design" are becoming reality. This kind of biological technical means designed for creating new trait or living body shows great prospect in the field of disease treatment, medicine, manufacturing, especially agriculture and so on.

Genome editing technology is a revolutionary technical means appearing in the current life science which can realize accurate, efficient and specific rewriting of the genome and has revolutionary pushing effect to the research and exploration of life science. Gene editing refers to deleting, replacing, or inserting operation of the target gene so as to modify the genetic information to obtain a new function or phenotype, even creating a new species. Development of efficient and accurate breeding technology suitable for crops using gene editing technology will break the defect of the traditional breeding, realizing molecular design breeding of precise transformation from the genome. It has important strategic significance for the development of future agriculture.

Current gene editing technology mainly comprises ZFN. TALEN and CRISPR/Cas system. CRISPR/Cas system, due to its high efficiency and flexibility, is currently the simplest and widely used gene editing technology system. In CRISPR/Cas system, Cas protein can target any position in the genome under the guide action of the artificial designed guide RNA (guide RNA). Base editing system is a new gene editing technology developed based on CRISPR system, which can be divided into cytosine base editing system and adenine base editing system, wherein the respectively deaminase and adenine deaminase are fused with Cas9 single-chain nickase. Under the targeting function of the guide RNA, Cas9 single-chain nickase generates a single-stranded DNA region, so the deaminase can efficiently respectively remove amino group of the C and A nucleotide on the single-stranded DNA of the targeting position, resulting in U base and I base, which can be repaired as T base and G base by the repair process of the cell itself. Base editing technology overcomes the defect of traditional DSB-mediated gene editing, which can efficiently realize the precise replacement of a single base. CRISPR/Cas system-mediated robust genetic engineering technology system will provide strong technical support for gene research and new plant molecular design breeding, and will accelerate the cultivation of new variety of crops and realize sustainable development of agriculture.

A key step of plant gene editing is to deliver the gene editing nuclease protein or coding nucleic acid to the plant cell to realize the editing of the target gene. The present plant genome editing delivery technology is mainly realized by genetic transformation and tissue culture technology, mainly comprising *agrobacterium* mediated method and gene gun method. Important progress has been made in plant transformation over the past few years, but transformation of many agronomically important plants (e.g., maize, soybeans, canola, wheat, indica rice, sugar cane and sorghum; and inbred lines) is still difficult and time-consuming. Generally, the only method causing the culture reaction is to optimize the culture medium components and/or explant materials and sources, which results in the success in some gene type, but many important crop plants (including excellent inbred line or variety) do not generate beneficial culture reaction and regeneration technology system. Although the transformation of a pattern genotype may be effective, the process of gradually introgressing the transgene into the product inbred line is laborious, expensive and time-consuming. Especially for monocotyledon wheat, efficiency of current gene gun and *agrobacterium* transformation method is low and greatly limited by the genotype, and a long-term tissue culture process is required. At present, the maximum bottleneck of wheat gene editing is the low efficiency of the current traditional wheat transformation system, the large technical difficulty, limitation by genotype and low throughput.

In order to facilitate the research of plant gene function and molecular design breeding more efficiently utilizing gene editing technology, establishing and digging a method to improve the plant transformation efficiency and shorten the time of tissue culture has important meaning.

SUMMARY OF THE INVENTION

In one aspect, the present invention provides a method for improving plant cell regeneration efficiency in plant transformation, the method comprising:
  (a) introducing into a cell of the plant
    i) an expression construct comprising a coding nucleic acid sequence of WUS, an expression construct comprising a coding nucleic acid sequence of BBM and an expression construct comprising a coding nucleic acid sequence of SERK; and/or
    ii) an expression construct comprising a coding nucleic acid sequence of GRF nd an expression construct comprising a coding nucleic acid sequence of GIF;
  (b) regenerating an intact plant from the plant cell.

In another aspect, the present invention provides a method for improving the transformation efficiency of an exogenous nucleic acid sequence of interest in a plant or for transforming an exogenous nucleic acid sequence of interest into a plant, the method comprising:
 (a) introducing into a cell of the plant
  i) an expression construct comprising a coding nucleic acid sequence of WUS, an expression construct comprising a coding nucleic acid sequence of BBM and an expression construct comprising a coding sequence of SERK; and/or
  ii) an expression construct comprising a coding nucleic acid sequence of GRF nd an expression construct comprising a coding nucleic acid sequence of GIF;
 (b) introducing at least one expression construct comprising at least one exogenous nucleic acid sequence of interest into the plant cell; and
 (c) regenerating an intact plant from the plant cell.

In another aspect, the present invention provides a method for improving gene editing efficiency in a plant or for gene editing in a plant, the method comprising:
 (a) introducing into a plant cell
  i) an expression construct comprising a coding sequence of WUS, an expression construct comprising a coding sequence of BBM and an expression construct comprising a coding sequence of SERK; and/or
  ii) an expression construct comprising a coding sequence of GRF and an expression construct comprising a coding sequence of GIF;
 (b) introducing at least one expression construct comprising at least one exogenous sequence of interest to the plant cell, wherein the at least one exogenous sequence of interest encodes a component of a gene editing system; or introducing at least one component of a gene editing system to the plant cell; and
 (c) regenerating an intact plant from the plant cell.

The invention further provides a kit for carrying out the method of the invention, comprising at least i) an expression construct comprising a coding nucleic acid sequence of WUS, an expression construct comprising a coding nucleic acid sequence of BBM and an expression construct comprising a coding nucleic acid sequence of SERK; and/or ii) an expression construct comprising a coding nucleic acid sequence of GRF and an expression construct comprising a coding nucleic acid sequence of GIF.

The present invention also provides use of i) an expression construct comprising a coding nucleic acid sequence of WUS; an expression construct comprising a coding nucleic acid sequence of BBM and an expression construct comprising a coding nucleic acid sequence of SERK; and/or ii) an expression construct comprising a coding nucleic acid sequence of GRF and an expression construct comprising a coding nucleic acid sequence of GIF, for improving plant cell regeneration efficiency in plant transformation, for improving the transformation efficiency of exogenous nucleic acid sequence of interest in the plant or for improving the gene editing efficiency in the plant.

BRIEF DESCRIPTION OF THE DRAWINGS

FIGS. 5A-5K. The effect of GmGRF-GmGIF1 complexes on regeneration, transformation, and genome editing of the soybean cultivar Williams 82. (FIG. 5A) Schematic representations of T-DNA regions each containing one of the four GmGRF-GmGIF1 complexes. pBSE401 is the CRISPR/Cas9 control construct. (FIG. 5B) Schematic of the GmFAD2 sgRNA target sites in the two subgenomes. (FIG. 5C) The general procedure for Agrobacterium-mediated transformation of soybean. (FIG. 5D) Comparison of the effects of four GmGRF-GmGIF1 complexes on regeneration frequencies of Williams 82. RF (regeneration frequency)= no. of explants with multiple buds/explant number×100%. (FIG. 5E) Numbers of putative glufosinate-resistant elongated shoots ≥2 cm in length (on day 50 after transformation) and shoots ≥9 cm in length (on day 75 after transformation) regenerated from explants transformed with the four GmGRF-GmGIF1 complexes and pBSE401, respectively. (FIG. 5F) Average numbers of elongated shoots regenerated from single explants transformed with the four GmGRF-GmGIF1 complexes and pBSE401, respectively. (FIG. 5G) Regeneration of explants transformed with pGmGRF5-GmGIF1 and pBSE401 and cultured in medium supplemented with 5.0 mg/L glufosinate on day 50 after infection. (FIG. 5H) Typical explants with regenerated shoots cultured in medium supplemented with 5.0 mg/L glufosinate on day 75 after infection with pGmGRF5-GmGIF1 and pBSE401, respectively. (FIG. 5I) Transformation efficiencies of Williams 82 transformed with the four GmGRF-GmGIF1 complexes and pBSE401, respectively. (FIG. 5J) GmFAD2 mutation frequencies with CRISPR/Cas9 treated by four pGmGRF-GmGIF1 constructs and pBSE401, respectively. (FIG. 5K) Performance of mature GmFAD2-edited soybean plants (160 days after transformation) transformed with pGmGRF5-GmGIF1 and pBSE401, respectively. All values and error bars are mean values±s.e.m. of three independent experiments.

FIGS. 6A-6G. The effect of the GmGRF5-GmGIF1 complex on regeneration, transformation, and genome editing of two soybean cultivars Zhonghuang 13 and Hefeng 25. (FIG. 6A) Regeneration frequencies of explants transformed with pGmGRF5-GmGIF1 and pBSE401 on day 50 after transformation. (FIGS. 6B and 6C) Numbers of putative glufosinate-resistant elongated shoots (>2 cm in length) on day 50 after transformation and elongated shoots (>9 cm in length) on day 75 regenerated from explants of Zhonghuang 13 (FIG. 6B) and Hefeng 25 (FIG. 6C) transformed with pGmGRF5-GmGIF1 and pBSE401, respectively. (FIG. 6D) Shoot induction, shoot proliferation and shoot elongation in Hefeng 25 explants transformed with pGmGRF5-GmGIF1 and pBSE401, respectively. (FIG. 6E) Average numbers of elongated shoots regenerated from single explants of Zhonghuang 13 and Hefeng 25 transformed with pGmGRF5-GmGIF1 and pBSE401, respectively. (FIG. 6F) Transformation efficiencies of Zhonghuang 13 and Hefeng 25 transformed with pGmGRF5-GmGIF1 and pBSE401, respectively. (FIG. 6G) GmFAD2 mutation rates in Zhonghuang 13 and Hefeng 25 transformed with pGmGRF5-GmGIF1 and pBSE401, respectively. All values and error bars are mean values±s.e.m. of three independent experiments.

FIG. 7A-7D. The effect of the GmGRF5-GmGIF1 complex on regeneration, transformation, and genome editing efficiencies in strawberry cultivar Benihoppe. (FIG. 7A) Schematic representation of the T-DNA region containing the GmGRF5-GmGIF1 complex. pHUE411-GFP is the CRISPR/Cas9 control construct. (FIG. 7B) Effects of the GmGRF5-GmGIF1 complex on strawberry regeneration, transformation, and genome editing efficiencies. The data were collected on day 35 after explants were transformed with pHUE411-GFP-GmGRF5-GmGIF1 and pHUE411-GFP. RF (regeneration frequency)=no. of regenerated shoots/total explants×100%. TE (transformation efficiency)=no. of transgenic shoots/total explants×100%. MF (mutation frequency)=no. of mutants/total explants× 100%. (FIG. 7C) GFP positive calli from explants transformed with pHUE411-GFP-GmGRF5-GmGIF1 and pHUE411-GFP, on day 21 after transformation. (FIG. 7D) Calli and shoots from explants transformed with pHUE411-GFP-GmGRF5-GmGIF1 and pHUE411-GFP, respectively, on day 35 after transformation.

FIGS. 8A-8H. Comparison of the effects of TaGRF4-TaGIF1 and mTaGRF4-TaGIF1 on regeneration and genome editing in two common wheat cultivars Kenong 199 and Bobwhite. (FIG. 8A) Schematic representation of common wheat GIF1, GRF4, and mutated GRF4. The dotted lines indicate the interaction between the SNH and QLQ domains. mTaGRF4 was created by introducing five point mutations in the miRNA396 target site of common wheat TaGRF4. (FIG. 8B) Schematic representations of constructs pTaGRF4-TaGIF1, pmTaGRF4-TaGIF1, and the base editor, pUBI-A3A. pUBI-GFP is the control construct. (FIG. 8C) General procedure for transgene-free genome editing in common wheat by transient expression of a cytosine base editor. (FIG. 8D) Comparison of the effects of TaGRF4-TaGIF1 and mTaGRF4-TaGIF1 on regeneration frequencies of Bobwhite and Kenong199. RF (regeneration frequency)= no. of regenerated shoots/immature embryos bombarded× 100%. (FIG. 8E) Comparison of the effects of TaGRF4-TaGIF1 and mTaGRF4-TaGIF1 on genome editing frequencies in Bobwhite and Kenong199. MF (mutation frequency)=no. of mutants/immature embryos bombarded× 100%. (FIG. 8F) Primer sets for detecting transgene-free mutants, and the outcome of tests on 22 representative TaALS mutant plants (Kenong 199). (FIG. 8G) The Transgene-free frequencies in Bobwhite and Kenong199 wheat cultivars transformed with TaGRF4-TaGIF1, mTaGRF4-TaGIF1 and pUBI-GFP (control construct), respectively. (FIG. 8H) Transgene-free mutant plants regenerated from Kenong 199 immature embryos transiently-expressing mTaGRF4-TaGIF1 and the cytosine base editor A3A-PBE, do not exhibit abnormal growth. In (FIG. 8D), (FIG. 8E) and (FIG. 8G), values and error bars are means±s.e.m. of three independent experiments.

FIGS. 9A-9C. The effect of transient expression of the mutated TaGRF4-TaGIF1 complex on common wheat regeneration and genome editing efficiencies in nine elite wheat cultivars. (FIG. 9A) The regeneration frequencies of nine elite common wheat cultivars transformed with pmTaGRF4-TaGIF1 and pUBI-GFP (control construct). Values and error bars are means±s.e.m. of three independent experiments. (FIG. 9B) Regenerated plants of Xiaoyan 54 and Zhongmai 175 transformed with mTaGRF4-TaGIF1 and pUBI-GFP (control construct), respectively, 28 days after transformation. (FIG. 9C) The mutation frequencies in the nine elite common wheat cultivars transformed with pmTaGRF4-TaGIF1 and pUBI-GFP (control construct). MF (mutation frequency)=total no. of mutants/total immature embryos bombarded×100%.

(FIG. 10A) Mutations in the GmFAD2 gene from the 15 representative soybean lines identified by PCR-RE assays. Lanes 1 to 15 show digests of the PCR fragments amplified from the transgenic soybean plants using BstXI. Lanes labeled CK show the digests of PCR fragments amplified from a wild-type control plant. (FIG. 10B) The outcome of tests for transgene-free mutants using two primer sets in 15 representative gmfad2 mutant plants. Lanes without a band indicate transgene-free mutants. Lanes labeled CK are the PCR fragments amplified from a WT plant. (FIG. 10C). Sanger sequencing of the GmFAD2 gene in wild type and the edited gmfad2 mutants.

(FIG. 11A) Clustal W was used to align 31 GRFs, including nine FveGRFs and 22 GmGRFs. MEGA 7.0 was used to construct a neighbor-joining phylogenetic tree with 1000 bootstrap replications. (FIG. 11B) Schematic of the sgRNA designed to target the FaPL gene. (FIG. 11C) Detection of mutations by Sanger sequencing in regenerated strawberry lines transformed with pHUE411-GFP-GmGRF5-GmGIF1.

FIGS. 12A and 12B. Multiple sequence alignment of the deduced GRF4 and GIF1 proteins, which are the most similar between common wheat and rice. (FIG. 12A) The GRF4 from common wheat shows 62.5% conservation with the GRF4 from rice at the amino acid level. (FIG. 12B) The GIF1 from common wheat shows 86.5% conservation with the GIF1 from rice at the amino acid level. Sequences were compared using Geneious Prime.

FIG. 13. Schematic of the TaALS sgRNA target sites in the common wheat genome. SgRNA target sites within a conserved region of common wheat TaALS homeologs were targeted by the base editing systems. The EcoO109I restriction enzyme site in the sgRNA target sequence was used for mutation detection.

DETAILED DESCRIPTION OF THE INVENTION

I. Definitions

Figure 1:
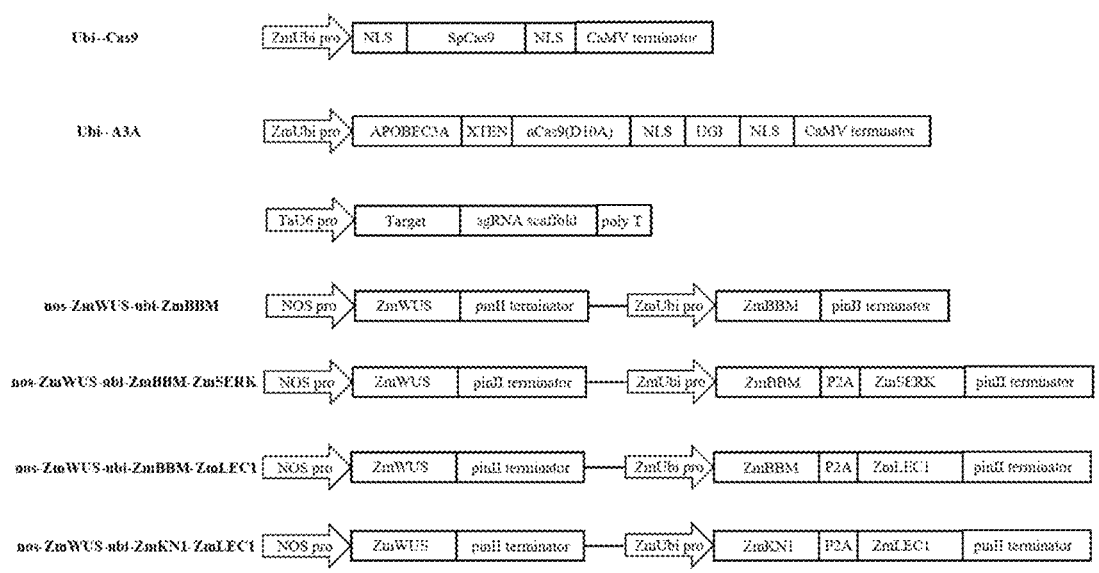
FIG. 1. Expression constructs for detecting the influence of a plurality of DR combinations on genetic transformation and gene editing efficiency.

In the present invention, unless otherwise specified, the scientific and technical terms used herein have the meaning commonly understood by those skilled in the art, and the protein and nucleic acid chemistry used herein, molecular biology, cell and tissue culture, microbiology, immunology related term and laboratory operation steps are widely used in the corresponding field and conventional steps. For example, the standard recombinant DNA and molecular cloning techniques used in the present invention are well known to those of skill in the art, and are more fully described in the following literature: Sambrook. J., Fritsch. E. F. and Maniatis, T., Molecular Cloning: A Laboratory Manual; Cold Spring Harbor Laboratory Press: Cold Spring Harbor, 1989 (hereinafter "Sambrook"). At the same time, for a better understanding of the present invention, the definitions and explanations of the related terms are provided below.

As used herein, the term "and/or" encompasses all combinations of items connected by the term, and each combination should be regarded as individually listed herein. For example. "A and/or B" covers "A", "A and B", and "B". For example, "A, B, and/or C" covers "A", "B", "C", "A and B", "A and C", "B and C", and "A and B and C".

When the term "comprise" is used herein to describe the sequence of a protein or nucleic acid, the protein or nucleic acid may consist of the sequence, or may have additional amino acids or nucleotide at one or both ends of the protein or nucleic acid, but still have the activity described in this invention. In addition, those skilled in the art know that the methionine encoded by the start codon at the N-terminus of the polypeptide will be retained under certain practical conditions (for example, when expressed in a specific expression system), but does not substantially affect the function of the polypeptide. Therefore, when describing the amino acid sequence of specific polypeptide in the specification and claims of the present application, although it may not include the methionine encoded by the start codon at the N-terminus, the sequence containing the methionine is also encompassed, correspondingly, its coding nucleotide sequence may also contain a start codon; vice versa.

"Genome" as used herein encompasses not only chromosomal DNA present in the nucleus, but also organelle DNA present in the subcellular components (e.g., mitochondria, plastids) of the cell.

The term "exogenous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively). "C" for cytidylate or deoxycytidylate, "G" for guanylate or deoxyguanylate, "U" for uridylate. "T" for deoxythymidylate, "R" for purines (A or G). "Y" for pyrimidines (C or T), "K" for G or T. "H" for A or C or T. "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

As used herein, an "expression construct" refers to a vector suitable for expression of a nucleotide sequence of interest in an organism, such as a recombinant vector. "Expression" refers to the production of a functional product. For example, the expression of a nucleotide sequence may refer to transcription of the nucleotide sequence (such as transcribe to produce an mRNA or a functional RNA) and/or translation of RNA into a protein precursor or a mature protein.

"Expression construct" of the invention may be a linear nucleic acid fragment (including a DNA or RNA fragment), a circular plasmid, a viral vector.

The "expression construct" of the present invention may comprise a regulatory sequence and a nucleic acid sequence of interest operably linked thereto. The regulatory sequence and the nucleic acid sequence of interest may be of different sources, or are of the same origin but are arranged in a manner different from that normally found in nature.

"Regulatory sequence" and "regulatory element" are used interchangeably and refer to a nucleotide sequence which is located upstream (5' non-coding sequences), within, or downstream (3' non-coding sequences) of a coding sequence, and influence the transcription, RNA processing or stability, or translation of the associated coding sequence. The regulatory sequence may include, but is not limited to, a promoter, a translation leader sequence, an intron and a polyadenylation recognition sequence. "Promoter" refers to a nucleic acid fragment capable of controlling transcription of another nucleic acid fragment. In some embodiments of the invention, the promoter is a promoter capable of controlling gene transcription in a cell regardless of whether it is derived from the cell. The promoter may be a constitutive promoter or a tissue specific promoter or a developmentally regulated promoter or an inducible promoter.

As used herein, the term "operably linked" refers to a regulatory element (e.g., but not limited to, a promoter sequence, a transcription termination sequence, etc.) and a nucleic acid sequence (e.g., a coding sequence or open reading frame), are linked such that transcription of the nucleotide sequence is controlled and regulated by the transcription regulatory element. Techniques for operably linking a regulatory element region to a nucleic acid molecule are known in the art.

"Introducing" a nucleic acid molecule (e.g., an expression construct) into a plant cell refers to that the nucleic acid molecule is presented to the plant cell such that the nucleic acid molecule enter the interior of the plant cell.

"Regeneration" refers to the process of growing an intact plant from one or more plant cells (e.g., plant protoplasts, callus or explants).

II. Improved Plant Transformation

In one aspect, the present invention provides a method for improving plant cell regeneration efficiency in plant transformation, the method comprising:
(a) introducing into a cell of the plant
  i) an expression construct comprising a coding nucleic acid sequence of WUS, an expression construct comprising a coding nucleic acid sequence of BBM and an expression construct comprising a coding nucleic acid sequence of SERK; and/or
  ii) an expression construct comprising a coding nucleic acid sequence of GRF and an expression construct comprising a coding nucleic acid sequence of GIF;
(b) regenerating an intact plant from the plant cell.

In another aspect, the present invention provides a method for improving transformation efficiency of an exogenous nucleic acid sequence of interest in a plant or for transforming an exogenous nucleic acid sequence into a plant, the method comprising:
(a) introducing into a cell of the plant
  i) an expression construct comprising a coding nucleic acid sequence of WUS, an expression construct comprising a coding nucleic acid sequence of BBM and an expression construct comprising a coding sequence of SERK; and/or
  ii) an expression construct comprising a coding nucleic acid sequence of GRF and an expression construct comprising a coding nucleic acid sequence of GIF;
(b) introducing at least one expression construct comprising at least one exogenous nucleic acid sequence of interest to the plant cell; and
(c) regenerating an intact plant from the plant cell.

In some embodiments of this aspect, step (a) and step (b) are carried out at the same time. In some embodiments of this aspect, step (a) is performed prior to step (b). In some embodiments of this aspect, step (b) is performed prior to step (a). In some embodiments of this aspect, step (c) is performed after step (a) and step (b).

In another aspect, the present invention provides a method for improving gene editing efficiency in a plant or for gene editing in a plant, the method comprising:
(a) introducing into a cell of the plant
  i) an expression construct comprising a coding sequence of WUS, an expression construct comprising a coding sequence of BBM and an expression construct comprising a coding sequence of SERK; and/or
  ii) an expression construct comprising a coding sequence of GRF and an expression construct comprising a coding sequence of GIF;
(b) introducing at least one expression construct comprising at least one exogenous sequence of interest to the plant cell, wherein the at least one exogenous sequence of interest encodes a component of a gene editing system; or introducing at least one component of the gene editing system to the plant cell; and
(c) regenerating an intact plant from the plant cell.

In some embodiments of this aspect, step (a) and step (b) are carried out at the same time. In some embodiments of this aspect, step (a) is performed prior to step (b). In some embodiments of this aspect, step (b) is performed prior to step (a). In some embodiments of this aspect, step (c) is performed after step (a) and step (b).

The invention further provides a kit for carrying out the method of the invention, comprising at least i) an expression construct comprising a coding nucleic acid sequence of WUS, an expression construct comprising a coding nucleic acid sequence of BBM and an expression construct comprising a coding nucleic acid sequence of SERK; and/or ii) an expression construct comprising a coding sequence of GRF and an expression construct comprising a coding sequence of GIF.

The present invention also provides use of i) an expression construct comprising a coding nucleic acid sequence of WUS; an expression construct comprising a coding nucleic acid sequence of BBM and an expression construct comprising a coding nucleic acid sequence of SERK; and/or ii) an expression construct comprising a coding nucleic acid sequence of GRF and an expression construct comprising a coding nucleic acid sequence of GIF, for improving plant cell regeneration efficiency in plant transformation, for improving the transformation efficiency of exogenous nucleic acid sequence of interest in the plant or for improving the gene editing efficiency in the plant.

WUS (WUSCHEL), BBM (BABY BOOM) and SERK (Somatic Allogenesis receptor-like kinase) are conservative development regulatory factors (DR) widely present in plants. The inventors have surprisingly found that co-expression of the combination of WUS. BBM and SERK in the plant cell can significantly improve the efficiency of the plant cell to regenerate into intact plants, and significantly improve transformation efficiency of an exogenous nucleic acid sequence of interest into the plant. When the exogenous nucleic acid sequence of interest encodes a gene editing system, the gene editing efficiency can be significantly improved.

Examples of WUS, BBM and SERK suitable for use in the present invention include, but are not limited to, WUS, BBM, and SERK from *Arabidopsis*, canola, strawberry, potato, rice, tomato, soybean, corn or wheat.

In some embodiments of various aspects of the invention. WUS is corn WUS (ZmWUS), BBM is the corn BBM (ZmBBM), or SERK is corn SERK (ZmSERK). In some embodiments, the ZmWUS comprises the amino acid sequence shown in SEQ ID NO: 1. In some embodiments, the ZmBBM comprises the amino acid sequence shown in SEQ ID NO: 2. In some embodiments, the ZmSERK comprises the amino acid sequence shown in SEQ ID NO: 3.

In some embodiments of various aspects of the present invention, at least two or at least three or all of the coding nucleic acid sequence of WUS, the coding nucleic acid sequence of BBM, the coding nucleic acid sequence of SERK, and the at least one exogenous nucleic acid sequence of interest are placed in a same expression construct. In some embodiments, the coding nucleic acid sequence of WUS, the coding nucleic acid sequence of BBM, the coding nucleic acid sequence of SERK and the at least one exogenous nucleic acid sequence of interest are respectively placed in different expression constructs.

In some embodiments of various aspects of the invention, the coding nucleic acid sequence of WUS, the coding nucleic acid sequence of BBM, and the coding nucleic acid sequence of SERK are placed in the same expression construct, while the at least one exogenous nucleic acid sequence of interest is placed in another expression construct.

In some embodiments of various aspects of the present invention, the coding nucleic acid sequence of WUS, the coding nucleic acid sequence of BBM, the coding nucleic acid sequence of SERK and/or the at least one exogenous nucleic acid sequence of interest are operatively connected to transcription regulatory elements.

Methods of expressing different proteins by the same expression construct are known in the art. For example, the different proteins can be placed in the same expression construct under the control of different transcriptional regulatory elements (e.g., different promoters). Alternatively, different proteins can be fused by self-cleaving peptide (e.g., 2A peptide, including but not limited to P2A, E2A; F2A and T2A, etc.), then expressed under the control of the same transcriptional control element (e.g., different promoter), so that separate different proteins can be generated by self-cleavage of the self-cleaving peptide after translation or translation. Alternatively, an internal ribosome entry site (IRES) can be inserted between the coding nucleic acid sequences of different proteins.

GRFs (Growth Factors) are specific transcription factors in plants, mainly controlling plant cell size, chloroplast proliferation, stamen development, osmotic stress and other plant growth and development processes. GRF transcription factors are widely existed in the plant, mainly comprising two conserved domains: QLQ and WRC. The QLQ domain of GRFs can interact with the SNH domain (SYT N-terminal domain) in GIF (GRF-interacting factor) proteins, so as to exercise transcriptional activation function. WRC domain comprises 1 functional nuclear localization signal and 1 DNA binding motif, plays a role in DNA binding. Generally, QLQ and WRC domain are located at the N terminal of the GRFs. However, some GRFs also have a second WRC domain at the C terminal.

"GIF" (GRF-interacting factor) is a protein that can form transcription co-activation factor complexes with GRF. GIFs are homologous to human transcription co-activation factor synovial sarcoma transport protein (synovial translocation protein. SYT). In *Arabidopsis thaliana*, GIF plays a role in cell proliferation during blade development and maintains proliferation ability of the meristematic cells during flower organ development.

The inventors have further surprisingly found that co-expression of the combination of GRF and GIF in plant cell can significantly improve the regenerating efficiency of a plant cell into intact plant, and significantly improve the transformation efficiency of exogenous nucleic acid sequence of interest into the plant. When the exogenous nucleic acid sequence of interest encodes a gene editing system, the gene editing efficiency can be significantly improved.

Examples of GRFs suitable for use in the present invention include, but are not limited to, GRF from *Arabidopsis*, canola, potato, rice, tomato, soybean, corn or wheat. Examples of GIF suitable for use in the present invention include, but are not limited to, GIF from *Arabidopsis*, canola, potato, rice, tomato, soybean, corn or wheat. However, as long as it can form transcription co-activating factor complex, GRF and GIF in the present invention does not necessarily have the same origin.

In some embodiments of the invention, the GRF is wheat GRF. Suitable wheat GRFs include, but are not limited to, wheat GRF4. In some embodiments, the wheat GRF4 comprises the amino acid sequence of SEQ ID NO: 4.

In some embodiments of the invention, the GIF is wheat GIF. Suitable wheat GIFs include, but are not limited to, wheat GIF1. In some embodiments, the wheat GIF1 comprises the amino acid sequence shown in SEQ ID NO: 6.

In some embodiments of the invention, the GRF is soybean GRF. Suitable soybean GRF include, but are not limited to, soybean GRF5, soybean GRF6, soybean GRF11, or soybean GRF11. In some embodiments, the soybean GRF5 comprises the amino acid sequence of SEQ ID NO: 7. In some embodiments, the soybean GRF6 comprises the amino acid sequence of SEQ ID NO: 8. In some embodiments, the soybean GRF11 comprises the amino acid sequence of SEQ ID NO: 9. In some embodiments, the soybean GRF18 comprises the amino acid sequence of SEQ ID NO: 10.

In some embodiments of the invention, the GIF is derived from soybean GIF. Suitable soybean GIFs include, but are not limited to, soybean GIF1. In some embodiments, the soybean GIF1 comprises the amino acid sequence shown in SEQ ID NO: 11.

Many of the transcription factors in the plant including GRF are regulated by miRNAs. For example, GRF4 is negatively controlled by miR396. The invention surprisingly found that mutating the miRNA binding site in GRF can significantly improve the effect of the GRF/GIF combination in improving efficiency of plant cell regeneration and plant genetic transformation.

Therefore, in some embodiments of the present invention, the GRF comprises a mutated miRNA binding site, so as not to be regulated by the miRNA. Examples of the miRNAs include, but are not limited to, miR396, depending on the particular GRF. In some embodiments, the GRF with the mutated miRNA binding site comprises the amino acid sequence of SEQ ID NO: 5.

In some embodiments of the present invention, at least two or all of the coding sequence of the GRF, the coding sequence of the GIF and the at least one exogenous nucleic acid sequence of interest are placed in a same expression construct.

In some embodiments of the present invention, the coding sequence of the GRF and the coding sequence of GIF are placed in a same expression construct, while the at least one exogenous nucleic acid sequence of interest is placed in another expression construct.

In some embodiments of the present invention, the coding sequence of the GRF, the coding sequence of the GIF and the at least one exogenous nucleic acid sequence are operatively linked to transcription control sequences.

In some embodiments of the invention, the GRF is fused to the GIF. In some embodiments, the GRF is fused to the N terminal of the GIF. In some embodiments, the GRF is fused to the GIF through a linker. An exemplary linker comprises the sequence AAAA (SEQ ID NO: 12) or SGGS (SEQ ID NO: 13). Preferably, the linker is AAAA.

In some embodiments of the present invention, "an expression construct comprising a coding nucleic acid sequence of GRF and an expression construct comprising a coding nucleic acid sequence of GIF" encompasses an expression construct comprising a coding sequence of the fusion protein of GRF and GIF.

In some embodiments of the present invention, the fusion protein of the GRF and GIF comprises the amino acid sequence encoded by any one of SEQ ID NO: 17-22. In some embodiments of the present invention, the fusion protein of the GRF and GIF is encoded by any one of SEQ ID NO: 17-22. In some embodiments of the present invention, the fusion protein of GRF and GIF comprises the amino acid sequence encoded by any one of SEQ ID NO: 23-28.

The "at least one exogenous nucleic acid sequence of interest" may be any nucleic acid sequence to be transformed into the plant. For example, the exogenous nucleic acid sequence of interest can encode an agronomic trait, insect resistance, disease resistance, herbicide resistance, sterility, grain characteristics, and a trait important for the commercial product. The nucleic acid sequence of interest may also include those nucleic acid sequences involved in oil, starch, carbohydrate or nutrient metabolism, and those nucleic acid sequences affecting seed size, sucrose content, and the like.

In some preferred embodiments of the present invention, the at least one exogenous nucleic acid sequence encodes a component of a gene editing system, so as to carry out gene editing in the plant.

"Gene editing", also known as genome editing, uses a sequence-specific nuclease or a derivative thereof for nucleotide insertion, deletion or substitution in the genome of an organism. Gene editing generally results in site-specific double-strand break (DSB) at the desired position in the genome, and then introducing desired DNA insertion, deletion or substitution by the process of repairing DSB. However, gene editing can also cover base editing technology, transcriptional activation or inhibition, epigenetic modification technology, which does not relate to DSB, as long as it has sequence specificity.

The gene editing system used is not particularly limited in the present invention. For example, a gene editing system suitable for use in the present invention includes but is not limited to zinc finger nuclease (ZFN), meganuclease (MGN); transcription activating factor-like effector nuclease (TALEN) and CRISPR (Clustered regularly interspaced short palindromic repeats) system. "Zinc finger nucleases" are artificial restriction enzymes prepared by fusing a zinc finger DNA binding domain to a DNA cleavage domain. The zinc finger DNA binding domain of a single ZFN typically contains 3-6 individual zinc finger repeats, each of which can identify a sequence of, for example, 3 bp. By combining different zinc finger repeating sequences, different genome sequences can be targeted.

Meganucleases generally refer to homing endonucleases capable of identifying a nucleic acid sequence of 14-40 base in length. Long recognition sequence allows the meganucleases to have strong specificity so as to reduce the off-target effect.

"Transcription activator-like effector nucleases" are restriction enzymes that can be engineered to cleave specific DNA sequences, and that are typically prepared by fusing the DNA-binding domain of a transcription activator-like effector (TALE) to a DNA cleavage domain. TALE can be engineered to bind almost any desired DNA sequence.

"CRISPR system" generally comprises two components capable of forming complexes with sequence specificity: CRISPR nuclease or a variant thereof, and a corresponding guide RNA. Therefore, for the CRISPR system, the at least one exogenous nucleic acid sequence of interest of the invention can comprise a nucleic acid sequence encoding a CRISPR nuclease or a variant thereof, and/or a coding nucleic acid sequence of a corresponding guide RNA. Alternatively, at least one component of the gene editing system introduced into the plant cell may include a CRISPR nuclease or a variant thereof, and/or a corresponding guide RNA.

In some preferred embodiments of the present invention, the gene editing system is a CRISPR system. A large number of different CRISPR gene editing systems are known in the art, which can be applied to the invention. For example, suitable CRISPR gene editing system can be found at the Addgene company website (Addgene, Watertown, Massachusetts). CRISPR gene editing systems cover the systems capable of changing genomic sequence, but also comprise the systems for transcription control but not changing the genomic sequence.

As used herein, the term "CRISPR nuclease" generally refers to a nuclease present in the naturally occurring CRISPR system. The CRISPR nuclease variant comprises a modified form of natural CRISPR nuclease, artificial mutant (including the nickase mutant), catalytic active fragment, or a fusion with other functional protein/polypeptide and so on. A variety of artificial functional variants of CRISPR nuclease are known in the art, such as high specific variant or nickase variant, or a cytidine deaminase or adenosine deaminase fusion protein and so on. CRISPR nuclease or a variant thereof can interact with the corresponding guide RNA for recognizing, binding and/or cutting target nucleic acid structure. Those skilled in the art know how to select a suitable CRISPR nuclease or a variant thereof to achieve the purpose of the present invention.

CRISPR nuclease or a variant thereof used in the CRISPR gene editing system of the invention can be selected from Cas3, Cas8a, Cas5, Cas8b, Cas8c. Cas10d, Cse1, Cse2. Csy1, Csy2, Csy3; GSU0054, Cas10, Csm2, Cmr5, Cas10, Csx11, Csx10, Csf1, Cas9, Csn2, Cas4, Cpf1 (Cas12a), C2c1, C2c3 or C2c2 protein, or functional variants of these nucleases.

In some embodiments of the present invention, the CRISPR nuclease or a variant thereof comprises a Cas9 nuclease or a variant thereof. CRISPR gene editing system based on Cas9 nuclease or variant thereof is also referred to herein as CRISPR-Cas9 gene editing system. The Cas9 nuclease can be a Cas9 nuclease from different species, such as spCas9 (having an amino acid sequence of SEQ ID NO: 15) from *Streptococcus pyogenes* (*S. pyogenes*).

Cas9 nuclease variant can include Cas9 nickase (nCas9), wherein one of two sub-domain (HNH nucleic acid enzyme sub-domain and RuvC sub-domain) of the Cas9 nuclease DNA cutting domain is inactivated to form a nickase. In some embodiments, combination of a Cas9 nickase and two gRNAs targeting upstream and downstream of the sequence to be edited can be used to realize deletion of the sequence to be edited, or to realize the replacement of the sequence to be edited in the presence of a donor sequence.

In some embodiments of the present invention, the CRISPR nuclease or variant thereof may also comprises Cpf1 (Cas12a) nuclease or a variant thereof such as a high specific variant. The Cpf1 nuclease can be Cpf1 nuclease from different species, such as from *Francisella novicida* U112; Acidaminococcus sp.BV3L6 and Lachnospiraceae bacterium ND2006. CRISPR gene editing system based on Cpf1 nuclease or variant thereof is also referred to herein as CRISPR-Cpf1 system.

In some embodiments of the present invention, the CRISPR nuclease variant further comprises a base editor. The base editor is typically a fusion protein comprising a deaminase and a CRISPR nuclease variant lack of DNA cleavage activity.

As used in the present invention, the CRISPR nuclease variant lack of DNA cleavage activity comprises but not limited to Cas9 nickase (nCas9), nuclease-dead Cas9 nuclease (dCas9) or nuclease-dead Cpf1 nuclease (dCpf1). Nuclease-dead Cas9 nuclease (dCas9) or nuclease-dead Cpf1 nuclease (dCpf1) completely lacks DNA cutting activity. A plurality of CRISPR nuclease variants lack of DNA cleavage activity are known in the art.

As used in the present invention. "deaminase" refers to an enzyme that catalyzes the deamination reaction. In some embodiments of the present invention, the deaminase is s cytosine deaminase, which is capable of receiving single-stranded DNA as a substrate and capable of catalyzing cytidine or deoxycytidine respectively deaminated as uracil or deoxyuracil. In some embodiments of the present invention, the deaminase is adenosine deaminase, which is capable of receiving single-stranded DNA as a substrate and capable of catalyzing adenosine or deoxyadenosine (A) to form inosine (I). A variety of suitable cytosine deaminases or adenine deaminases with single-stranded DNA as substrate are known in the art. Suitable cytosine deaminases include, but are not limited to, APOBEC1 deaminase, activation-induced cytidine deaminase (AID), APOBEC3G, CDA1, human APOBEC3A deaminase. In some preferred embodiments, the cytosine deaminase is human APOBEC3A. Examples of suitable adenine deaminases include, but are not limited to, the DNA-dependent adenine deaminase disclosed by Nicloe M. Gaudelli et al. (doi: 10.1038/nature24644, 2017).

By using a fusion of a CRISPR nuclease variant lack of DNA cleavage activity and a deaminase (forming a so-called "base editor"), base editing in the target nucleotide sequence, such as conversion from C to T or conversion from A to G, can be achieved. A variety of base editors are known in the art, and those skilled in the art will know how to select a suitable base editor to achieve the object of the present invention. The base editor-based CRISPR gene editing system is also referred to as a base editing system.

In some preferred embodiments of the present invention, the CRISPR system is a base editing system. Preferably, the base editing system comprises a base editor having the amino acid sequence shown in SEQ ID NO: 14.

As used herein. "guide RNA" and "gRNA" can be interchangeably used, which refers to a RNA molecule that can form a complex with the CRISPR nuclease or its functional variant and is capable of targeting the complex to a target sequence because it has a certain identity to the target sequence. The guide RNA targets the target sequence through base paring between the guide RNA and the complementary strand of the target sequence. For example, gRNA used by Cas9 nuclease or its functional mutant is often composed of crRNA and tracrRNA molecules that are partially complemented to form the complex, wherein crRNA contains a guide sequence (referred to as seed sequence) that has sufficient identity to the target sequence so as to be hybridized with the complementary strand of the target sequence and directs a CRISPR complex (Cas9+crRNA+tracerRNA) to specifically bind to the target sequence. However, it has been known in the art that single guide RNA (sgRNA) can be designed, which simultaneously contains the features of crRNA and tracrRNA, gRNA used by Cpf1 nuclease or its functional variant is often only composed of matured crRNA molecules, which is also referred to as sgRNA. Designing suitable gRNA based on the CRISPR effector protein as used and the target sequence to be edited is within the skill of those skilled person in the art.

In some specific embodiments of the invention, the guide RNA is a sgRNA. For example, the sgRNA comprises a scaffold shown in SEQ ID NO: 16.

The sequence specific nuclease for gene editing in the invention, such as zinc finger nuclease, transcription activating factor-like effector nuclease or CRISPR nuclease or a variant thereof, may further comprise a sub-cellular localization signal (such as a nuclear localization signal), a peptide linker, a detectable label and other elements. For example, the base editor in the CRISPR base editing system generally comprises one or more nuclear localization signal (NLS) for entering the cell nucleus to realize the editing of the chromosomal DNA.

The expression construct of the invention can be introduced into the plant cell by a variety of methods known in the art, the methods comprise but are not limited to gene gun method. PEG-mediated protoplast transformation and *Agrobacterium*-mediated transformation.

In some embodiments of the present invention, the plant cell of the invention is a cell suitable for regenerating an intact plant cell by tissue culture. Examples of suitable plant cells include, but are not limited to, protoplast cells, callus cells, immature embryonic cells, and explants cells.

Methods for regenerating a transformed intact plant by culturing the transformed protoplast, callus, immature embryo or explant is known in the art. In the regeneration process, the transformant can also be selected based on the selectable marker carried on the introduced expression construct. In some embodiments, the regeneration is carried out in the absence of a selection pressure. In some embodiments, the transformant can be selected under a moderately stringent selection condition. The moderately stringent condition refers to a condition that does not completely inhibit the growth of the non-transformants. For example, moderately stringent selection does not inhibit the growth of the transformants but partially inhibit the growth of the non-transformants. For example, under moderately stringent selection, the non-transformants can grow but slower or weaker than the transformant. The moderately stringent selection can be determined by those skilled in the art for specific plants and specific selectable markers.

In some embodiments of the invention, the expression construct of the invention is transiently transformed into the plant cell. Transient transformation refers to introducing the construct into the cell, allowing it to exert the function but not integrated into the cell genome. This is particularly useful for gene editing, because transgene-free modified plants can be produced. Another surprising discovery of the present invention is that even transient expression of the combination of WUS, BBM and SERK, or a combination of GRF and GIF, can improve the efficiency of regeneration, transformation and/or gene editing of the plant.

Plants suitable for transformation or gene editing using the methods of the present invention may be monocotyledonous plants or dicotyledonous plants. For example, examples of the plants include, but are not limited to, wheat, strawberry, rice, corn, soybean, sunflower, sorghum, canola, alfalfa, cotton, barley, millet, sugar cane, tomato, tobacco, cassava and potato.

The method of the invention is particularly suitable for genetic transformation or gene editing in a plant variety or genotype that previously is difficult to be transformed. In some specific embodiments, the plant is wheat, for example, the wheat is Jimai 20, Jimai 22. Beijing 411. Shannong 20, Shannon 116, Xiaoyan 54, Zhoumai 27, Zhoumai 28 and Zhongmai 175. In some specific embodiments, the plant is soybean, for example, the soybean is Williams 82, zhonghuang 13 and Hefeng 25. In some specific embodiments, the plant is strawberry, such as strawberry Benihoppe.

In order to obtain effective expression in the plant, in some embodiments of the invention, the coding nucleic acid sequence or the nucleic acid sequence of interest is codon optimized against the plant species of which the genome is to be modified.

Codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (TRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at <<www>>.<<kazusa>>.<<or.>><<jp>><</codon/>> and these tables can be adapted in a number of ways. See Nakamura, Y., et al. "Codon usage tabulated from the international DNA sequence databases: status for the year 2000" Nucl. Acids Res. 28:292 (2000).

In one aspect, the invention provides a plant obtained by the method of the invention and progeny thereof.

EXAMPLES

Further understanding of the present invention can be obtained by reference to some specific examples given herein, which examples are only used to illustrate the invention, and are not intended to limit the scope of the invention. Obviously, various modifications and changes may be made to the present invention without departing from the spirit of the present invention, and therefore these changes and variations are also within the scope of the present application.

Example 1. Development Regulatory Factor WUS, SERK, LEC1, KN1, BBM Improving Wheat Genetic Transformation and Gene Editing Efficiency Recently, using the totipotency of plant cell, ectopic expression of specific DR combination (such as WUS, STM, MP, BBM and so on) in somatic cell has the potential for inducing meristematic tissues. Co-expression of DRs and gene editing system can greatly shorten the plant tissue culture process to obtain the genome edited plant individuals. In addition, researches showed that by expressing some genes associated with the cell division of meristematic tissues can also achieve plant genome editing without tissue culture. The development of new plant cell (especially apical meristematic tissue cells) division-promoting and development-related genes, is of important significance especially for plant such as wheat which is difficult to transform.

This example is to select candidate genes which may promote plant cell division and plant regeneration. These candidate genes include WUS, BBM, SERK, KN1 and LEC.

1.1. Vector Construction

Corn WUS, SERK. LEC, BBM and KN1 were selected to test. The following plant expression vectors were constructed:
1. CRISPR/Cas9 knockout vector: UBI-Cas9
2. The single base editing vector. UBI-A3A
3. sgRNA expression vector: TaU6-sgRNA
4. ZmWUS/BBM combination: nos-ZmWUS-ubi-ZmBBM
5. ZmWUS/BBM/SERK combination: nos-ZmWUS-ubi-ZmBBM-ZmSERK
6. ZmWUS/BBM/LEC1 combination: nos-ZmWUS-ubi-ZmBBM-ZmLEC1
7. ZmWUS/KN1/LEC combination: nos-ZmWUS-ubi-ZmKNI-ZmLECI The structures of the plant expression vectors are shown in FIG. 1. The vectors 4-7 were also referred to as promoting (booster) vectors.

1.2 Transforming Wheat Immature Embryo with Gene Gun and Analyzing Transformation and Editing Efficiency UBI-Cas9 or UBI-A3A respectively combined with TaU6-sgRNA and four promoting (booster) expression vectors were co-transformed. Wheat ALS gene was selected as the editing site. The established wheat gene gun transformation technology was used to transform. Plants were obtained after tissue culture and regeneration, and mutants were detected by PCR/RE method. The results of UBI-A3A are shown in Table I below.

TABLE 1

| booster plasmid | No. of bombardment | Selective agent | No. of mutants |
| --- | --- | --- | --- |
| nos-ZmWUS-ubi-ZmBBM | 5 | F7.5 | 10 |
| Ubi-A3A | 5 | F7.5 | 9 |
| UB1-A3A | 5 | F7.5 | 4 |
| nos-ZmWUS-ubi-ZmBBM-ZmSERK | 5 | F7.5 | 17 |
| nos-ZmWUS-ubi-ZmBBM-ZmLEC1 | 5 | F7.5 | 4 |
| nos-ZmWUS-ubi-ZmKN1-ZmLEC1 | 5 | F7.5 | 7 |

The above results showed that: compared with the control UBI-A3A without booster, the efficiency of nos-ZmWUS-ubi-ZmBBM-ZmSERK has significant improving effect for base editing system UBI-A3A.

Example 2. Plant Growth Control Factor GRF/Gif Improve Wheat Genetic Transformation and Gene Editing Efficiency GRF transcription factors are specific transcription factors in plants, mainly control plant cell size, chloroplast proliferation, gynogenesis, osmotic stress and other plant growth and development processes. GRF and GIF can form transcription co-activation factor complex. GIFs are homologous to human transcription co-activation factor synovial sarcoma transport protein (synovial translocation protein. SYT). In plants, the GRF4 and gif1 plays a role in cell proliferation and maintains the proliferation ability of the meristematic cell during the flower organ development. The inventors selected wheat GRF4 and wheat gif to detect whether the genetic transformation and gene editing of the wheat can be improved.

2.1. Vector Construction

Figure 2:
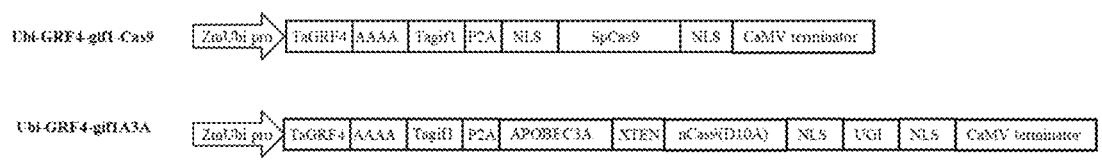
FIG. 2 shows expression constructs for verifying the effect of GRF4 and gif1 combination on genetic transformation and gene editing efficiency in wheat.

Wheat GRF4 and gif1 were fused by linker AAAA; the ZmUBI promoter was used for driving expression. In addition, to reduce the number of vectors, the GRF4-AAAA-gif1 fusion protein and Cas9 or A3A-nCas9 were constructed on the same plant expression vector, and the P2A was used for separate expression. The structure of the constructed vector is shown in FIG. 2.

2.2. Transforming Wheat Immature Embryo with Gene Gun and Analyzing Transformation and Editing Efficiency The established wheat gene gun transformation technology was used to co-transform the combination of the booster vector and TaU6-sgRNA constructed in 2.1; combination of UBI-Cas9 or UBI-A3A and TaU6-sgRNA was co-transformed as a control. Wheat ALS gene was selected as the editing site. Plants were obtained after tissue culture and regeneration, and mutants were detected by PCR/RE method. The results are shown in the following table.

TABLE 2

| Plasmid bombarded | No. of bombardment | No. of seedling | No. of mutants |
| --- | --- | --- | --- |
| Ubi-GRF4-gih1-Cas9 | 5 | 158 | 12 |
| Ubi-Cas9 | 5 | 91 | 0 |
| UBI-GRF4-gif1-A3A | 5 | F7.5 | 21 |
| Ubi-A3A | 5 | F7.5 | 6 |

The above results show that: as compared with the control UBI-Cas9 and UBI-A3A. UBI-GRF4-gif-Cas9 and UBI-GRF4-gif1-A3A with wheat GRF4/gif1 added showed significantly increased number of mutants, which was increased by a factor of about 3-12. The plant growth control factors can be used as important regulatory proteins to promote plant genetic transformation and improve efficiency of genome editing.

Example 3. Optimizing GRF4/Gif1 to Improve the Wheat Gene Editing Efficiency

Figure 3:
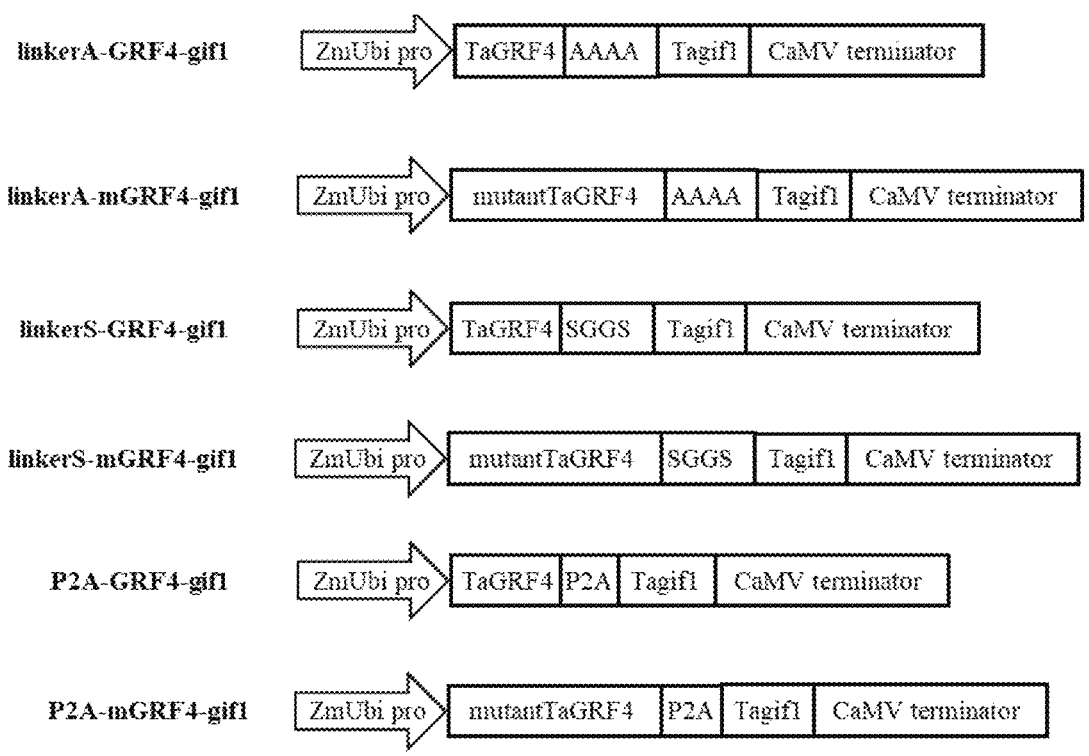
FIG. 3 shows the expression constructs for GRF4 and gif1 combinatorial optimization experiment.

In order to further improve the efficiency of wheat genome editing, the linker of the GRF4 and gif1 fusion protein was optimized. The linkerA (AAAA) was replaced by linkerS (SGGS). In addition, the miR396/GRF control pattern is very conservative in plants, miR396 has down-regulation effect to GRF4. The miR396 binding site of GRF4 was mutated, which may increase expression of GRF4, so as to improve the efficiency of wheat genome editing. The booster vectors shown in FIG. 3 were constructed.

The vectors respectively combined with the wheat ALS gene targeting A3A base editing system in the above Examples were transformed through gene gun into wheat immature embryo. The results shown in the following table.

TABLE 3

| Booster plasmid | Transformation time | No. of bombardment | No. of seedling | No. of mutants |
|---|---|---|---|---|
| linkerA-GRF4-gif1 | 2019 Sep. 24 | 3 | 275 | 71 |
| linkerA-mGRF4-gif1 | 2019 Sep. 24 | 3 | 403 | 125 |
| linkerS-GRF4-gif1 | 2019 Sep. 24 | 2 | 154 | 12 |
| linkerS-mGRF4-gif1 | 2019 Sep. 24 | 2 | 182 | 28 |
| P2A-GRF4-gif1 | 2019 Sep. 26 | 4 | 191 | 4 |
| P2A-mGRF4-gif1 | 2019 Sep. 26 | 3 | 165 | 1 |

As can be seen from the above results, editing efficiency of linkerA was higher than LinkerS. Most importantly, the mutation of the binding site of the miR396 of GRF4 increased the regeneration efficiency of the wheat with large amplitude, and also increased the mutation efficiency in large amplitude.

Example 4. GRF4/Gif1 Improves the Editing Efficiency in Wheat of Different Genotype In order to investigate whether GRF4/gif1 can improve the editing efficiency of other wheat varieties, namely breaking the limitation of wheat genotype on genetic transformation, several varieties with low transformation efficiency by traditional methods were selected for testing. The results are as follows:

TABLE 4

| No. | Booster plasmid | Transformation time | No. of bombardment | Selective agent | No. of mutants |
|---|---|---|---|---|---|
| | | Xiaoyan 54 | | | |
| Pm20.25 | linkerA-GRF4-gif1 | 2019 May 16 | 5 | F7.5 | 12 |
| Pm20.27 | / | 2019 May 16 | 5 | F7.5 | 0 |
| | | Jimai 22 | | | |
| Pm20.26 | linkerA-GRF4-gif1 | 2019 May 16 | 5 | F7.5 | 1 |
| Pm20.28 | / | 2019 May 16 | 5 | F7.5 | 0 |

The results show that the wheat growth transcription factor GFR4/gif1 can significantly realize editing of a plurality of varieties, breaking the restriction of genotypes.

Example 5. GRF4/Gif1 Improves Wheat Transformation Efficiency and Gene Editing Efficiency Mediated by agrobacterium In order to further investigate whether GRF4/gif1 can improve the efficiency of wheat transformation efficiency and gene editing mediated by agrobacteriumn, the GRF4/gif1 was constructed on the agrobacterium gene editing vector, transfecting wheat immature embryo by agrobacterium. The results are shown in the following table.

TABLE 5

| transformed agrobacterium | Recipient material | No. of young embryo | mutant |
|---|---|---|---|
| ubi-GRF4-A3A-ALS174-Hyg | Kenong 199 | 519 | 12 |
| A3A-ALS174-Hyg | Kenong 199 | 199 | 0 |

It can be seen that GRF/gif can significantly improve the editing efficiency mediated by agrobacterium transformation, increasing the gene editing efficiency from zero to 2.3%.

Figure 4:
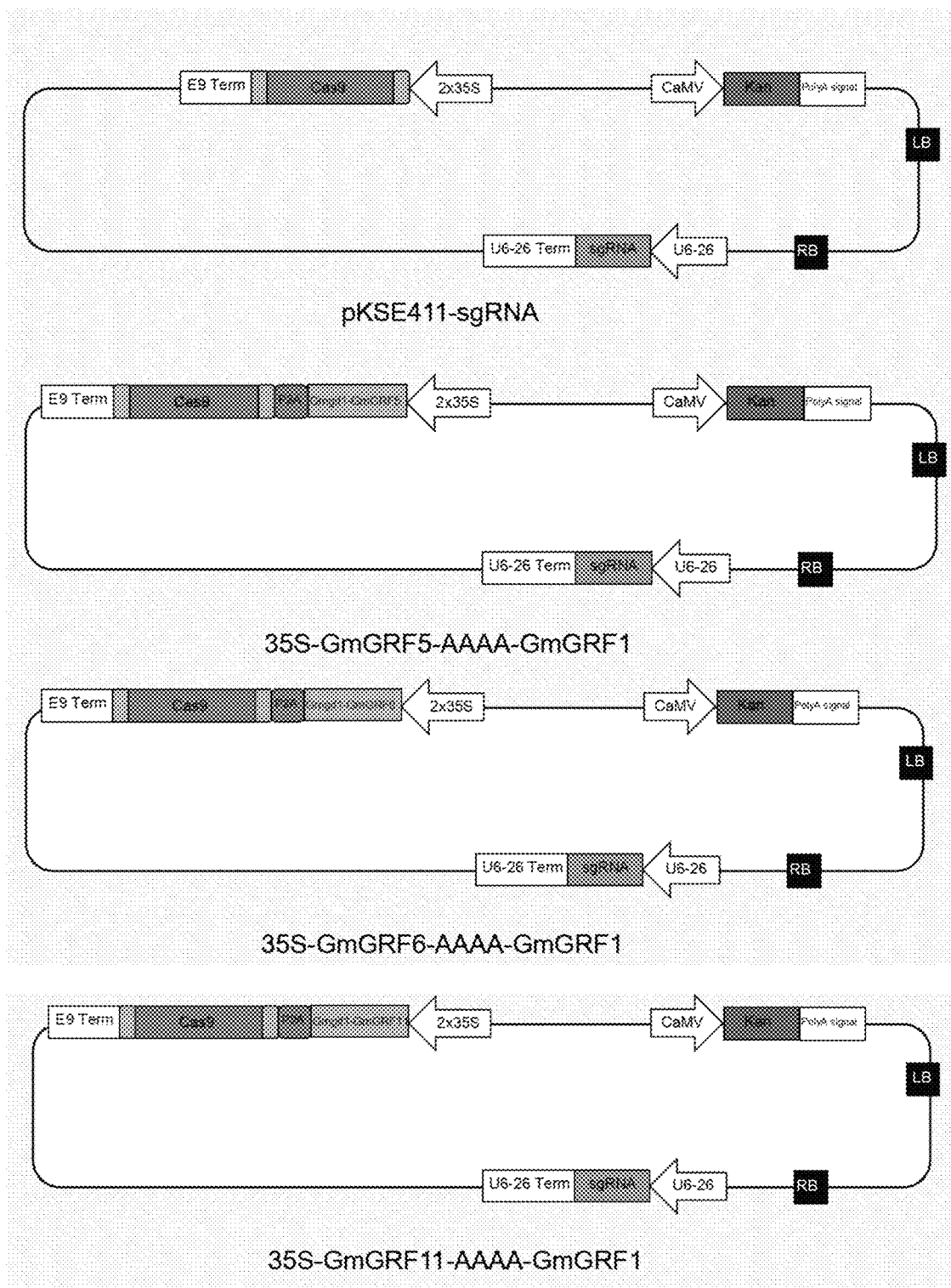
FIG. 4 shows the soybean GRF/gif expression construct.

Example 6. GRF/Gif Improves Soybean Transformation Efficiency and Gene Editing Efficiency Mediated by Agrobacterium 6.1. Soybean GRF/Gif Vector Construction The result of the above Examples shows that the plant growth factor GRF/gif combination can improve the regeneration efficiency of tissue culture of monocotyledon wheat and efficiency of gene editing. In order to investigate whether GRF can increase tissue culture plant regeneration efficiency of dicotyledonous plants, endogenous GRF genes of dicotyledon soybean were selected to test whether they can improve the plant regeneration efficiency of soybean. GFR5. GRF6, GRF11, GRF18 of soybean were selected for test, and connected with gif1 of soybean by AAAA linker. The fusion proteins and Cas9 were separated and linked by P2A; the expression was driven by 35s promoter; the sgRNA was initiated by the U6-26 promoter; and the sgRNA was constructed on the same carrier. The constructed expression vector is shown in FIG. 4.

6.2 Soybean GRF/Gif Improve the Regeneration Efficiency of Soybean Callus

The above constructed vectors were transformed into soybean by agrobacterium; the result of the soybean regeneration efficiency is shown in the following table.

TABLE 6

| project starting time | RECO | SBA | EBA | ETC | 20200303 elongated seedlings/explants | elongation rate |
|---|---|---|---|---|---|---|
| 35S-GmGFR5-AAAA-Gmgif1 | 187 | 147 | 178 | 144 | 35/124 | 0.282258 |
| 35S-GmGFR6-AAAA-Gmgif1 | 195 | 100 | 64 | 56 | 3/56 | 0.053571 |
| 35S-GmGFR18-AAAA-Gmgif1 | 188 | 161 | 156 | 124 | 9/124 | 0.072581 |
| 35S-GmGFR11-AAAA-Gmgif1 | 194 | 168 | 160 | 157 | 14/124 | 0.112903 |
| pKSE411-shRNA | 178 | 107 | 72 | 64 | 4/60 | 0.066667 |

RECO: representing soybean infection, recovery culture stage; SBA: represents the soybean entering selection stage; EBA: represents the soybean enters the elongation stage. ETC: represents soybean elongation culture stage, not selection added.

The result shows that the soybean endogenous GFR5 in combination with gif1 can significantly improve the regeneration efficiency of soybean callus. In addition, the gene editing efficiency of the endogenous gene of the regeneration plant is detected, showing that the gene editing efficiency was also significantly improved.

Example 7. The GmGRF5-GmGIF1 Boosts Soybean Regeneration

Of the 22 GRF genes predicted in the soybean genome, GmGRF5. GmGRF6, GmGRF11, and GmGRF18, which are specifically (or preferentially) expressed in flower and shoot apical meristems (Chen et al., 2019), were chosen to form fusion proteins with soybean GmGIF1, whose homolog gene in Arabidopsis and rice strongly expresses in flowers and shoot apical meristems to control plant growth (Kim, 2019). Each GmGRF-GmGIF1 fusion protein was co-expressed with a CRISPR/Cas9 expression cassette, generating four constructs (pGmGRF5-GmGIF1, pGmGRF6-GmGIF1, pGmGRF11-GmGIF1, and pGmGRF18-GmGIF1) (FIG. 5A), targeting two copies of the soybean fatty acid desaturase 2 (GmFAD2) gene (FIG. 5B), whose product catalyzes the conversion of oleic acid to linoleic acid and lowers the quality of soybean oil quality (Haun et al., 2014). The transformation efficiencies and frequencies of editing of GmFAD2 by the GmGRF-GmGIF1 complexes were evaluated.

As shown in FIG. 5C, each of the four pGmGRF-GmGIF1 constructs was transformed into soybean cultivar Williams 82, one of the most popular transformable genotypes, by Agrobacterium-mediated transformation (Jia et al., 2015). Construct pBSE401 (Xing et al., 2014), which contains the GmFAD2-targeting CRISPR/Cas9 expression cassette but no GmGRF-GmGIF1 complex, was used as control (FIG. 5A). The number of explants recovered after introduction of each of the four GmGRF-GmGIF1-containing constructs was similar to that obtained with pBSE401 (Tables 7 and 8). However, after two weeks of bud induction and two weeks of shoot proliferation with glufosinate selection, the explants transformed with pGmGRF5-GmGIF1 produced large numbers of buds: 93.8% of the explants in each transformation event produced multiple buds, compared with 58.4% in the control and similar proportions in the explants infected with other GmGRF-GIF1 constructs (FIG. 5D, Tables 7 and 8). On elongation medium with moderate stringency of glufosinate selection, the average number of elongated shoots (≥2 cm) increased 2.8-fold with pGmGRF5-GmGIF1 (432.3) relative to the control (156.0) and more than 2.5-fold relative to the other constructs (FIGS. 5E and 1G. Tables 7 and 8). Similarly, average numbers of elongated large shoots (≥9 cm) were 2.5-fold greater with pGmGRF5-GmGIF1 (85.3) than with pBSE401 (33.7) (FIGS. 5E and 5H, Tables 7 and 8). The inventors also found that the explants transformed with pGmGRF5-GmGIF1 produced significantly more putative glufosinate resistant shoots per explant (3.0) than the control (1.1) (FIGS. 5F, 5G and 5H. Tables 7 and 8). Also, the time from the initial transformation to when the first elongated shoot reached 9 cm was 58 days for pGmGRF5-GmGIF1, compared with 70 for the control (Tables 7 and 8). There were no significant differences in shoot induction, shoot elongation, and time from the initial transformation to first 9 cm shoot between explants infected with pBSE401 and the three other GmGRF-GmGIF1 complexes (Tables 7 and 8). Collectively, these data show that the GmGRF5-GmGIF1 complex stimulates regeneration of soybean explants.

Example 8. The GmGRF5-GmGIF1 Complex Enhances Genome Editing in Soybean

Figures 10A, 10B, 10C:
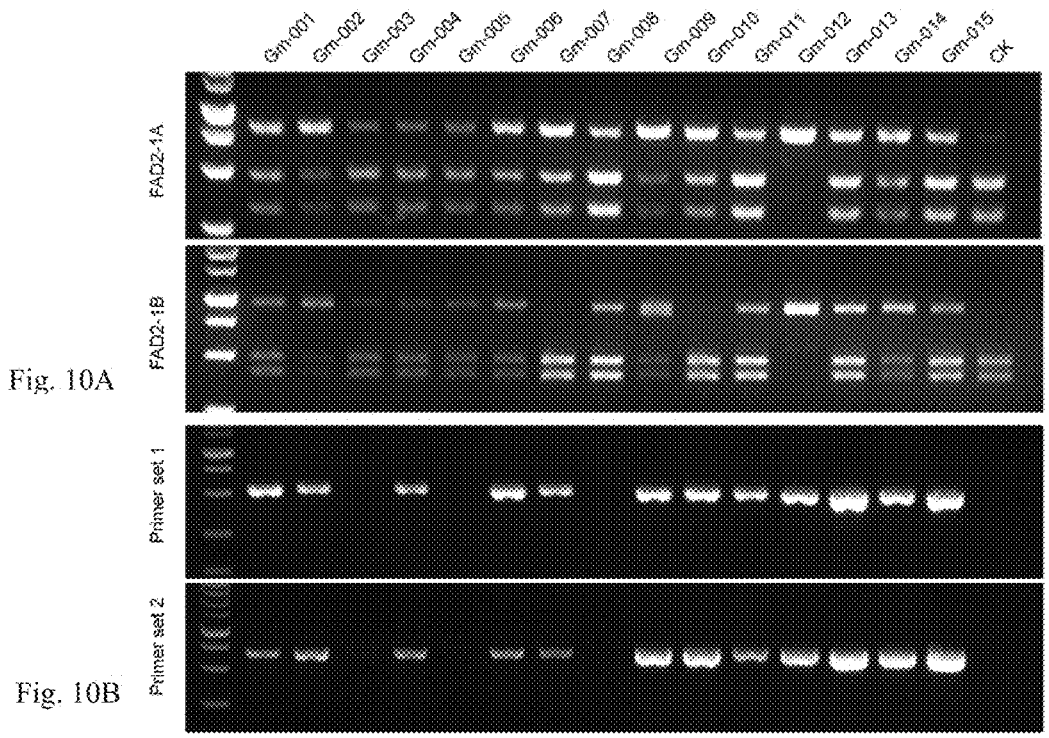
FIGS. 10A-10C. Detection of mutations and transgene-free mutant plants in 15 representative Williams 82 soybean lines transformed with pGmGRF5-GmGIF1.

Efficient regeneration is a prerequisite for successful plant genetic transformation and genome editing. Consistent with the above regeneration frequencies, the transformation efficiency (TE) of explants when pGmGRF5-GmGIF1 was used was 21.8%, significantly higher than the 8.5% with pBSE401, while the other complexes all yielded frequencies of no more than 10.2% (FIG. 5I, Tables 7 and 8). The inventors used PCR-RE assays and Sanger sequencing to detect mutations of GmFAD2 in the regenerated lines. Again, in agreement with the TEs, explants transformed with pGmGRF5-GmGIF1 contained more edits and significantly higher mutation frequencies (MF) than those transformed with pBSE401 (FIG. 5J, Tables 7 and 8). Also, a large number of the transformants had mutations in both FAD2-1A and FAD2-1B, indicating that both genes were efficiently mutated (FIG. 10. Table 9). Intriguingly, among the 94 mutants from transformation with pGmGRF5-GmGIF1, 15 (16.0%) were transgene-free. (FIG. 10. Tables 7 and 8).

To see whether the constitutive expression of GmGRF-GmGIF1 complexes caused phenotypic abnormalities, the inventors grew GmFAD2-edited Williams 82 plants transformed with pGmGRF5-GmGIF1 and pBSE401 in a greenhouse. Throughout the whole growth period, Williams 82 plants transformed with pGmGRF5-GmGIF1 were fertile and no morphologic differences were observed between the two sets of lines (FIG. 5K), suggesting that that GmGRF5-GmGIF1 greatly stimulates genome-editing of soybean without producing undesirable side-effects.

Example 9. The GmGRF5-GmGIF1 Complex Enables Genome Editing of Marginally Transformable Soybean Cultivars Because the pGmGRF5-GmGIF1 construct yielded the highest rates of regeneration, genetics transformation, and mutation among the four GmGRF-GmGIF1 complexes, it was used in an attempt to increase the transformation and genome-editing efficiencies in two marginally transformable but commercially important soybean cultivars, Zhonghuang 13 and Hefeng 25. The GmGRF5-GmGIF1 complex was transformed into Zhonghuang 13 and Hefeng 25 by Agrobacterium-mediated transformation, in combination with a GmFAD2-targeting CRISPR/Cas9 expression cassette, with pBSE401 as control. In Zhonghuang 13. GmGRF5-GmGIF1 gave rise to substantially higher frequencies of regeneration (84.0%), elongated putative glufosinate-resistant shoots (312.6, ≥2 cm in length), and elongated putative glufosinate-resistant shoots per explant (2.6), as well as higher TE (18.2%) and MF (16.0%), than did pBSE401 (65.6%, 233.0, 1.7, 5.3% and 2.4%, respectively) (FIGS. 6A, 6B, 6E and 6G, Tables 7 and 8). In Hefeng 25, about 71.1% of explants transformed with pGmGRF5-GmGIF1 produced at least one elongated shoot ≥2 cm, whereas none of the explants transformed with pBSE401 produced shoots (FIG. 6A, 6C-6E, Tables 7 and 8). The transformation efficiency of the explants transformed with pGmGRF5-GmGIF1 was 2.5%, and five transgenic plants had mutations in the GmFAD2 target sites (FIGS. 6F and 6G, Tables 7, and 4). One transgene-free editing event was also identified (Tables 7 and 8). Evidently the GmGRF5-GmGIF1 complex greatly stimulates regeneration and hence genetic transformation and genome editing in marginally transformable soybean cultivars. Also, the GmGRF5-GmGIF1 complex is able to generate transgene-free mutants due to transient expression of the CRISPR DNA and the fact that expression of the booster genes stimulated much more extensive cell proliferation, while the selection pressure was relatively low.

Example 10. The Soybean GmGRF5-GmGIF1 Complex Promotes Regeneration of Strawberry and Genome Editing The regeneration of another dicot, strawberry (*Fragaria ananassa*), is genotype-dependent. Transformation of one of the most widely cultivated octoploid strawberry cultivars, Benihoppe, is extremely difficult, and no genome editing events have yet been obtained in this cultivar (Folta and Dhingra, 2006).

Figure 11A:
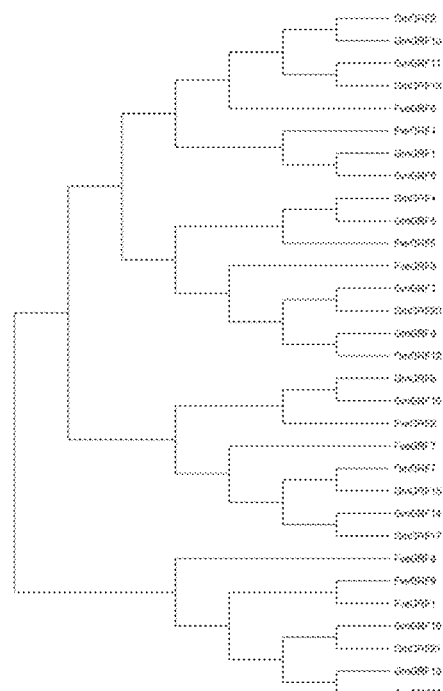
FIGS. 11A-11C. Phylogenetic analysis of GRFs from *Glycine max* (Gm) and *Fragaria vesca* (Fve) and the sgRNA designed to generate mutant strawberry FaPL genes.
Figure 11B:
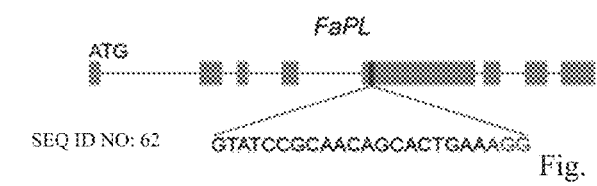

The inventors examined the regeneration and genome editing of Benihoppe using the soybean GmGRF5-GmGIF1 complex because strawberry GRF proteins are close to soybean GRFs (FIG. 11A). The fusion protein was co-expressed with Cas9 in a single expression cassette, in vector pHUE411-GFP-GmGRF5-GmGIF1 (FIG. 7A). The pectate lyase gene, FaPL, which contributes to loss of strawberry fruit firmness (Jimenez-Bermudez et al., 2002), was targeted by Cas9 (FIG. 11B) and green fluorescent protein (GFP) was used as a visual reporter that allowed continuous monitoring of transgenic events. The control vector (pHUE411-GFP) contained Cas9, the sgRNA targeting FaPL, and the GFP gene. A total of 541 and 540 strawberry leaf explants were infected by the *Agrobacterium* contained pHUE411-GFP-GmGRF5-GmGIF1 and the control vector, respectively (FIG. 7B). Calli from leaf explants induced on callus induction medium were screened for GFP expression three weeks after infection. 19.6% (106/541) of the explants transformed with GmGRF5-GmGIF1 produced at least one GFP positive callus, compared with 6.5% (35/540) in the control (FIG. 7B).

Figure 11C:
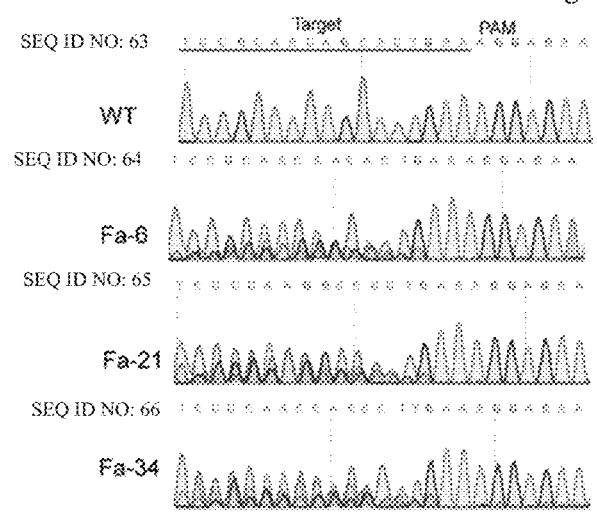

Moreover, the leaf explants transformed with GmGRF5-GmGIF1 tended to form multiple and large calli with strong GFP fluorescence, whereas, only a few small GFP-positive spots were observed on callus masses in the control (FIG. 7C). During growth on shoot induction medium the calli on explants transformed with GmGRF5-GmGIF1 grow more vigorously than those on the control (FIG. 7D), and shoot initiation occurred on 8.1% of the former calli from explants infected with GmGRF5-GmGIF1 five weeks after infection compared with only 3.0% of the latter (FIG. 7D). The transformation efficiency of the explants transformed with GmGRF5-GmGIF1 was 0.9%, and mutations in the FaPL target sites were detected in 0.6% of the explants (FIG. 7B. FIG. 11C), whereas neither transgenic plants and nor mutant plants were detected in the control (FIG. 7B). These data demonstrate that the GmGRF5-GmGIF1 complex could promote the regeneration, genetic transformation and genome editing of a transformation-recalcitrant strawberry cultivar, showing that GmGRF5-GmGIF1 stimulates genetic transformation and genome editing in other dicot plants.

Example 11. Comparison of the Effects of Wild Type TaGRF4-TaGIF1 and Mutated TaGRF4-TaGIF1 on Regeneration and Genome Editing of Common Wheat To broaden the application of GRF-GIF1 complexes, the inventors examined their effect in the monocot, common wheat, in which transformation is limited to a narrow range of genotypes (He et al., 2015, Jones et al., 2005). Phylogenetic tree analysis suggested that the soybean GRF family, including GmGRF5, is distantly related to the monocot GRF family of rice (Chen et al., 2019). Previous work has also shown that overexpression of OsGRF4 and its coactivator OsGIF1 stimulates the cell proliferation and seed size in rice (Sun et al., 2016; Hu et al., 2015). Therefore, the inventors tested the effects of the rice homologs. TaGRF4, and TaGIF1, in common wheat (FIG. 12) while adding two modifications.

First, TaGRF4 was fused with TaGRF1 to form a TaGRF4-TaGIF1 complex, and the miR396 target site in TaGRF4 was inactivated by five point mutations (mTaGRF4-TaGIF1) to increase transcription of TaGRF4 (FIGS. 8A and 8B). Second, a transient expression strategy (Liang et al., 2017; Zhang et al., 2016; Zhang et al., 2018), which avoids any selection pressure throughout the whole tissue culture procedure, was used to generate transgene-free mutants in the TO generation (FIG. 8C). The wild type complex TaGRF4-TaGIF1, and mutant complex, mTaGRF4-TaGIF1, were separately transformed into the efficiently transformable common wheat cultivars Bobwhite and Kenong 199 (FIGS. 8B and 8C), together with the cytosine base editor pUBI-A3A vector containing an sgRNA for the common wheat acetolactate synthase gene (TaALS) (FIG. 13), in which C-to-T substitutions at Pro197 confers resistance to nicosulfuron (Zhang et al., 2019; Zong et al., 2018). The combination of pUBI-A3A and pUBI-GFP served as a control. After six weeks on non-selective media, numbers of regenerated plants and TaALS mutations were analyzed.

The inventors found that immature embryos of both Bobwhite and Kenong 199 transformed with TaGRF4-TaGIF1 produced more regenerated plants (508.0% and 654.5%, respectively) than the control groups (81.0% and 136.9%, respectively) (FIG. 8D. Table 11). Moreover, mTaGRF4-TaGIF1 gave even higher regeneration ratios of 630.1% and 1165.4%, in Bobwhite and Kenong 199, respectively, 1.2- and 1.7-fold higher than the regeneration frequency with the wild type TaGRF4-TaGIF1 complex, and 7.8- and 8.5-fold higher than with the control construct (FIG. 8D. Tables 11 and 12). The inventors also examined genome editing at the TaALS target site using PCR-RE assays and Sanger sequencing. Consistent with the regeneration ratios, the Bobwhite and Kenong 199 plants transformed with the TaGRF4-TaGIF1 complex had higher mutation frequencies (32.7% and 103.4%, respectively) than plants transformed with the control construct (9.9% and 17.7%, respectively) (FIGS. 8E and 8D, Tables 11 and 12). Among the plants generated by the mTaGRF4-TaGIF1 complex the inventors identifies 216 mutants in 343 embryos (63.3%) and 577 mutants in 328 embryos (176.1%) in Bobwhite and Kenong 199, respectively, 1.7-1.9-fold higher than in the plants generated by the TaGRF4-TaGIF1 complex, and 6.4-9.9-fold higher than in those in the control groups (FIG. 8E, Tables 11 and 12).

Since the plasmids were delivered using a transient expression approach (FIG. 8C), there seemed a high probability that the TaGRF4-TaGIF1 and base editor DNA constructs had not been integrated into the genome of the mutant plants. To test for the presence of plasmid DNAs in the regenerated TO mutants the inventors used a total of six primer sets (three for pUBI-A3A, three for pTaGRF4-TaGIF1 or pmTaGRF-TaGIF1) to amplify different regions of the TaGRF4-TaGIF1 and the base editor constructs, together covering almost the entire constructs (FIG. 8F). Based on the PCR analysis, the two vectors (pUBI-A3A and pTaGRF4-TaGIF1/pmTaGRF4-TaGIF1) were absent from 47.1%-55.4% of the mutants of Bobwhite and Kenong 199 treated with TaGRF4-TaGIF1, mTaGRF4-TaGIF1 and the control construct (FIG. 8G, Tables 11 and 12). The total numbers of transgene-free mutants in the mTaGRF4-Ta- GIF1-treated groups were 6.0-11.6-fold higher than in the control groups (Tables 11 and 12). Moreover, when the inventors grew the transgene-free mutants of Kenong 199 derived from mTaGRF4-TaGIF1 in a greenhouse the inventors found that they were fertile and displayed no obvious phenotypic differences from WT plants throughout all of development (FIG. 8H).

In summary, the TaGRF4-TaGIF1 complex increased both regeneration frequency and genome-editing efficiency in common wheat and disruption of the miR396 target site further enhanced its efficiency. Furthermore, transient expression of mTaGRF4-TaGIF1 had no ill-effect on phenotype.

Example 12. The Mutated TaGRF4-TaGIF1 Complex Extends Genome Editing in Broad Common Wheat Cultivars The inventors tested whether the mTaGRF4-TaGIF1 complex improved regeneration rates and genome editing efficiencies in various common wheat cultivars that are widely grown in China, pUBI-A3A vector, containing an sgRNA for TaALS, was delivered with mTaGRF4-TaGIF1 into immature embryos of nine major Chinese common wheat cultivars Jimai 20, Jimai 22, Jing 411. Shannong 20, Shannong 116, Xiaoyan 54, Zhoumai 27, Zhoumai 28 and Zhongmai 175 according to the procedure in FIG. 8C. The combination of pUBI-A3A and pUBI-GFP served as a control.

After six weeks on non-selective medium, the inventors found that mTaGRF4-TaGIF1 stimulated regeneration of these common wheat cultivars, and regeneration frequencies, which ranged from 9.9%-440.8%, were significantly higher than in the corresponding controls (0%-187.3%) (FIGS. 9A and 9B. Tables 13 and 14). In particular, mTaGRF4-TaGIF1 provoked substantial the regeneration and genome editing of Xiaoyan 54, Zhoumai 28, Jimai 20, Jimai 22 and Shannong 20, which is normally very difficult (FIGS. 9A and 9B. Table 13). Mutations in the TaALS sites were detected by PCR-RE assays and Sanger sequencing in all of these nine common wheat cultivars transformed with mTaGRF4-TaGIF1. Mutation frequencies ranged from 1.2-8.1%, compared with 0-3.9% in the control groups, five of which contained no mutants (FIG. 5C. Table 8). Moreover, homozygous mutant frequencies (HMF) in the nine cultivars transformed with mTaGRF4-TaGIF1 ranged from 10.0-55.6%, which was much higher than in the controls (0-15.4%) (Tables 13 and 15). The inventors also identified 22.2-66.7% transgene-free mutants among the nine cultivars transformed with the mTaGRF4-TaGIF1 complex (Table 13). In contrast, transgene-free mutants were only found in Shannong 116, Zhoumai 27 and Zhongmai 175 transformed with the control plasmid (Table 13). Thus, the mTaGRF4-TaGIF1 complex stimulates regeneration and genome editing in all nine common wheat cultivars.

Soybean is one of the most important sources of edible oils and proteins, but its transformation rates remain very low despite the many available genetic transformation methods (Christou, 1992; Trick and Finer, 1998; Yang et al., 2016). Thus, the development of an improved transformation system for soybean is urgently needed. Plant GRF and GIF genes are highly expressed in meristematic tissues, including leaf and floral organ primordia and shoot apical meristems (Kim, 2019; Omidbakhshfard et al., 2015; Zhang et al., 2018), and might potentially be developed as boosters to stimulate plant regeneration so enhance genetic transformation and genome editing rates. The inventors screened and tested four GmGRF-GmGIF1 complexes in Williams 82, and found a transformation rate of 21.8% using the GmGRF5-GmGIF1 complex (FIG. 5I, Table 7), which is much higher than the transformation rate obtained using traditional transformation methods (Finer and McMullen, 1991; Hinchee et al., 1988). It should be noted that GmGRF5 is predicated as GmGRF7 in GenBank (XM_003526701.4), since it is most similar to *Arabidopsis* AtGRF7.

The genotype limitation depends on the susceptibility to *Agrobacterium* infection of the donor genotype and the regeneration ability of the explant (Jia et al., 2015). Fortunately, the GmGRF5-GmGIF1 complex improved the transformation efficiencies of Zhonghuang 13 (18.2%) and Hefeng 25 (2.5%), which are the most widely grown cultivars in China but are difficult to engineer genetically by current methods. This indicates that the GmGRF5-GmGIF1 complex can overcome the bottleneck of genotype-dependence in soybean transformation. GmGRF5-GmGIF1 enhanced recovery of transgene-free FAD2-edited events due to large number of regenerated shoots and use of a moderate stringency selection which promotes regenerated shoots as well as transgenic plant to elongate. This simulation of shoot regeneration by the GmGRF5-GmGIF1 complex and the resulting improved transformation and genome editing efficiencies in soybean and strawberry were further confirmed by the ability of soybean GROWTH-REGULATING FACTOR 5 (GmGRF5) and its cofactor soybean GIF1 complex to enhance regeneration, transformation and genome editing in diverse dicotyledonous plants.

Considering their extremely wide distributions in all land plants, and their preferential expression in meristematic tissue (Kim, 2019; Omidbakhshfard et al., 2015; Shimano et al., 2018), native GRF-GIF1 complexes could be effective in promoting regeneration in most plants. The regeneration of monocotyledonous common wheat remains genotype-dependent (He et al., 2015; Jones et al., 2005), but the inventors demonstrated that transient expression of wheat mTaGRF4-TaGIF1 dramatically improved regeneration and genome editing, and also greatly increased numbers of transgene-free mutants in nine recalcitrant Chinese commercial elite cultivars, most of which had never been regenerated and gene-edited before. The improved TaGRF4-TaGIF1 complex (mTaGRF4-TaGIF1) thus overcomes the genotype limitations to regeneration in common wheat and boosts its genome editing.

An ideal booster should not influence the morphology of regenerated plants. In the present work, no morphological changes were observed in the transgenic soybean plants, even when that the GmGRF5-GmGIF1 complex was constitutively expressed, probably due to the moderate level of its expression, which is regulated at the post-transcriptional level (Kim and Tsukaya, 2015; Liu et al., 2009; Rodriguez et al., 2010). In common wheat, the inventors found that the mTaGRF4-TaGIF1 complex performed better in improving the regeneration ability and genome editing frequency than the original TaGRF4-TaGIF1 complex. Although mTaGRF4-TaGIF1 was not repressed by miR396, the transient expression system prevented prolonged presence of this complex in the plant cells, this not only minimized morphological side effects but also generated a large number of transgene-free mutants.

In summary, the GmGRF5-GmGIF1 complex enhances the regeneration of dicotyledonous soybean and strawberry and hence stimulates genetic transformation and genome editing. Similarly, transient expression of the improved TaGRF4-TaGIF1 complex containing the inactivated miR396 target site stimulates regeneration and genome editing in monocotyledonous common wheat. Moreover, the GRF-GIF1 complexes are genotype-independent, as they work well in diverse soybean and common wheat cultivars. Given that members of the GRF gene family exists in many plant species, the GRF-GIF1 complexes described here holds great promise for improving genome-editing efficiency in a wide range of crop plants.

TABLE 7

Effect of GmGRF-GmGIF1 fusions on soybean transformation and genome editing efficiency.

| Targeted gene | Soybean cultivar | Treatment | No. explants | No. explants recovered | No. explants with multiple buds/RF (%) | No. elongated putative glufosinate-resistant shoots (≥2 cm in length) | No. elongated putative taglufosinate-resistant shoots (≥9 cm in length) |
|---|---|---|---|---|---|---|---|
| GmFAD2 (Knockout) | Williams 82 | pBSE401 (CK) | 450 | 412 | 263 (58.4 ± 5.8) | 468 (156.0 ± 14.5) | 101 (33.7 ± 4.9) |
| | | GmGRF5-GmGIF1 | 450 | 432 | 422 (93.8 ± 4.0)$^b$ | 1297 (432.3 ± 18.5) | 256 (85.3 ± 7.5) |
| | | GmGRF6-GmGIF1 | 450 | 424 | 290 (64.4 ± 3.8) | 413 (137.7 ± 14.5) | 107 (35.7 ± 6.5) |
| | | GmGRF11-GmGIF1 | 450 | 422 | 269 (59.8 ± 3.0) | 463 (154.3 ± 8.1) | 108 (36.0 ± 7.6) |
| | | GmGRF18-GmGIF1 | 450 | 419 | 379 (67.6 ± 7.2) | 520 (173.3 ± 5.8) | 124 (41.3 ± 7.3) |
| | Zhonghuang 13 | pBSE401 (CK) | 450 | 435 | 295 (65.6 ± 5.1) | 699 (233.0 ± 15.1) | 97 (32.3 ± 3.1) |
| | | GmGRF5-GmGIF1 | 450 | 440 | 378 (84.0 ± 2.7)$^b$ | 938 (312.6 ± 25.5) | 205 (68.3 ± 5.5) |
| | Hefeng 25 | pBSE401 (CK) | 450 | 372 | 243 (54.0 ± 2.9) | 0 | 0 |
| | | GmGRF5-GmGIF1 | 450 | 372 | 320 (71.1 ± 8.8)$^a$ | 164 (54.7 ± 11.2) | 36 (12.0 ± 3) |

| Targeted gene | Growth rate (days) | Average elongated shoots per explant | No. transgenic plants/TE (%) | No. mutants/MF (%) | No. transgene-free mutants/TEF (%) |
|---|---|---|---|---|---|
| GmFAD2 (Knockout) | 70.0 ± 4.0 | 1.1 ± 0.1 | 38 (8.5 ± 2.0) | 32 (7.1 ± 2.0) | 0 |
| | 57.6 ± 2.5$^a$ | 3.0 ± 0.2$^c$ | 98 (21.8 ± 2.0)$^b$ | 94 (20.8 ± 3.7) | 15 (5.0 ± 2.0) |
| | 70.3 ± 2.1 | 1.0 ± 0.1 | 37 (8.2 ± 1.6) | 32 (7.1 ± 0.8) | 0 |
| | 70.0 ± 1.0 | 1.1 ± 0.1 | 38 (8.4 ± 3.7) | 33 (7.3 ± 3.4) | 0 |
| | 69.3 ± 0.6 | 1.2 ± 0.1 | 46 (10.2 ± 1.0) | 36 (8.0 ± 0.7) | 0 |
| | 89.3 ± 0.6 | 1.7 ± 0.1 | 24 (5.3 ± 0.7) | 11 (2.4 ± 1.4) | 0 |
| | 87.3 ± 0.66 | 2.6 ± 0.2$^b$ | 82 (18.2 ± 2.0)$^b$ | 72 (16.0 ± 1.3) | 9 |
| | 1 | 1 | 0 | 0 | 0 |
| | 73.7 ± 3.7$^c$ | 0.4 ± 0.1$^b$ | 11 (2.5 ± 0.4)$^b$ | 6 (1.3 ± 0.7) | 1 (0.2 ± 0.4) |

RF (regeneration frequency) = no. of explants with multiple buds/total explant number × 100%.
Growth rates were measured from the date of the initial transformation to the date when the first elongated shoot reached 9 cm in length.
TE (transformation efficiency) = no. of transgenic plants/total explants × 100%.
Elongated shoots (≥9 cm in length) were collected for transgenic assay only once on day 75 after *Agrobacterium*-mediated transformation.
MF (mutation frequency) = no. of mutants/total transgenic plants × 100%.
TFF (transgene-free frequency) = no. of transgene-free mutants/total mutants × 100%.
The numbers and means for each treatment were calculated from data collected from three replicates of the experiment.
Data are mean ± SD (n = 3).
$^{a,b,c}$indicate significant differences compared with the CK group
(two-sided Student's t-test. $^a$indicates P < 0.05; $^b$indicates P < 0.01; $^c$indicates P < 0.001).

TABLE 8

Effect of the GmGRF-GmGIF1 fusions on soybean transformation and genome editing efficiency (Williams 82, Hefeng 25 and Zhonghuang 13, raw data).

| Targeted gene | Soybean cultivar | Repeat | Treatment | No. explants | No. explants recovered | No. explants with multiple buds/RF (%) | No. elongated putative glufosinate-resistant shoots (≥2 cm in length) | No. elongated putative glufosinate-resistant shoots (≥9 cm in length) |
|---|---|---|---|---|---|---|---|---|
| GmFAD2 (Knockout) | Williams 82 | I | pBSE401 (CK) | 150 | 138 | 97 (64.7) | 155 | 36 |
| | | | GmGRF5-GmGIF1 | 150 | 147 | 147 (98.0) | 432 | 85 |
| | | | GmGRF6-GmGIF1 | 150 | 145 | 92 (61.3) | 138 | 36 |
| | | | GmGRF11-GmGIF1 | 150 | 141 | 85 (56.7) | 145 | 35 |
| | | | GmGRF18-GmGIF1 | 150 | 136 | 106 (70.7) | 180 | 44 |
| | | II | pBSE401 (CK) | 150 | 140 | 86 (57.3) | 171 | 37 |
| | | | GmGRF5-GmGIF1 | 150 | 142 | 135 (90.0) | 451 | 93 |
| | | | GmGRF6-GmGIF1 | 150 | 144 | 103 (68.7) | 123 | 42 |
| | | | GmGRF11-GmGIF1 | 150 | 143 | 90 (60.0) | 159 | 44 |
| | | | GmGRF18-GmGIF] | 150 | 141 | 89 (59.3) | 170 | 47 |
| | | III | pBSE401 (CK) | 150 | 134 | 80 (53.3) | 142 | 28 |
| | | | GmGRF5-GmGIF1 | 150 | 143 | 140 (93.3) | 414 | 78 |
| | | | GmGRF6-GmGIF1 | 150 | 135 | 95 (63.3) | 152 | 29 |
| | | | GmGRF11-GmGIF1 | 150 | 138 | 94 (62.7) | 159 | 29 |
| | | | GmGRF18-GmGIF1 | 150 | 142 | 109 (72.7) | 170 | 33 |

TABLE 8-continued

Effect of the GmGRF-GmGIF1 fusions on soybean transformation and genome editing efficiency (Williams 82, Hefeng 25 and Zhonghuang 13, raw data).

| | | | | | | | |
|---|---|---|---|---|---|---|---|
| Zhonghuang 13 | I | pBSE401 (CK) | 150 | 145 | 90 (60.0) | 216 | 35 |
| | | GmGRF5-GmGIF1 | 150 | 147 | 126 (84.0) | 300 | 68 |
| | II | pBSE401 (CK) | 150 | 141 | 105 (70.0) | 245 | 29 |
| | | GmGRF5-GmGIF1 | 150 | 149 | 122 (81.3) | 342 | 63 |
| | III | pBSE401 (CK) | 150 | 149 | 100 (66.7) | 238 | 33 |
| | | GmGRF5-GmGIF1 | 150 | 144 | 130 (86.7) | 296 | 74 |
| Hefeng 25 | I | pBSE401 (CK) | 150 | 121 | 83 (55.3) | 0 | 0 |
| | | GmGRF5-GmGIF1 | 150 | 132 | 121 (80.7) | 45 | 9 |
| | II | pBSE401 (CK) | 150 | 128 | 84 (56.0) | 0 | 0 |
| | | GmGRF5-GmGIF1 | 150 | 123 | 95 (63.3) | 52 | 15 |
| | III | pBSE401 (CK) | | 123 | 76 (50.7) | 0 | 0 |
| | | GmGRF5-GmGIF1 | | 117 | 104 (69.3) | 67 | 12 |

| Targeted gene | Growth rate (days) | Average elongated shoots per explant | No. transgenic plants/TE (%) | No. mutants/MF (%) | No. transgene-free mutant/TEF (%) |
|---|---|---|---|---|---|
| GmFAD2 (Knockout) | 70 | 1.1 | 12 (8.0) | 10 (6.7) | 0 |
| | 55 | 2.9 | 30 (20.0) | 26 (17.3) | 3 |
| | 68 | 1.0 | 11 (7.3) | 10 (6.7) | 0 |
| | 69 | 1.0 | 13 (8.7) | 11 (7.3) | 0 |
| | 69 | 1.3 | 17 (11.3) | 13 (8.7) | 0 |
| | 66 | 1.2 | 16 (10.7) | 14 (9.3) | 0 |
| | 58 | 3.2 | 36 (24.0) | 37 (24.6) | 7 |
| | 71 | 0.9 | 15 (10.0) | 12 (8.0) | 0 |
| | 71 | 1.1 | 18 (12.0) | 16 (10.7) | 0 |
| | 69 | 1.2 | 14 (9.3) | 12 (8.0) | 0 |
| | 74 | 1.1 | 10 (6.7) | 8 (5.3) | 0 |
| | 60 | 2.9 | 32 (21.3) | 31 (20.6) | 5 |
| | 72 | 1.1 | 11 (7.3) | 10 (6.7) | 0 |
| | 70 | 1.2 | 7 (4.6) | 6 (4.0) | 0 |
| | 70 | 1.2 | 15 (10) | 11 (7.3) | 0 |
| | 89 | 1.7 | 7 (4.7) | 3 (2.0) | 0 |
| | 87 | 2.5 | 24 (16.0) | 22 (14.7) | 2 |
| | 89 | 1.8 | 9 (6.0) | 2 (1.3) | 0 |
| | 87 | 2.7 | 28 (18.7) | 24 (16.0) | 4 |
| | 90 | 1.8 | 8 (5.3) | 6 (4.0) | 0 |
| | 88 | 2.5 | 30 (20.0) | 26 (17.3) | 3 |
| | 1 | 0.0 | 0 | 0 | 0 |
| | 70 | 0.4 | 4 (2.7) | 1 (0.7) | 0 |
| | — | 0.0 | 0 | 0 | 0 |
| | 76 | 0.5 | 4 (2.7) | 2 (1.3) | 1 |
| | 1 | 0.0 | 0 | 0 | 0 |
| | 75 | 0.5 | 3 (2.0) | 3 (2.0) | 0 |

RF (regeneration frequency) = no. of explants with multiple buds/total explant number × 100%.
Growth rates were measured from the date of the initial transformation to the date when the first elongated shoot reached 9 cm in length.
TE (transformation efficiency) = no. of transgenic plants/total explants × 100%.
Elongated shoots (≥9 cm in length) were collected for transgenic assay only once on day 75 after *Agrobacterium*-mediated transformation.
MF (mutation frequency) = no. of mutants/total transgenic plants × 100%. T
FF (transgene-free frequency) = no. of transgene-free mutants/total mutants × 100%.

TABLE 9

Mutation identification using PCR-RE assays for mutants regenerated from Williams 82 explants transformed with pGmGRF5-GmGIF1, pGmGRF6-GmGIF1, pGmGRF11-GmGIF1, pGmGRF18-GmGIF1, and pBSE401, respectively.

| Vector | Mutant ID | Genotype | Mutants ID | Genotype | Mutants ID | Genotype |
|---|---|---|---|---|---|---|
| pGmGRF5-GmGIF1 | Gm-001 | AaBb | Gm-033 | AaBb | Gm-065 | AaBB |
| | Gm-002 | AaBb | Gm-034 | AaBB | Gm-066 | AaBb |
| | Gm-003 | AaBb | Gm-035 | AaBb | Gm-067 | AaBb |
| | Gm-004 | AaBb | Gm-036 | AaBB | Gm-068 | AaBB |
| | Gm-005 | AaBb | Gm-037 | aabb | Gm-069 | AaBb |
| | Gm-006 | AaBb | Gm-038 | AaBb | Gm-070 | aabb |
| | Gm-007 | AaBB | Gm-039 | AaBb | Gm-071 | AaBb |
| | Gm-008 | AaBb | Gm-040 | AaBb | Gm-072 | AaBb |
| | Gm-009 | AaBb | Gm-041 | AaBb | Gm-073 | AaBb |
| | Gm-010 | AaBB | Gm-042 | AaBb | Gm-074 | AaBb |
| | Gm-011 | AaBb | Gm-043 | AaBb | Gm-075 | AaBb |
| | Gm-012 | aabb | Gm-044 | AaBb | Gm-076 | AaBb |
| | Gm-013 | AaBb | Gm-045 | AaBB | Gm-077 | AaBb |
| | Gm-014 | AaBb | Gm-046 | AaBb | Gm-078 | AaBB |
| | Gm-015 | AaBb | Gm-047 | AaBB | Gm-079 | AaBb |

TABLE 9-continued

Mutation identification using PCR-RE assays for mutants
regenerated from Williams 82 explants transformed with pGmGRF5-GmGIF1,
pGmGRF6-GmGIF1, pGmGRF11-GmGIF1, pGmGRF18-GmGIF1, and pBSE401, respectively.

| Vector | Mutant ID | Genotype | Mutants ID | Genotype | Mutants ID | Genotype |
|---|---|---|---|---|---|---|
| | Gm-016 | AaBb | Gm-048 | AABb | Gm-080 | AaBB |
| | Gm-017 | AaBb | Gm-049 | AaBb | Gm-081 | aabb |
| | Gm-018 | AaBb | Gm-050 | AaBb | Gm-082 | AaBB |
| | Gm-019 | AaBb | Gm-051 | AaBb | Gm-083 | AABb |
| | Gm-020 | AaBB | Gm-052 | AaBb | Gm-084 | AaBb |
| | Gm-021 | AaBb | Gm-053 | AaBb | Gm-085 | AaBb |
| | Gm-022 | AaBB | Gm-054 | AaBB | Gm-086 | AaBb |
| | Gm-023 | aabb | Gm-055 | AaBb | Gm-087 | AaBb |
| | Gm-024 | AaBb | Gm-056 | AaBB | Gm-088 | AaBb |
| | Gm-025 | AaBb | Gm-057 | aabb | Gm-089 | AaBB |
| | Gm-026 | AaBb | Gm-058 | AaBb | Gm-090 | AaBb |
| | Gm-027 | AaBb | Gm-059 | AaBb | Gm-091 | AaBb |
| | Gm-028 | AaBb | Gm-060 | AaBb | Gm-092 | AaBB |
| | Gm-029 | AaBB | Gm-061 | AaBb | Gm-093 | AaBb |
| | Gm-030 | AaBb | Gm-062 | AaBb | Gm-094 | AaBb |
| | Gm-031 | AaBB | Gm-063 | AaBb | | |
| | Gm-032 | aabb | Gm-064 | AaBB | | |
| | Gm-101 | AaBb | Gm-112 | AaBb | Gm-123 | AaBB |
| | Gm-102 | AaBB | Gm-113 | AaBb | Gm-124 | aabb |
| | Gm-103 | AaBB | Gm-114 | AaBb | Gm-125 | AaBb |
| | Gm-104 | AaBb | Gm-115 | AaBb | Gm-126 | AaBb |
| pGmGRF6-GmGIF1 | Gm-105 | AaBb | Gm-116 | AaBb | Gm-127 | AaBb |
| | Gm-106 | AaBB | Gm-117 | AaBB | Gm-128 | AaBb |
| | Gm-107 | AaBB | Gm-118 | AaBB | Gm-129 | AaBb |
| | Gm-108 | AaBb | Gm-119 | AaBb | Gm-130 | AaBb |
| | Gm-109 | AaBb | Gm-120 | AaBb | Gm-131 | AaBb |
| | Gm-110 | AaBb | Gm-121 | AaBb | Gm-132 | AaBb |
| | Gm-111 | AaBB | Gm-122 | AaBb | | |
| | Gm-201 | AaBb | Gm-212 | AaBb | Gm-223 | AaBB |
| | Gm-202 | AaBB | Gm-213 | AaBB | Gm-224 | AaBb |
| | Gm-203 | AaBb | Gm-214 | AaBb | Gm-225 | AaBB |
| | Gm-204 | AaBB | Gm-215 | AaBB | Gm-226 | AaBb |
| | Gm-205 | AaBB | Gm-216 | AaBB | Gm-227 | AaBb |
| | Gm-206 | AaBb | Gm-217 | AaBb | Gm-228 | AaBb |
| | Gm-207 | AaBb | Gm-218 | AaBb | Gm-229 | AaBb |
| | Gm-208 | AaBb | Gm-219 | AaBb | Gm-230 | AaBb |
| | Gm-209 | AaBb | Gm-220 | AaBb | Gm-231 | AaBb |
| | Gm-210 | AaBb | Gm-221 | AaBb | Gm-232 | AaBb |
| pGmGRF11-GmGIF1 | Gm-211 | AaBB | Gm-222 | AaBb | Gm-233 | AaBb |
| pGmGRF18-GmGIF1 | Gm-301 | AaBb | Gm-313 | AaBb | Gm-325 | AaBb |
| | Gm-302 | AaBb | Gm-314 | AaBb | Gm-326 | AaBB |
| | Gm-303 | AaBB | Gm-315 | AaBb | Gm-327 | AaBb |
| | Gm-304 | AaBb | Gm-316 | AaBb | Gm-328 | AaBb |
| | Gm-305 | AaBB | Gm-317 | AaBB | Gm-329 | AaBb |
| | Gm-306 | AaBB | Gm-318 | AaBb | Gm-330 | AaBb |
| | Gm-307 | AaBb | Gm-319 | AaBB | Gm-331 | AaBb |
| | Gm-308 | AaBb | Gm-320 | AaBB | Gm-332 | AaBB |
| | Gm-309 | AaBb | Gm-321 | AaBB | Gm-333 | AaBb |
| | Gm-310 | AaBb | Gm-322 | AaBb | Gm-334 | AaBB |
| | Gm-311 | AABb | Gm-323 | AaBB | Gm-335 | AABb |
| | Gm-312 | AaBb | Gm-324 | AaBB | Gm-336 | AaBb |
| pBSE401 (CK) | Gm-401 | AaBb | Gm-413 | AaBB | Gm-425 | AaBb |
| | Gm-402 | AaBb | Gm-414 | AaBb | Gm-426 | AaBb |
| | Gm-403 | AaBb | Gm-415 | AaBB | Gm-427 | AaBb |
| | Gm-404 | AaBb | Gm-416 | AaBB | Gm-428 | AaBb |
| | Gm-405 | AABb | Gm-417 | AaBb | Gm-429 | AaBb |
| | Gm-406 | AaBb | Gm-418 | AaBb | Gm-430 | AaBB |
| | Gm-407 | AaBb | Gm-419 | AaBb | Gm-431 | AaBb |
| | Gm-408 | AaBb | Gm-420 | AaBb | Gm-432 | AaBB |
| | Gm-409 | AaBb | Gm-421 | AaBb | | |
| | Gm-410 | AaBb | Gm-422 | AaBb | | |
| | Gm-411 | AABb | Gm-423 | AaBB | | |
| | Gm-412 | AaBb | Gm-424 | AaBb | | |

Aa/aa and Bb/bb represent heterozygous/homozygous mutations in FAD2-1A and FAD2-1B, respectively.

TABLE 10

Mutation identification using PCR-RE assays for mutants regenerated from explants (Zhonghuang 13 and Hefeng 25) transformed with pGmGRF5-GmGIF and pBSE401.

| Soybean cultivar | Vector | Mutant ID | Genotype | Mutant ID | Genotype | Mutant ID | Genotype |
|---|---|---|---|---|---|---|---|
| Hefeng 25 | pGmGRF5-GmGIF | Gm-501 | AaBb | Gm-503 | AaBB | Gm-505 | AaBB |
|  |  | Gm-502 | AaBB | Gm-504 | AaBb | Gm-506 | AaBb |
| Zhonghuang 13 | pGmGRF5-GmGIF1 | Gm-601 | AaBB | Gm-625 | AaBb | Gm-649 | AaBb |
|  |  | Gm-602 | AaBb | Gm-626 | AaBb | Gm-650 | AaBB |
|  |  | Gm-603 | AaBb | Gm-627 | AaBb | Gm-651 | AaBb |
|  |  | Gm-604 | AaBb | Gm-628 | AaBB | Gm-652 | AaBB |
|  |  | Gm-605 | AaBB | Gm-629 | AaBB | Gm-653 | AaBB |
|  |  | Gm-606 | AaBb | Gm-630 | AaBB | Gm-654 | AaBb |
|  |  | Gm-607 | AaBB | Gm-631 | AaBb | Gm-655 | AaBb |
|  |  | Gm-608 | AaBB | Gm-632 | AaBb | Gm-656 | AaBb |
|  |  | Gm-609 | AaBb | Gm-633 | AaBb | Gm-657 | AaBb |
|  |  | Gm-610 | AaBb | Gm-634 | AaBb | Gm-658 | AaBb |
|  |  | Gm-611 | AaBb | Gm-635 | AaBb | Gm-659 | AaBB |
|  |  | Gm-612 | AaBb | Gm-636 | AaBb | Gm-660 | AaBb |
|  |  | Gm-613 | AaBb | Gm-637 | AaBb | Gm-661 | AaBB |
|  |  | Gm-614 | AaBB | Gm-638 | AaBb | Gm-662 | AaBB |
|  |  | Gm-615 | AaBb | Gm-639 | AaBB | Gm-663 | AaBb |
|  |  | Gm-616 | AaBB | Gm-640 | AaBB | Gm-664 | AaBb |
|  |  | Gm-617 | AaBB | Gm-641 | AaBb | Gm-665 | AaBb |
|  |  | Gm-618 | AaBb | Gm-642 | AaBb | Gm-666 | AaBb |
|  |  | Gm-619 | AaBb | Gm-643 | AaBb | Gm-667 | AaBb |
|  |  | Gm-620 | AaBb | Gm-644 | AaBb | Gm-668 | AaBB |
|  |  | Gm-621 | AaBb | Gm-645 | AaBb | Gm-669 | AaBb |
|  |  | Gm-622 | AaBb | Gm-646 | AaBB | Gm-670 | AaBB |
|  |  | Gm-623 | AaBB | Gm-647 | AaBb | Gm-671 | AaBB |
| pBSE401 |  | Gm-624 | AaBb | Gm-648 | AaBB | Gm-672 | AaBb |
|  |  | Gm701 | AaBb | Gm705 | AaBb | Gm709 | AaBb |
|  |  | Gm702 | AaBb | Gm706 | AaBb | Gm710 | AaBB |
|  |  | Gm703 | AaBB | Gm707 | AaBb | Gm711 | AaBb |
|  |  | Gm704 | AaBb | Gm708 | AaBb |  |  |

Aa/aa and Bb/bb represent heterozygous/homozygous mutations in FAD2-1A and FAD2-1B, respectively.

TABLE 11

Effect of the TaGRF4-TaGIF1 and mTaGRF4-TaGIF1 complexes on regeneration and genome editing efficiencies of common wheat cultivars Bobwhite and Kenong 199.

| Targeted gene | Common wheat cultivar | Treatment | No. bombarded immature embryos | No. regenerated plants/ RF (%) | No. mutants/ MF (%) | No. transgene-free mutants/ TFF (%) |
|---|---|---|---|---|---|---|
| TaALS (C to T) | Bobwhite | pUBI-GFP (CK) | 333 | 266 (81.0 ± 19.8) | 33 (9.9 ± 1.3) | 17 (50.9 ± 5.5) |
|  |  | TaGRF4-TaGIF1 | 277 | 1507 (508.0 ±75.9) | 100 (32.7 ± 3.45) | 47 (47.1 ± 5.9) |
|  |  | mTaGRF4-TaGIF1 | 343 | 2080 (630.1 ± 86.2) | 216 (63.3 ± 4.0) | 103 (47.5 ± 2.6) |
|  | Kenong 199 | pUBI-GFP (CK) | 307 | 419 (136.9 ± 5.7) | 55 (17.7 ± 2.6) | 28 (52.8 ± 8.4) |
|  |  | TaGRF4-TaGIF1 | 325 | 2095 (654.5 ± 55.5) | 331 (103.4 ± 9.3) | 170 (51.6 ± 1.8) |
|  |  | mTaGRF4-TaGIF1 | 328 | 3796 (1165.4 ± 58.8) | 577 (176.1 ± 13.9) | 324 (55.4 ± 6.6) |

RF (regeneration frequency) = no. of regenerated plants/total immature embryos × 100%.
MF (mutation frequency) = no. of mutants/total immature embryos × 100%.
The numbers and means for each treatment were calculated from data collected from three replicates of the experiment.
Data are means ± s.e.m (n = 3).

TABLE 12

Effect of the TaGRF4-TaGIF1 and mTaGRF4-TaGIF1 complexes on regeneration and genome editing efficiencies of common wheat cultivars Bobwhite and Kenong 199 (raw data).

| Targeted gene | Common wheat cultivar | Treatment | Repeat | No. bombarded immature embryos | No. regenerated plants/RF (%) | No. mutants/MF (%) | No. transgene-free mutants/ TFF (%) |
|---|---|---|---|---|---|---|---|
| TaALS (C to T) | Bobwhite | pUBI-GFP (CK) | 1 | 119 | 50 (42.0) | 10 (8.4) | 4 (40.0) |
|  |  |  | 2 | 112 | 119 (106.2) | 14 (12.5) | 8 (57.1) |
|  |  |  | 3 | 102 | 97 (95.0) | 9 (8.8) | 5 (55.6) |

TABLE 12-continued

Effect of the TaGRF4-TaGIF1 and mTaGRF4-TaGIF1 complexes on regeneration and genome editing efficiencies of common wheat cultivars Bobwhite and Kenong 199 (raw data).

| Targeted gene | Common wheat cultivar | Treatment | Repeat | No. bombarded immature embryos | No. regenerated plants/RF (%) | No. mutants/MF (%) | No. transgene-free mutants/TFF (%) |
|---|---|---|---|---|---|---|---|
| | | TaGRF4-TaGIF1 | 1 | 116 | 547 (472.6) | 42 (25.9) | 20 (47.6) |
| | | | 2 | 86 | 562 (653.5) | 30 (34.9) | 11 (36.7) |
| | | | 3 | 75 | 398 (530.7) | 28 (37.3) | 16 (57.1) |
| | | mTaGRF4-TaGIF1 | 1 | 103 | 498 (483.5) | 70 (68.0) | 32 (45.7) |
| | | | 2 | 117 | 915 (782.1) | 78 (66.7) | 41 (52.6) |
| | | | 3 | 123 | 767 (624.6) | 68 (55.3) | 30 (44.2) |
| | Kenong 199 | pUBI-GFP (CK) | 1 | 102 | 146 (143.1) | 17 (16.7) | 7 (41.2) |
| | | | 2 | 110 | 138 (125.5) | 25 (22.7) | 12 (48.0) |
| | | | 3 | 95 | 135 (142.1) | 13 (13.7) | 9 (69.2) |
| | | TaGRF4-TaGIF1 | 1 | 132 | 763 (578.0) | 116 (87.9) | 56 (48.3) |
| | | | 2 | 100 | 623 (623.0) | 120 (120) | 62 (51.7) |
| | | | 3 | 93 | 709 (762.4) | 95 (102.2) | 52 (54.7) |
| | | mTaGRF4-TaGIF1 | 1 | 114 | 1329 (1165.8) | 230 (201.8) | 135 (58.7) |
| | | | 2 | 120 | 1276 (1063.3) | 185 (154.2) | 120 (64.9) |
| | | | 3 | 94 | 1191 (1267.0) | 162 (172.3) | 69 (42.6) |

RF (regeneration frequency) = no. of regenerated plants/total immature embryos × 100%.
MF (mutation frequency) = no. of mutants/total immature embryos × 100%.

TABLE 13

Effect of mTaGRF4-TaGIF1 on regeneration and genome editing efficiencies of nine elite common wheat cultivars.

| Targeted gene | Common wheat cultivar | Treatment | No. bombarded embryos | No. regenerated plants/ RF (%) | No. mutants/ MF (%) | No. homozygous mutants/HMF (%) | No. transgene-free mutants/ TFF (%) |
|---|---|---|---|---|---|---|---|
| TaALS (C-to-T) | Jimai 20 | UBI-GFP (CK) | 335 | 14 (4.2 ± 1.1) | 0 | 0 | 0 |
| | Jimai 22 | mTaGRF4-TaGIF1 | 270 | 37 (14.2 ± 2.1) | 9 (3.3) | 5 (55.6) | 2 (22.2) |
| | Jing 411 | UBI-GFP (CK) | 272 | 13 (4.7 ± 0.6) | 0 | 0 | 0 |
| | Shannong 20 | mTaGRF4-TaGIF1 | 344 | 34 (9.9 ± 0.4) | 4 (1.2) | 0 | 1 (25.0) |
| | Shannong 116 | UBI-GFP (CK) | 203 | 65 (18.8 ± 2.7) | 2 (1.0) | 0 | 0 |
| | Xiaoyan 54 | mTaGRF4-TaGIF1 | 320 | 135 (34.0 ± 3.2) | 5 (1.6) | 1 (25.0) | 2 (50.0) |
| | Zhoumai 27 | UBI-GFP (CK) | 335 | 15 (4.5 ± 0.6) | 0 | 0 | 0 |
| | Zhoumai 28 | pmTaGRF4-TaGIF1 | 344 | 71 (20.7 ± 2.2) | 10 (2.9) | 1 (10.0) | 5 (50.0) |
| | Zhongmai 175 | UBI-GFP (CK) | 285 | 128 (66.3 ± 8.2) | 3 (1.1) | 0 | 1 (33.3) |
| | | mTaGRF4-TaGIF1 | 308 | 342 (101.7 ± 18.4) | 7 (2.3) | 1 (14.3) | 2 (28.6) |
| | | UBI-GFP (CK) | 320 | 0 | 0 | 0 | 0 |
| | | mTaGRF4-TaGIF1 | 343 | 36 (11.0 ± 2.1) | 6 (1.7) | 1 (16.7) | 3 (50.0) |
| | | UBI-GFP (CK) | 286 | 441 (157.6 ± 24.1) | 4 (1.4) | 0 (0.0) | 1 (25.0) |
| | | mTaGRF4-TaGIF1 | 343 | 1578 (440.8 ± 50.3) | 8 (2.3) | 1 (12.5) | 5 (62.5) |
| | | UBI-GFP (CK) | 308 | 16 (5.2 ± 1.3) | 0 | 0 | 0 |
| | | mTaGRF4-TaGIF1 | 331 | 370 (112.3 ± 11.4) | 10 (3.0) | 2 (20.0) | 4 (40.0) |
| | | UBI-GFP (CK) | 335 | 614 (187. ± 26.1) | 13 (3.9) | 2 (15.4) | 8 (61.6) |
| | | mTaGRF4-TaGIF1 | 332 | 1265 (380.6 ± 29.0) | 27 (8.1) | 10 (37.0) | 18 (66.7) |

RF (regeneration frequency) = no. of regenerated plants/total embryos × 100%.
MF (mutation frequency) = no. of mutants/total immature embryos × 100%.
HMF (homozygous mutant frequency) = no. of homozygous mutants/total mutants × 100%.
TFF (transgene-free frequency) = no. of transgene-free mutants/total mutants × 100%.
The numbers and means for each treatment were calculated from data collected from three replicates of the experiment.
Data are means ± s.e.m (n = 3).

TABLE 14

Effect of expression of the mutated common wheat TaGRF4-TaGIF1 on the regeneration and genome editing efficiencies of nine elite common wheat cultivars (raw data).

| Common wheat cultivar | Treatment | Repeat | No. bombarded immature embryos | No. regenerated plants/RF (%) |
|---|---|---|---|---|
| Jimai 20 | pUBI-GFP (CK) | 1 | 115 | 4 (3.5) |
| | | 2 | 110 | 7 (6.4) |
| | | 3 | 110 | 3 (2.7) |
| | mTaGRF4-TaGIF1 | 1 | 109 | 11 (10.1) |
| | | 2 | 91 | 14 (15.4) |
| | | 3 | 70 | 12 (17.1) |

TABLE 14-continued

Effect of expression of the mutated common wheat TaGRF4-TaGIF1 on the regeneration and genome editing efficiencies of nine elite common wheat cultivars (raw data).

| Common wheat cultivar | Treatment | Repeat | No. bombarded immature embryos | No. regenerated plants/RF (%) |
|---|---|---|---|---|
| Jimai 22 | pUBI-GFP (CK) | 1 | 102 | 6 (5.9) |
| | | 2 | 66 | 3 (4.5) |
| | | 3 | 104 | 4 (3.8) |
| | mTaGRF4-TaGIF1 | 1 | 118 | 11 (9.3) |
| | | 2 | 123 | 13 (10.6) |
| | | 3 | 103 | 10 (9.7) |
| Jing 411 | pUBI-GFP (CK) | 1 | 115 | 20 (17.4) |
| | | 2 | 116 | 28 (24.1) |
| | | 3 | 113 | 17 (15.0) |
| | mTaGRF4-TaGIF1 | 1 | 130 | 40 (30.8) |
| | | 2 | 140 | 43 (30.7) |
| | | 3 | 128 | 52 (40.6) |
| Shangnong 20 | pUBI-GFP (CK) | 1 | 114 | 5 (4.4) |
| | | 2 | 115 | 4 (3.5) |
| | | 3 | 106 | 6 (5.7) |
| | mTaGRF4-TaGIF1 | 1 | 115 | 19 (16.5) |
| | | 2 | 116 | 25 (21.6) |
| | | 3 | 113 | 27 (23.9) |
| Shangnong 116 | pUBI-GFP (CK) | 1 | 60 | 49 (81.7) |
| | | 2 | 75 | 40 (53.3) |
| | | 3 | 61 | 39 (63.9) |
| | mTaGRF4-TaGIF1 | 1 | 133 | 124 (93.2) |
| | | 2 | 90 | 110 (122.2) |
| | | 3 | 85 | 108 (127.1) |
| Xiaoyan 54 | pUBI-GFP (CK) | 1 | 98 | 0 |
| | | 2 | 108 | 0 |
| | | 3 | 114 | 0 |
| | mTaGRF4-TaGIF1 | 1 | 98 | 10 (10.2) |
| | | 2 | 100 | 15 (15.0) |
| | | 3 | 141 | 11 (7.8) |
| Zhoumai 27 | pUBI-GFP (CK) | 1 | 81 | 160 (197.5) |
| | | 2 | 105 | 120 (114.3) |
| | | 3 | 100 | 161 (161.0) |
| | mTaGRF4-TaGIF1 | 1 | 109 | 500 (458.7) |
| | | 2 | 132 | 457 (346.2) |
| | | 3 | 120 | 621 (517.5) |
| Zhoumai 28 | pUBI-GFP (CK) | 1 | 115 | 8 (7.0) |
| | | 2 | 86 | 5 (5.9) |
| | | 3 | 107 | 3 (2.8) |
| | mTaGRF4-TaGIF1 | 1 | 129 | 130 (100.8) |
| | | 2 | 105 | 142 (135.2) |
| | | 3 | 97 | 98 (101.0) |
| Zhongmai 175 | pUBI-GFP (CK) | 1 | 95 | 198 (208.2) |
| | | 2 | 110 | 240 (218.2) |
| | | 3 | 130 | 176 (135.4) |
| | mTaGRF4-TaGIF1 | 1 | 120 | 389 (324.2) |
| | | 2 | 107 | 450 (420.6) |
| | | 3 | 105 | 417 (397.1) |

RF (regeneration frequency) = no. of regenerated plants/total immature embryos × 100%.

TABLE 15

Genotypes of the T0 taals mutants regenerated from immature embryos of nine elite common wheat cultivars treated with mTaGRF4-TaGIF1 and UBI-GFP (CK), respectively.

| Wheat cultivar | Vectors delivered | Mutant ID | Genotype | A subgenome | B subgenome | D subgenome | Transgene-free |
|---|---|---|---|---|---|---|---|
| Zhongmai 175 | pmTaGRF4-TaGIF1 + pUBI-A3A | Ta-001 | AaBbDd | $C_6C_7C_8C_9C_{10} > T_6T_7T_8T_{10}$ | $C_6C_7C_8C_9C_{10} > T_6T_7T_8T_{10}$; $C_6C_7 > T_6T_7$ | $C_6C_7C_8C_9C_{10} > T_6T_7T_8T_9T_{10}$ | YES |
| | | Ta-002 | aabbdd | $C_6C_7C_8C_9C_{10} > T_6T_7T_8T_9$ | $C_6C_7C_8C_9C_{10} > T_6T_7T_8T_9T_{10}$ | $C_6C_7C_8 > T_6T_7T_8$ | YES |
| | | Ta-003 | AaBbdd | $C_6C_7C_8C9C_{10} > T_6T_7T_8T_9T_{10}$ | $C_6C_7C_8C_9C_{10} > T_6T_7T_8T_9T_{10}$ | $C_6C_7C_8C_9C_{10} > T_6T_7T_8T_9T_{10}$ | NO |
| | | Ta-004 | aabbdd | $C_6C_7C_8C9C_{10} > T_6T_7T_8T_9T_{10}$ | $C_6C_7 > T_6T_7$; | Del CCCCGCC; Del CGCC | YES |
| | | Ta-005 | aabbdd | $C_6C_7C_8 > T_6T_7T_8$ | $C_6C_7C_8C_9C_{10} > T_6T_7T_8T_{10}$ | $C_6C_7C_8 > T_6T_7T_8$; $C_6C_7C_8C_9C_{10} > T_6T_7T_8T_9T_{10}$ | YES |
| | | Ta-006 | AaBbDD | $C_6C_7C_8C_9C_{10} > T_6T_7T_8T_{10}$ | $C_6C_7C_8C_9C_{10} > T_6T_7T_8T_{10}$ | WT | YES |
| | | Ta-007 | aabbdd | $C_6C_7C_8C_9C_{10} > T_6T_7T_8T_{10}$ | $C_6C_7C_8C_9C_{10} > T_6T_7T_8T_{10}$ | $C_6C_7 > T_6T_7$ | YES |
| | | Ta-008 | AaBBDD | WT | WT | WT | NO |
| | | Ta-009 | aabbdd | $C_6C_7C_8C_9C_{10} > T_6T_7T_8T_9$ | $C_6C_7C_8 > T_6T_7T_8$ | | YES |
| | | Ta-010 | aabbDd | $C_6C_7C_8 > T_6T_7T_8$ | $C_6C_7C_8C_9C_{10} > T_6T_7T_8T_{10}$ | $C_6C_7 > T_6T_7$ | YES |
| | | Ta-011 | AaBbDD | AGGTCCCCCGCCGC > GCCCC | TCACGGGCCAGGTCCCC > ATCCTGTTTCGGGCCAGGT | WT | NO |
| | | Ta-012 | AaBbDD | Del AGGTCCCCC; WT | CCCCC > TGTTT---------; | WT | YES |
| | | Ta-013 | aabbdd | $C_6C_7C_8C_9 > T_6T_7T_8T_9$ | $C_6C_7C_8 > T_6T_7T_8$ | $C_6C_7C_8C_9C_{10} > T_6T_7T_8T_9T_{10}$ | NO |
| | | Ta-014 | AaBbdd | $C_6C_7C_8C_9C_{10} > T_6T_7T_8T_9T_{10}$ | $C_6C_7C_8 > T_6T_7T_8$ | $C_6C_7C_8C_9C_{10} > T_6T_7T_8T_9$ | YES |
| | | Ta-015 | AaBBDD | WT | WT | WT | NO |
| | | Ta-016 | AAbbDD | $C_6C_7C_8C_9C_{10} > T_6T_7T_8T_9T_{10}$ | $C_6C_7C_8 > T_6T_7T_8$ | WT | NO |
| | | Ta-017 | aaBbdd | WT | $C_6C_7C_8C_9C_{10} > T_6T_7T_8T_{10}$; $C_6C_7C_8 > T_6T_7T_8$ | $C_6C_7C_8C_9C_{10} > T_6T_7T_8T_{10}$ | YES |
| | | Ta-018 | aabbdd | $C_6C_7C_8C_9C_{10} > T_6T_7T_8T_{10}$; $C_9 > G_9$ | $C_6C_7C_8 > T_6T_7T_8$; $C_6C_7C_8C_9C_{10} > T_6T_7T_8T_{10}$ | $C_7C_9C_{10} > T_7T_9T_{10}$ | YES |
| | | Ta-019 | aabbdd | $C_6C_7C_8C_9C_{10} > T_6T_7T_8T_9$ | $C_6C_7C_8 > T_6T_7T_8$ | $C_7C_9C_{10} > T_7T_9T_{10}$ | YES |
| | | Ta-020 | AaBbDd | $C_6C_7C_8C_9C_{10} > T_6T_7T_8T_{10}$ | $C_6C_7C_8 > T_6T_7G_8$; $C_7C_9C_{10} > G_7T_9T_{10}$ | $C_6C_7C_8C_9C_{10} > T_6T_7T_8T_9G_{10}$; | NO |
| | | Ta-021 | aabbDd | Del CCCCCGCCGCATCATC; WT | $C_6C_7 > T_6T_7$; WT | $C_6C_7C_8C_9C_{10} > T_6T_7T_8T_9T_{10}$ | YES |
| | | Ta-022 | aaBBDd | $C_6C_7C_8C_{10} > T_6T_7T_8T_{10}$ | WT | Del CCGCCGCA | YES |
| | | Ta-023 | aabbdd | $C_6C_7C_8C_9C_{10} > T_6T_7T_8T_{10}$ | $C_6C_7C_8C_9C_{10} > T_6T_7T_8T_{10}$ | $C_6C_7C_8C_9C_{10} > T_6T_7T_8T_9T_{10}$ | YES |
| | | Ta-024 | AaBbdd | $C_6C_7C_8C_9C_{10} > T_6T_7T_8T_9T_{10}$ | $C_6C_7C_8 > T_6T_7T_8$ | $C_6C_7C_8C_9 > T_6T_7T_8T_9$ | YES |
| | | Ta-025 | AabbDd | $C_6C_7C_8C_9 > T_6T_7T_8T_9$ | $C_6C_7C_8C_9C_{10} > T_6G_7T_8G_9T_{10}$ | $C_6C_7C_8C_9C_{10} > T_6T_7T_8T_9T_{10}$ | NO |
| | | Ta-026 | aabbdd | $C_6C_7C_8 > T_6T_7A_8$ | $C_6C_7C_8C_9C_{10} > T_6T_7T_8T_9$ | $C_6C_7C_8 > T_6T_7T_8$; $C_6 > T_6$ | YES |
| | | Ta-027 | aaBbDD | $C_6C_7C_8C_9C_{10} > T_6T_7T_8T_9T_{10}$ | $C_6C_7C_8 > T_6T_7T_8$; | WT | NO |
| | pUBI-GFP + pUBI-A3A | Ta-051 | AaBbdd | $C_6C_7C_8C_9C_{10} > T_6T_7T_8T_9T_{10}$ | $C_6C_7C_8C_9 > T_6T_7C_9$ | $C_6C_7C_8C_9C_{10} > T_6T_7T_8T_9T_{10}$; $C_6C_7C_8C_9 > T_6T_7T_8T_9$ | NO |
| | | Ta-052 | aabbdd | $C_6C_7C_8C_9C_{10} > T_6T_7T_8$ | $C_6C_7C_8 > T_6T_7T_8$ | $C_6C_7C_8C_9C_{10} > T_6T_7T_8T_9T_{10}$ | NO |

TABLE 15-continued

Genotypes of the T0 taals mutants regenerated from immature embryos of nine elite common wheat cultivars treated with mTaGRF4-TaGIF1 and UBI-GFP (CK), respectively.

| Wheat cultivar | Vectors delivered | Mutant ID | Genotype | A subgenome | B subgenome | D subgenome | Transgene-free |
|---|---|---|---|---|---|---|---|
| | | Ia-053 | AaBbdd | $C_6 > T_6$ | $C_6C_7C_8C_9C_{10} > T_6T_7T_8T_9$- | $C_6C_7C_8C_9 > T_6T_7T_8T_9$ | YES |
| | | | | $C_6C_7C_8C_9C_{10} > T_6T_7T_8T_9T_{10}$ | $C_6C_7C_8C_9 > T_6T_7T_8T_9$ | $C_6C_7C_8C_9 > T_6T_7T_8T_9T_{10}$; | |
| | | Ia-054 | AaBbdd | $C_6C_7C_8C_9C_{10} > T_6T_7T_8T_9T_{10}$ | $C_6C_7C_8C_9 > T_6T_7T_8T_9$ | $C_6C_7C_8C_9 > T_6T_7T_8T_9$ | NO |
| | | Ia-055 | AaBbdd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8C_9 > T_6T_7T_8T_9T_{10}$ | NO |
| | | Ia-056 | AaBbDD | $T_5C_6C_7C_8 > -G_6T_7T_8$ | $C_6C_7C_8C_9C_{10} > T_6T_7T_8T_9T_{10}$ | $C_6C_7C_8C_9 > T_6T_7T_8T_9T_{10}$ | YES |
| | | Ia-057 | AABBDd | WT | WT | WT | NO |
| | | Ia-058 | aabbdd | $C_6C_7C_8C_9C_{10} > T_6T_7T_8T_9$ | $C_6C_7C_8 > T_6T_7T_8$ | $C_6C_7C_8 > T_6T_7T_8$ | YES |
| | | Ia-059 | AaBbDd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8C_9 > T_6T_7T_8T_9T_{10}$; | YES |
| | | Ia-060 | AABBDD | $C_6C_7C_8C_9C_{10} > T_6T_7T_8T_9T_{10}$ | WT | WT | YES |
| | | Ia-061 | Aabbdd | $C_6C_7C_8 > T_6T_7T_8$ | $C_6C_7C_8C_9 > T_6T_7T_8T_9$ | $C_6C_7C_8C_9 > T_6T_7T_8T_9T_{10}$ | YES |
| | | Ia-062 | Aabbdd | $C_6C_7C_8 > T_6T_7T_8$ | $C_6C_7C_8 > T_6T_7T_8$ | $C_6C_7C_8 > T_6T_7T_8$ | YES |
| | | Ia-063 | AABbDd | WT | $C_6C_7C_8C_9 > T_6T_7T_8T_9$ | $C_6C_7C_8 > T_6T_7T_8$ | YES |
| | | Ia-101 | aabbdd | $C_6C_7C_8C_9C_{10} > T_6T_7T_8T_9T_{10}$ | $C_6C_7C_8C_9C_{10} > T_6T_7T_8T_9T_{10}$ | $C_6 > T_6$ | NO |
| | | Ia-102 | aabbdd | $C_6C_7C_8 > T_6T_7T_8$ | $C_6C_7C_8 > T_6T_7T_8$ | $C_6C_7C_8C_9 > T_6T_7T_8T_9T_{10}$ | YES |
| | | Ia-103 | AABBDD | WT | $C_6C_7C_8C_9C_{10} > G_6T_7T_8T_9T_{10}$ | $C_{10} > T_{10}$ | NO |
| | | Ia-104 | aaBbDd | $C_{10} > T_{10}$ | $C_6C_7C_8C_9C_{10} > G_6T_7T_8T_9T_{10}$ | $C_{10+} > T^{10}$ | NO |
| Jimai 20 | pmTaGRF4-TaGIF1 + pUBI-A3A | Ia-105 | aaBbDd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8C_9 > T_6T_7T_8T_9T_{10}$ | YES |
| | | Ia-106 | aabbdd | $C_6C_7C_8C_9 > T_6T_7A_8$ | $C_6C_7C_8C_9 > T_6T_7T_8T_9$ | $C_6C_7C_8C_9 > T_6T_7T_8T_9$ | NO |
| | | Ia-107 | aabbdd | $C_6C_7C_8 > T_6T_7T_8$ | $C_6C_7C_8 > T_6T_7T_8$ | $C_6C_7C_8C_9 > T_6T_7T_8T_9$ | NO |
| | | Ia-108 | AaBbDd | $C_6C_7C_8C_9C_{10} > T_6T_7T_8T_9T_{10}$ | $C_6C_7C_8C_9 > T_6T_7T_8T_9$ | $C_6C_7C_8C_9 > T_6T_7T_8T_9T_{10}$ | NO |
| | | Ia-109 | aabbdd | $C_6C_7C_8C_9 > T_6T_7T_8T_9$ | $C_6C_7C_8 > T_6T_7T_8$ | $C_6C_7C_8 > T_6T_7T_8$ | NO |
| Shannong 20 | pmTaGRF4-TaGIF1 + pUBI-A3A | Ia-151 | aabbdd | $C_6C_7C_8C_9C_{10} > T_6T_7T_8T_9T_{10}$ | $C_6C_7C_8C_9C_{10}C_{12}C_{13} > T_6T_7A_8T_9T_{10}T_{12}T_{13}$; | $C_6C_7C_8C_9C_{10} > T_6T_7T_8T_9T_{10}$ | YES |
| | | | | | $C_6C_7C_8 > T_6A_7A_8$ | | |
| | | Ia-152 | AaBbDd | $C_6C_7C_8C_9C_{10} > T_6T_7T_8T_9T_{10}$ | $C_6C_7C_8 > T_6A_7A_8$ | $C_6C_7C_8C_9C_{10} > T_6T_7T_8T_9T_{10}$ | NO |
| | | Ia-153 | Aabbdd | $C_6C_7C_8C_9C_{10} > T_6T_7A_8T_9T_{10}$ | $C_6C_7C_8 > T_6T_7T_8$ | $C_6C_7C_8C_9C_{10} > T_6T_7T_8T_9T_{10}$ | YES |
| | | Ia-154 | AaBbDd | $C_6C_7C_8C_9C_{10} > T_6T_7T_8T_9T_{10}$ | $C_6C_7C_8 > T_6T_7T_8$ | $C_6C_7C_8C_9C_{10} > T_6T_7T_8T_9T_{10}$ | YES |
| | | Ia-155 | AaBbDD | Del CCCCCGCCGCA | $C_6C_7C_8C_9 > T_6T_7T_8T_9$ | WT | YES |
| | | Ia-156 | AaBbdd | $C_6C_7C_8 > T_6T_7T_8$ | $C_6C_7C_8C_9C_{10} > T_6T_7T_8T_9T_{10}$ | $C_9C_{10} > G_9T_{10}$; | YES |
| | | | | | | AGGTCCCCCGCCGCAT | |
| | | Ia-157 | AaBbdd | $C_6C_7C_8C_9 > T_6T_7T_8T_9$ | $C_6C_7C_8C_9C_{10} > T_6T_7T_8T_9T_{10}$ | GA > CCGCTTTTC------- | NO |

TABLE 15-continued

Genotypes of the T0 taals mutants regenerated from immature embryos of nine elite common wheat cultivars treated with mTaGRF4-TaGIF1 and UBI-GFP (CK), respectively.

| Wheat cultivar | Vectors delivered | Mutant ID | Genotype | A subgenome | B subgenome | D subgenome | Transgene-free |
|---|---|---|---|---|---|---|---|
| | | Ta-158 | AaBbDd | $C_6C_7C_8C_9C_{10} > T_6T_7T_8$ | $C_6C_7C_8 > T_6T_7T_8$ | $C_6C_7C_8 > T_6T_7-G_8$ | NO |
| | | Ta-159 | aaBbDd | $C_6C_7C_8 > T_6T_7T_8$ | $C_6C_7 > T_6T_7$ | $C_6C_7C_8C_9 > T_6T_7T_8T_9$ | NO |
| | | Ta-160 | AaBbdd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8C_9 > T_6T_7T_8T_9$ | NO |
| Jimai 22 | pmTaGRF4-TaGIF1 + pUBI-A3A | Ta-171 | AaBbDd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8C_9C_{10} > T_6T_7T_8T_9T_{10}$ | NO |
| | | Ta-172 | AaBbDd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8C_9C_{10} > T_6T_7T_8T_9T_{10};$ | YES |
| | | Ta-173 | AaBBDd | $C_6C_7C_8C_9C_{10} > T_6T_7T_8T_9T_{10}$ | WT | $C_6C_7C_8C_9C_{10} > T_6T_7T_8T_9T_{10}$ | NO |
| | | Ta-174 | AaBbDD | $C_6C_7C_8 > T_6T_7T_8$ | $C_6C_7C_8 > T_6T_7T_8$ | WT | NO |
| | pUBI-GFP + pUBI-A3A | Ta-211 | AaBbDd | $C_6C_7C_8C_9C_{10} > T_6T_7T_8T_9A_{10}$ | $C_6C_7C_8C_9C_{10} > T_6T_7T_8T_9A_{10}$ | $C_6C_7C_8C_9C_{10} > T_6T_7T_8T_9A_{10}$ | NO |
| | | Ta-212 | AABbDD | WT | $C_6C_7C_8 > T_6T_7T_8$ | $C_6C_7C_8C_9C_{10} > T_6T_7T_8T_9T_{10}$ | YES |
| | | Ta-213 | AaBbDd | $C_6C_7C_8C_9C_{10} > T_6T_7T_8T_9A_{10}$ | $C_6C_7C_8 > T_6T_7T_8;$ | $C_6C_7C_8 > T_6T_7T_8$ | NO |
| Shannong 116 | pmTaGRF4-TaGIF1 + pUBI-A3A | Ta-201 | AaBbDd | CCCCGCCGCAT > TTTTGCCGCTC | CCCCCGCCGCAT > ATTCCCCACGA | $C_6C_7C_8C_9C_{10} > T_6T_7T_8T_9T_{10}$ | YES |
| | | Ta-202 | aabbdd | $C_6C_7C_8C_9C_{10} > T_6T_7T_8T_9T_{10}$ | Del GTCCCCCGCCGCAT GATCGGCACGG | $C_6C_7C_8C_9 > T_6T_7T_8T_9$ | YES |
| | | Ta-203 | AaBbDd | WT | $C_6C_7C_8C_9C_{10} > T_6T_7T_8T_9T_{10}$ | $C_6C_7C_8C_9 > T_6T_7T_8T_9$ | NO |
| | | Ta-204 | AAbbdd | WT | $C_6C_7C_8 > T_6T_7T_8$ | $C_6C_7C_8C_9 > T_6T_7T_8T_9$ | NO |
| | | Ta-205 | AAABbDD | $C_6C_7C_8C_9C_{10} > T_6T_7T_8T_9T_{10};$ DEL CCCCGCCGCAT | $C_6C_7 > T_6T_7$ | WT | NO |
| | | Ta-206 | AaBbDd | $C_6C_7C_8C_9C_{10} > T_6T_7T_8T_9A_{10}$ | GGCCAGGTCCCCCGCCG CATGAT | $C_6C_7C_8C_9C_{10} > T_6T_7T_8T_9A_{10}$ | NO |
| | | Ta-207 | AaBbDd | $C_6C_7C_8C_9C_{10} > T_6T_7T_8T_9A_{10}$ | $C_6C_7C_8C_9C_{10} > T_6T_7T_8T_9T_{10}$ | $C_6C_7C_8C_9C_{10} > T_6T_7T_8T_9A_{10}$ | NO |
| Jing 411 | | Ta-301 | AaBbdd | $C_6C_7C_8 > T_6T_7T_8$ | $C_6C_7 > T_6T_7$ | $C_6C_7C_8C_9C_{10} > T_6T_7T_8T_9T_{10}$ | YES |
| | pmTaGRF4-TaGIF1 + pUBI-A3A | Ta-302 | AaBbDd | $C_6C_7C_8C_9C_{10} > T_6T_7T_8T_9A_{10}$ | $C_6C_7C_8C_9 > T_6T_7T_8T_9$ | $C_6C_7C_8 > T_6T_7T_8$ | YES |
| | | Ta-401 | AaBbDd | $C_6C_7C_8 > T_6T_7T_8$ | $C_6C_7C_8 > T_6T_7T_8$ | $C_6C_7C_8C_9C_{10} > T_6T_7T_8T_9T_{10}$ | YES |
| | | Ta-402 | aaBbDd | $C_6C_7C_8 > T_6T_7T_8$ | $C_6C_7C_8 > T_6T_7T_8$ | $C_6C_7C_8C_9C_{10} > T_6T_7T_8T_9T_{10}$ | NO |
| | | Ta-403 | aabbdd | $C_6C_7C_8C_9C_{10} > T_6T_7T_8T_9T_{10};$ | $C_6C_7C_8C_9C_{10} > T_6T_7T_8T_9T_{10};$ | $A_7C_7C_8C_9 > G_7C_8T_9$ | NO |
| | | Ta-404 | aaBbDd | $C_{-5} > T_{-5}$ | $C_9 > G_9$ | $C_6C_7 > T_6T_7$ | NO |
| | | Ta-405 | AaBbDd | $C_6C_7C_8 > T_6T_7T_8$ | $C_6C_7C_8 > T_6T_7T_8$ | $C_6C_7C_8C_9C_{10} > T_6T_7T_8T_9T_{10}$ | NO |
| Zhoumai 27 | | Ta-431 | AaBbDd | $C_6C_7 > T_6T_7$ | $C_6C_7C_8 > T_6T_7T_8$ | $C_6C_7C_8C_9C_{10} > T_6T_7T_8T_9T_{10}$ | NO |
| | | Ta-432 | AaBbdd | $C_6C_7C_8C_9 > T_6T_7T_8T_9$ | $C_6C_7C_8C_9 > T_6T_7T_8T_9$ | $C_6C_7C_8C_9C_{10} > T_6T_7T_8T_9T_{10}$ | NO |
| | | Ta-433 | AaBbDd | $C_6C_7C_8 > T_6T_7T_8$ | $C_6C_7C_8C_9 > T_6T_7T_8T_9$ | $C_6C_7C_8C_9C_{10} > T_6T_7T_8T_9T_{10}$ | YES |
| | | Ta-434 | AaBbDd | $C_6C_7 > T_6T_7$ | $C_6C_7C_8 > T_6T_7T_8$ | $C_6C_7C_8 > T_6T_7T_8$ | NO |
| | pmTaGRF4-TaGIF1 + pUBI-A3A | Ta-450 | AaBbDd | $C_6C_7C_8 > T_6T_7T_8$ | $C_6C_7C_8 > T_6T_7T_8$ | $C_6C_7C_8C_9C_{10} > T_6T_7T_8T_9T_{10};$ | NO |
| | | Ta-451 | aaBBDD | WT | WT | WT | YES |
| | | Ta-452 | Aabbdd | $C_6C_7C_8C_9 > T_6T_7T_8T_9$ | $C_6C_7C_8C_9 > T_6T_7T_8T_9$ | $C_6C_7C_8C_9C_{10} > T_6T_7T_8T_9T_{10}$ | YES |
| | | Ta-453 | aabbdd | | $C_6C_7C_8C_9 > T_6T_7T_8T_9$ | $C_6C_7C_8C_9 > T_6T_7T_8T_9$ | YES |
| | | Ta-454 | aabbDd | $C_6C_7C_8C_9C_{10} > T_6T_7T_8T_9T_{10};$ | $C_6C_7C_8C_9C_{10} > T_6T_7T_8T_9T_{10};$ | $C_{10} > T_{10}$ | NO |
| | | Ta-455 | AabbDd | $C_6C_7 > T_6T_7$ | $C_6C_7C_8 > T_6T_7T_8$ | | NO |
| | | Ta-456 | AaBbDd | $C_6C_7 > T_6T_7$ | $C_6C_7C_8C_9 > T_6T_7T_8T_9$ | $C_6C_7 > T_6T_7$ | YES |
| | | Ta-457 | AaBbDd | $C_6C_7C_8 > T_6T_7T_8$ | $C_6C_7C_8C_9 > T_6T_7T_8T_9$ | $C_6C_7 > T_6T_7$ | YES |

TABLE 15-continued

Genotypes of the T0 taals mutants regenerated from immature embryos of nine elite common wheat cultivars treated with mTaGRF4-TaGIF1 and UBI-GFP (CK), respectively.

| Wheat cultivar | Vectors delivered | Mutant ID | Genotype | A subgenome | B subgenome | D subgenome | Transgene-free |
|---|---|---|---|---|---|---|---|
| Zhoumai 28 | pmTaGRF4-TaGIF1 + pUBI-A3A | Ta-411 | AaBbDd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8 > T_6T_7T_8$ | YES |
| | | Ta-412 | aabbdd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8C_9C_{10} > T_6T_7T_8T_9T_{10}$ | NO |
| | | Ta-413 | AaBbDd | $C_6C_7C_8 > T_6T_7T_8$ | $C_6C_7C_8 > T_6T_7T_8$ | $C_6C_7C_8C_9C_{10} > T_6T_7T_8T_9T_{10}$ | YES |
| | | Ta-414 | aaBBDD | $C_6C_7C_8 > T_6T_7T_8$ | WT | WT | NO |
| | | Ta-415 | aabbdd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8C_9C_{10} > T_6T_7T_8T_9T_{10}$ | NO |
| | | Ta-416 | AaBbDd | $C_6C_7C_8C_9C_{10} > T_6T_7T_8T_9T_{10}$ | $C_6C_7C_8 > T_6T_7T_8$ | $C_6C_7C_8 > T_6T_7T_8$ | NO |
| | | Ta-417 | AaBBDD | $C_6C_7 > T_6T_7$ | WT | $C_6C_7C_8 > T_6T_7T_8$ | YES |
| | | Ta-418 | AabbDd | $C_6C_7C_8C_9C_{10} > T_6T_7T_8T_9T_{10}$ | $C_6C_7C_8 > T_6T_7T_8$ | $C_6C_7C_8C_9C_{10} > T_6T_7T_8T_9T_{10}$ | NO |
| | | Ta-419 | AaBbDd | $C_6C_7C_8 > T_6T_7T_8$ | $C_6C_7C_8C_9C_{10} > T_6T_7T_8T_9T_{10}$ | $C_6C_7C_8C_9C_{10} > T_6T_7T_8T_9T_{10}$ | NO |
| | | Ta-420 | AaBbDd | $C_6C_7C_8C_9C_{10} > T_6T_7T_8T_9T_{10}$ | $C_6C_7C_8 > T_6A_7T_8$ | $C_6C_7C_8C_9C_{10} > T_6T_7T_8T_9T_{10}$ | YES |
| Xiaoyan 54 | pmTaGRF4-TaGIF1 + pUBI-A3A | Ta-501 | AaBbdd | $C_6C_7C_8C_9C_{10} > T_6T_7T_8T_9T_{10}$ | $C_6C_7C_8C_9C_{10} > T_6T_7T_8T_9T_{10}$ | $C_6C_7C_8C_9C_{10} > T_6T_7T_8T_9T_{10}$ | YES |
| | | Ta-502 | aaBBDD | $C_6C_7C_8C_9C_{10} > T_6T_7T_8T_9T_{10}$ | $C_6C_7C_8 > T_6T_7T_8$ | $C_6C_7C_8C_9 > T_6T_7T_8T_9$ | YES |
| | | Ta-503 | Aabbdd | $C_6C_7C_8C_9C_{10} > T_6T_7T_8T_9T_{10}$ | $C_6 > T_6$; $C_6 > T_6$ | $C_6C_7C_8C_9 > T_6T_7T_8T_9$; $C_6C_7C_8C_9 > T_6T_7T_8T_9$ | NO |
| | | Ta-504 | aabbdd | Del CCCCCGCGCA | | $C_6C_7C_8C_9 > T_6T_7T_8T_9$ | NO |
| | | Ta-505 | aabbDd | $C_6C_7C_8 > T_6T_7T_8$ | $C_6C_7C_8C_9C_{10} > T_6T_7T_8T_9T_{10}$ | $C_6C_7C_8 > T_6T_7T_8$ | YES |
| | | Ta-506 | AabbDd | $C_6C_7C_8C_9 > T_6T_7T_8T_9$ | $C_6C_7C_8 > T_6T_7T_8$ | $C_6C_7C_8C_9C_{10} > T_6T_7T_8T_9A_{10}$ | NO |

Aa/aa, Bb/bb, and Dd/dd represent heterozygous/homozygous mutations in TaALS-1A, TaALS-1B, and TaALS-1D, respectively.

Sequences

SEQ ID NO: 1
ZmWUS amino acid sequence
MAANAGGGGAGGGSGSGSVAAPAVCRPSGSRWTPTPEQIRMLKELYYGCGIRSPSSEQIQRITAMLRQHGKIE
GKNVFYWFQNHKARERQKRRLTSLDVNVPAAGAADATTSQLGVLSLSSPPPSGAAPPSPTLGFYAAGNGGGS
AVLLDTSSDWGSSGAAMATETCFLQDYMGVTDTGSSSQWPRFSSSDTIMAAAAARAATTRAPETLPLFPTCG
DDGGSGSSSYLPFWGAASTTAGATSSVAIQQQHQLQEQYSFYSNSNSTQLAGTGNQDVSATAAAAAALELSL
SSWCSPYPAAGSM SEQ ID NO: 2
ZmBBM amino acid sequence
MATVNNWLAFSLSPQELPPSQTTDSTLISAATADHVSGDVCFNIPQDWSMRGSELSALVAEPKLEDFLGGISFS
EQHHKANCNMIPSTSSTVCYASSGASTGYHHQLYHQPTSSALHFADSVMVASSAGVHDGGAMLSAAAANG
VAGAASANGGGIGLSMIKNWLRSQPAPMQPRVAAAEGAQGLSLSMNNMAGTTQGAAGMPLLAGERARAPES
VSTSAQGGAVVVTAPKEDSGGSGVAGALVAVSTDTGGSGGASADNTARKTVDTFGQRTSIYRGVTRHRWTG
RYEAHLWDNSCRREGQTRKGRQVYLGGYDKEEKAARAYDLAALKYWGATTTTNFPVSNYEKELEDMKHMTR
QEFVASLRRKSSGFSRGASIYRGVTRHHQHGRWQARIGRVAGNKDLYLGTFSTQEEAAEAYDIAAIKFRGLNAV
TNFDMSRYDVKSILDSSALPIGSAAKRLKEAEAASAQHHHAGVVSYDVGRIASQLGDGGALAAAYGAHYHG
AAWPTIAFQPGAASTGLYHPYAQQPMRGGGWCKQEQDHAVIAAAHSLQDLHHLNLGAAGAHDFFSAGQQ
AAAAAMHGLGSIDSASLEHSTGSNSVVYNGGVGDSNGASAVGGSGGGYMMPMSAAGATTTSAMVSHEQV
HARAYDEAKQAAQMGYESYLVNAENNGGGRMSAWGTVVSAAAAAAASSNDNMAADVGHGGAQLFSVW
NDT SEQ ID NO: 3 ZmSERK amino acid sequence
MAAAEARRRSAVWALLPLLLRLLHPAALVLANTEGDALHSLRTNLNDPNNVLQSWDPTLVNPCTWFHVTCN
NDNSVIRVDLGNAALSGTLVPQLGQLKNLQYLELYSNNISGTIPSELGNLTNLVSLDLYUNNFTGPIPDSLGKLLK
LRFLRLNNNSLSGSIPKSLTAITALQVLDLSNNNLSGEVPSTGSFSLFTPISFGNNPNLCGPGTTKPCPGAPPFSPP
PPYNPTTPVQSPGSSSSSTGAIAGGVAAGAALLFAIPAISFAYWRRRKPQEHFFDVPAEEDPEVHLGQLKRFSLR
ELQVATDGFSNKNILGRGGFGKVYKGRLADGSLVAVKRLKEERTPGGELQFQTEVEMISMAVHRNLLRLRGFC
MTPTERLLVYPYMANGSVASRLRDRPPAEPPLDWQTRQRIALGSARGLSYLHDHCDPKIIHRDVKAANILLDED
FEAVVGDFGLAKLMDYKDTHVTTAVRGTIGHIAPEYLSTGKSSEKTDVFGYGITLLELITGQRAFDLARLANDDD
VMLLDWVVNCAISSVQIVPQVFMPFLWLPYCAGAGAHLFLCNC SEQ ID NO: 4 TaGRF4 amino acid sequence
MAMPYASLSPAGDRRSSPAATATASLLPFCRSSPFSAGGNGGMGEEARMDGRWMARPVPFTAAQYEELEHQ
ALIYKYLVAGVSVPPDLVLPIRRGIESLAARFYHNPLAIGYGSYLGKKVDPEPGRCRRTDGKKWRCAKEAASDSKY
CERHMHRGRNRSRKPVETQLVSHSQPPAASVVPPLATGFHNHSLYPAIGGTNGGGGGNNGMSMPGTFSS
ALGPPQQHMGNNAASPYAALGGAGTCKDFRYTAYGIRSLADEQSQLMTEAMNTSVENPWRLPPSSQTTTFP
LSSYSPQLGATSDLGQNNSSNNNSGVKAEGQQQQQPLSFPGCGDFGSGDSAKQENQTLRPFFDEWPKTRDS
WSDLTDDNSNVASFSATQLSISIPMTSSDFSAASSQSPNGMLFAGEMY SEQ ID NO: 5 miR396 binding site mutated TaGRF4 amino acid sequence
MAMPYASLSPAGDRRSSPAATATASLLPFCRSSPFSAGGNGGMGEEARMDGRWMARPVPFTAAQYEELEHQ
ALIYKYLVAGVSVPPDLVLPIRRGIESLAARFYHNPLAIGYGSYLGKKVDPEPGRCRRTDGKKWRCAKEAASDSKY
CERHMHRGRNRSRKPVETQLVSHSQPPAASVVPPLATGFHNHSLYPAIGGTNGGGGGNNGMSMPGTFSS
ALGPPQQHMGNNAASPYAALGGAGTCKDFRYTAYGIRSLADEQSQLMTEAMNTSVENPWRLPPSSQTTTFP
LSSYSPQLGATSDLGQNNSSNNNSGVKAEGQQQQQPLSFPGCGDFGSGDSAKQENQTLRPFFDEWPKTRDS
WSDLTDDNSNVASFSATQLSISIPMTSSDFSAASSQSPNGMLFAGEMY SEQ ID NO: 6
TaGIF1 amino acid sequence
MQQQHLMQMNQSMMGGYASSTTATTDLIQQYLDENKQLILAILDNQNNGKVEECARNQAKLQQNLMYLA
AIADSQPPQTASLSQYPSNLMMQSGPRYMQQQSAQMMSPQSLMAARSSMMYAQQAMSPLQQQQQQQ
QHQAAAHGQLGMSSGATTGFNLLHGEASMGGGGGATGNSMMNASVFSDYGRGGSGAKEGSTSLSADARG
ANSGAHSGDEYLKGTEEEGS SEQ ID NO: 7 GmGRF5 amino acid sequence
MGELFGVGKRRNISSSNNNNNSSSSSVLGLDVKVQQSPEALFHNRMMMAHHNHHHRPLSSSPFDNNGDG
DGPTTYMSFTNHINLVSGASSVLGPAIDAGCGAAPPAPVRTLQPFDISSYTSSPTTTTTFNFKPPSAGVMAASL
GFPPFTSAQWRELERQAMIYKYMMASVPVPHDLLTPSSRSSCMDGGFNLRLANSTDPEPGRCRRTDGKKWRCS
RDVAPNHKYCERHMHRGRPRSRKPVEVNTNSTTTPTSVNNNNHQIKKARHECNNNPFATPDVTAAISNPTSR
KNGSSPHFLGSTTTQPYLDSSLSLDNFGLKAASFDSVASVSANKEPRGLEWMLNGDPISLGASDSQWQSLMH
NKDGMTSVSSCNTTESQYLNSLALYNSGLEQQNRRHPLFLNPLVVPMENLQPEKPRGFIDAWSNAESNANTN
TTNKNSAASIGKLSLSSLDLSMGGAAVNEDVGNVNMGLGLMEPNGKTHTGTKISLSNWQNPAPWVASSLGG
PLAEVLRSSTVTATTTTNEATSNTPSPATTTHAESPSGVLQKTLVSLSDSSNNSSPRVASSRANSEMALLRFQSN SEQ ID NO: 8 GmGRF6 amino acid sequence
MMSASARNRSPFTQTQWQELEHQALVFKYMVTGTPIPPDLIYSIKRSLDTSISSRLFPHHPIGWGCFEMGFGRK
VDPEPGRCRRTDGKKWRCSKEAYPDSKYCERHMHRGRNRSRKPVEVSSAISTATNTSQTIPSSYTRNLSLTNPN
MTPPSSFPFSPLPSSMPIESQPFSQSYQNSSLNPFFYSQSTSSRPPDADFPPQDATTHQLFMDSGSYSHDEKNY
RHVHGIREDVDERAFFPEASGSARSYTESYQQLSMSSYKSYSNSNFQNINDATTNPRQQEQQQQQHCFVLGT
DFKSTRPTKEKEAETATGQRPLHRFFGEWPPKNTTDSWLDLASNSRIQTDE SEQ ID NO: 9 GmGRF11 amino acid sequence
MNNSSGGGGRGTLMGLSNGYCGRSPFTVSQWQELEHQALIFKYMLAGLPVPLDLVFPIQNSFHSTISLSHAFF
HHPTLSYCSFYGKKVDPEPGRCRRTDGKKWRCSKEAYPDSKYCERHMHRGRNRSRKPVESQTMTHSSSTVTSL
TVTGGSGASKGTVNFQNLSTNTFGNLQGTDSGTDHTNYHLDSIPYAIPSKEYRYVQGLKSEGGEHCFFSEASGS
NKVLQMESQLENTWPLMSTRVASFSTSKSSNDSLLHSDYPRHSFLSGEYVSGEHVKEEGQPLRPFFNEWPKSRE
SWSGLEDERSNQTAFSTTQLSISIPMSSNFSATSSQSPHGEDEIQFR

| Sequences |
| --- |
| SEQ ID NO: 10 GmGRF18 amino acid sequence<br>MDLGVVGLEGVVGSESGCVFGSSLVSDPETKHKWYGSGLLKQERSAIATEDDEWRISKVAKTDHDMSSASKA<br>MLFQQRNNSLLRSNNATLFSDGHHQSQMLSFSSPKSDSLLIDKASSNATLPFSSHQLSSYTRNTGYNSGSISMH<br>GALASVRGPFTPSQWMELEHQALIYKYITANVPVPTHLLIPIRKALDSVGFCNFSAGLLRPNSLGWGGFHLGFSN<br>NTDPEPGRCRRTDGKKWRCSRDAVVDQKYCERHMNRGRHRSRKPVEGQSGHALTTTTSNTPNASSNSVVPG<br>NNNNTFAHNNVHHPIPPHSSPVNTITRMFTSNKENNNSTSERMQDPALPMLPPTLELKPKENNPFMIHKHQIP<br>SDEYSSRNNNEFGLVTSDSLLNPSEKRSFTSSQKNDSSESQQQHSLRHFIDDSPKPQSNHHHRSSSIWPELDN<br>MQSDRTQLSISIPISSSDHFMSFTTSLPSNEKLTLSPLRLSRELDPIQMGLGVGSAPNEANTRQANWIPITWESSM<br>GGPLGEVLNLSNNNSNASDQCGKNNNNTSALNLMKDGWDNNPPSGSSPTGVLQKSAFGSLSNSSAGSSP<br>RGAENNKEGATLCNAL<br><br>SEQ ID NO: 11 GmGIF1 amino acid sequence<br>MFGSLFHFPHCLLHVLHQSFYDACFSQRYLRSHFLTFQITMSESEYALFGDHKPSPYQNYLDENKSLILKIVESQN<br>SGKLSECAENQARLQRNLMYLAAIADSQPQPPTMPGQYPPSGMMQQGAHYMQAQQQTQQMSPQQLMA<br>ARSSLLYAQQPYSALQQQQAMHSALGSSSGLHMLQSEGSNVNVGSGSGSVGGGFPDLVRGGGGGGSTGE<br>GLHSGGRGIMGSSKQEIGGSSEGRGGGSSEGGENLYLKIADDGN<br><br>SEQ ID NO: 12 linkerA<br>AAAA<br><br>SEQ ID NO: 13 linkerS<br>SGGS<br><br>SEQ ID NO: 14 A3A base editor amino acid sequence<br>MEASPASGPRHLMDPHIFTSNFNNGIGRHKTYLCYEVERLQNGTSVKMDQHRGFLHNQAKNLLCGFYGRHAE<br>LRFLDLVPSLQLDPAQIYRVTWFISWSPCFSWGCAGEVRAFLQENTHVRLRIFAARIYDYDPLYKEALQMLRDA<br>GAQVSIMTYDEFKHCWDTFVDHQGCPFQPWDGLDEHSQALSGRLRAILQNQGNSGSETPGTSESATPESLKD<br>KKYSIGLAIGTNSVGWAVITDEYKVPSKKFKVLGNTDRHSIKKNLIGALLFDSGETAEATRLKRTARRRYTRRKNRI<br>CYLQEIFSNEMAKVDDSFFHRLEESFLVEEDKKHERHPIFGNIVDEVAYHEKYPTIYHLRKKLVDSTDKADLRLIYL<br>ALAHMIKFRGHFLIEGDLNPDNSDVDKLFIQLVQTYNQLFEENPINASGVDAKAILSARLSKSRRLENLIAQLPGE<br>KKNGLFGNLIALSLGLTPNFKSNFDLAEDAKLQLSKDTYDDDLDNLLAQIGDQYADLFLAAKNLSDAILLSDIL<br>NTEITKAPLSASMIKRYDEHHQDLTLLKALVRQQLPEKYKEIFFDQSKSNGYAGYIDGGASQEEFYKFIKPILEKMD<br>GTEELLVKLNREDLLRKQRTFDNGSIPHQIHLGELHAILRRQEDFYPFLKDNREKIEKILTFRIPYYVGPLARGNSRF<br>AWMTRKSEETITPWNFEEVVDKGASAQSFIERMTNFDKNLPNEKVLPKHSLLYEFFTVYNELTKVKYTEGMRK<br>PÅFLSGEQKKAIVDLLFKTNRKVTVKQLKEDYFKKIECFDSVEISGVEDRFNASLGTYHDLLKIIKDKDFLDNEENE<br>DILEDIVLTLTLFEDREMIEERLKTYAHLFDDKVMKQLKRRRYTGWRLSRKLINGIRDKQSGKTILDFLKSDGFAN<br>RNFMQLIHDDSLTFKEDIQKAQVSGQGDSLHEHIANLAGSPAIKKGILQTVKVVDELVKVMGRHKPENIVIEMA<br>RENQTTQKGQKNSRERMKRIEEGIKELGSQILKEHPVENTQLQNEKLYLYYLQNGRDMYVDQELDINRLSDYD<br>VDHIVPQSFLKDDSIDNKVLTRSDKNRGKSDNVPSEEVVKKMKNYWRQLLNAKLITQRKFDNLTKAERGGLSEL<br>DKAGFIKRQLVETRQITKHVAQILDSRMNTKYDENDKLIREVKVITLKSKLVSDFRKDFQFYKVREINNYHHAD<br>AYLNAVVGTALIKKYPKLESEFVYGDYKVYDVRKMIAKSEQEIGKATAKYFFYSNIMNFFKTEITLANGEIRKRPLIE<br>TNGETGEIVWDKGRDFATVRKVLSMPQVNIVKKTEVQTGGFSKESILPKRNSDKLIARKKDWDPKKYGGFDSPT<br>VAYSVLVVAKVEKGKSKKLKSVKELLGITIMERSSFEKNPIDFLEAKGYKEVKKDLIIKLPKYSLFELENGRKRMLASA<br>GELQKGNELALPSKYVNFLYLASHYEKLKGSPEDNEQKQLFVEQHKYLDEIIEQISEFSKRVILADANLDKVLSAY<br>NKHRDKPIREQAENIIHLFTLTNLGAPAAFKYFDTTIDRKRYTSTKEVLDATLIHQSITGLYETRIDLSQLGGDKRPA<br>ATKKAGQAKKKKTRDSGGSTNLSDIIEKETGKQLVIQESILMLPEEVEEVIGNKPESDILVHTAYDESTDENVMLLT<br>SDAPEYKPWALVIQDSNGENKIKMLSGGSPKKKRKV<br><br>SEQ ID NO: 15 SpCas9 amino acid sequence<br>MDKKYSIGLDIGTNSVGWAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIYHLRKKLVDSTDKADLRLI<br>YLALAHMIKFRGHFLIEGDLNPDNSDVDKLFIQLVQTYNQLFEENPINASGVDAKAILSARLSKSRRLENLIAQLP<br>GEKKNGLFGNLIALSLGLTPNFKSNFDLAEDAKLQLSKDTYDDDLDNLLAQIGDQYADLFLAAKNLSDAILLSDIL<br>RVNTEITKAPLSASMIKRYDEHHQDLTLLKALVRQQLPEKYKEIFFDQSKNGYAGYIDGGASQEEFYKFIKPILEKM<br>DGTEELLVKLNREDLLRKQRTFDNGSIPHQIHLGELHAILRRQEDFYPFLKDNREKIEKILTFRIPYYVGPLARGNSR<br>FAWMTRKSEETITPWNFEEVVDKGASAQSFIERMTNFDKNLPNEKVLPKHSLLYEYFTVYNELTKVKYVTEGMR<br>KPAFLSGEQKKAIVDLLFKTNRKVTVKQLKEDYFKKIECFDSVEISGVEDRFNASLGTYHDLLKIIKDKDFLDNEENE<br>DILEDIVLTLTLFEDREMIEERLKTYAHLFDDKVMKQLKRRRYTGWGRLSRKLINGIRDKQSGKTILDFLKSDGFAN<br>RNFMQLIHDDSLTAKEDIQKAQVSGQGDSLHEHIANLAGSPAIKKGILQTVKVVDELVKVMGRHKPENIVIEMA<br>RENQTTQKGQKNSRERMKRIEEGIKELGSQILKEHPVENTQLQNEKLYLYYLQNGRDMYVDQELDINRLSDYD<br>VDHIVPQSFLKDDSIDNKVLTRSDKNRGKSDNVPSEEVVKKMKNYWRQLLNAKLITQRKFDNLTKAERGGLSEL<br>DKAGFIKRQLVETRQITKHVAQILDSRMNTKYDENDKLIREVKVITLKSKLVSDFRKDFQFYKVREINNYHHAHD<br>AYLNAVVGTALIKKYPKLESEFVYGDYKVYDVRKMIAKSEQEIGKATAKYFFYSNIMNFFKTEITLANGEIRKRPLIE<br>TNGETGEIVWDKGRDFATVRKVLSMPQVNIVKKTEVQTGGFSKESILPKRNSDKLIARKKDWDPKKYGGFDSPT<br>VAYSVLVVAKVEKGKSKKLKSVKELLGITIMERSSFEKNPIDFLEAKGYKEVKKDLIIKLPKYSLFELENGRKRMLASA<br>GELQKGNELALPSKYVNFLYLASHYEKLKGSPEDNEQKQLFVEQHKYLDEIIEQISEFSKRVILADANLDKVLSAY<br>NKHRDKPIREQAENIIHLFTLTNLGAPAAFKYFDTTIDRKRYTSTKEVLDATLIHQSITGLYETRIDLSQLGGDKRPA<br>ATKKAGQAKKKK<br><br>SEQ ID NO: 16 sgRNA scaffold sequence<br>GTTTTAGAGCTAGAAATAGCAAGTTAAAATAAGGCTAGTCCGTTATCAACTTGAAAAAGTGGCACCGAGT<br>CGGTGC<br><br>SEQ ID NO: 17 GmGRF5-GmGIF1<br>ATGGGTGAATTATTTGGCGTTGGAAAAAGAAGGAACATCAGCAGCAGCAACAACAACAACAGTTCT<br>AGTAGTAGCGTTCTTGGGTTGGATGTGAAGGTGCAACAGAGCCCTGAAGCATTATTCCATAATAGGATGA<br>TGATGATGGCGCATCATAATCATCACCACCGTCCATTGTCATCACCCTTTGATAATAATGGTGATGGCGAT |

```
GGTCCCACGACTTACATGTCTTTTACTAATCATATAAACCTTGTTAGTGGTGCTTCTTCTGTTCTTGGTCCTG
CTATTGATGCTGGCTGTGGTGCTGCTCCTCCTGCACCTGTAAGAACTTTGCAGCCTTTTGACATTTCTTCTT
ATACTTCTTCTCCCACCACCACTACCACAACCTTCAACTTCAAACCCCCTTCAGCAGGTGTGATGGCGGCT
TCGTTGGGGTTTCCTTTCACAAGTGCACAATGGAGGGAGCTTGAAAGACAAGCTATGATATACAAGTACA
TGATGGCTTCTGTTCCTGTTCCACATGATCTCCTCACACCCTCTTCTCGCTCTTCCTGCATGGATGGTGGTT
TCAATCTGAGGTTGGCAAATAGCACTGACCCTGAGCCAGGTAGGTGTAGAAGAACAGATGGTAAAAAAT
GGAGATGTTCAAGAGATGTGGCTCCTAACCACAAGTACTGTGAGCGCCATATGCATAGAGGCCGTCCCC
GTTCAAGAAAGCCTGTGGAAGTTAACACCAACAGCACCACCACTCCCACTAGCGTCAACAATAACAACC
ATCAAATCAAAAGGCTCGCCATGAGTGTAATAATAATCCTTTTGCTACACCTGACGTTACTGCGGCTATT
TCCAACCCCACATCCAGAAAAATGGATCTTCTCCCCATTTTCTTGGGTCTACTACCACTCAGCCATACCT
TGATTCTTCCCTCTCCCTTGATAACTTTGGTCTAAAAGCTGCTAGTTTTGACTCCGTGGCTTCTGTTTCTGCT
AATAAGGAACCCAGGGGTTTAGAGTGGATGCTGAATGGAGATCCTATTTCCCTGGGTGCTTCTGACTCAC
AATGGCAGTCTCTGATGCACAATAAAGATGGAATGACCAGTGTTAGTTCCTGTAACACCACCGAGTCTCA
GTATCTGAATTCATTAGCACTATATAACTCTGGACTAGAACAACAGAATAGACGCCATCCTTTGTTCCTGA
ACCCTCTTGTTGTTCCCATGGAAAATCTCCAACCGGAGAAACAAGGGGTTTATTGATGCTTGGTCTAAC
GCTGAAAGCAATGCCAACACCAACACCACCAACAAGAACTCTGCTGCATCAATTGGTAAATTATCCCTTT
CTTCTCTTGATCTATCAATGGGGGGTGCTGCTGTGAATGAAGATGTGGGTAATGTTAACATGGGTTTGGGC
CTAATGGAGCCTAATGGAAAAACGCACACTGGTACTAAAATTTCTCTCTCCAATTGGCAAAACCCAGCAC
CTTGGGTGGCTTCATCACTTGGGGTCCACTAGCTGAAGTTCTAAGGTCAAGCACAGTCACTGCCACCAC
CACCACCAATGAAGCAACCTCCAACACACCCTCGCCAGCCACCACTACACATGCTGAATCTCCATCTGG
GGTGTTGCAGAAAACGCTTGTTTCATTGTCTGATAGCAGTAACAATAGCAGCCCAAGGGTTGCATCATCA
AGGGCCAATTCTGAGATGGCCTTGCTAAGGTTTCAATCAAATgcggccgctgccATGTTCGGGTCTTTGTTCC
ATTTTCCACACTGTCTACTACATGTGCTGCATCAGAGCTTTTATGACGCGTGCTTTTCTCAGCGCTACCTCA
GATCACATTTTCTCACCTTTCAGATCACAATGTCTGAATCCGAATATGCTTTGTTTGGAGATCACAAACCTT
CTCCCTATCAAAACTATCTGGATGAGAACAAGTCCTTAATTCTGAAGATTGTTGAAAGCCAGAATTCAGG
CAAGCTTAGCGAGTGTGCCGAGAACCAAGCAAGGCTTCAGAGAAATCTCATGTACTTAGCTGCAATAGCT
GATTCTCAACCCCAACCACCCACCATGCCTGGTCAGTACCCTCCGAGTGGGATGATGCAGCAGGGAGCA
CACTACATGCAGGCTCAACAACAGACACAGCAGATGTCACCACAACAACTAATGGCGGCACGCTCGTCC
CTTTTGTACGCACAGCAGCCATACTCAGCACTTCAACAGCAGCAAGCCATGCACAGTGCACTCGGGTCG
AGTTCAGGACTCCACATGCTGCAAAGTGAAGGCAGCAATGTGAATGTGGGATCAGGCAGTGGCTCTGTA
GGAGGAGGGTTTCCTGACTTGGTGCGCGGTGGTGGTGGTGGCGGTGGCTCGACAGGGGAGGGTTTGCA
CAGTGGTGGAAGGGGTATCATGGGAAGTAGCAAGCAGGAAATTGGGGGTTCAAGTGAAGGCCGAGGTG
GGGGAAGCTCAGAGGGTGGTGAAAACCTTTACCTCAAAATTGCCGACGATGGAAAC SEQ ID NO: 18 GmGRF6-GmGIF1
ATGATGAGTGCAAGTGCAAGAAATAGGTCTCCTTTCACGCAAACTCAGTGGCAAGAGCTTGAGCATCAA
GCTCTTGTTTTTAAGTACATGGTTACAGGAACACCCATCCCACCAGATCTCATCTACTCTATTAAAAGAAG
TCTAGACACTTCAATTTCTTCAAGGCTCTTCCCACATCATCCAATTGGGTGGGATGTTTTGAAATGGGAT
TTGGCAGAAAAGTAGACCCAGAGCCAGGGAGGTGCAGAAGAACAGATGGCAAGAAATGGAGATGCTCA
AAGGAGGCATATCCAGACTCCAAGTACTGTGAAAGACACATGCACAGAGGCAGAAACCGTTCAAGAAA
GCCTGTGGAAGTTCTTCAGCAATAAGCACCGCCACAAACACCTCCCAAACAATCCCATCTTCTTCATACCC
GAAACCTTTCCTTGACCAACCCCAACATGACACCACCCTCTTCCTTCCCTTTCTCTCCTTTGCCCTCTTCTA
TGCCTATTGAGTCCCAACCCTTTTCCCAATCCTACCAAAACTCTTCTCTCAATCCCTTCTTCTACTCCCAAT
CAACCTCCTCTAGACCCCCAGATGCTGATTTTCCACCCCAAGATGCCACCACCACCAGCTATTCATGGA
CTCTGGGTCTTATTCGCATGATGAAAAGAATTATAGGCATGTTCATGGAATAAGAGAAGATGTGGATGAG
AGAGCTTTCTTCCCAGAAGCATCAGGATCAGCTAGGAGCTACACTGAATCATACCAGCAACTATCAATGA
GCTCCTACAAGTCCTATTCAAACTCCAACTTTCAGAACATCAATGATGCCACCACCAACCCAAGACAGCA
AGAGCAGCAACAACAACAACACTGCTTTGTTTTGGGGACAGACTTCAAATCAACAAGACCAACTAAAGA
GAAAGAAGCTGAGACAGCTACGGGTCAGAGACCCCTTCACCGTTTCTTTGGGGAGTGGCCACCAAAGAA
CACAACAGATTCATGGCTAGATCTTGCTTCCAACTCCAGAATCCAAACCGATGAAgcggccgctgccATGTTC
GGGTCTTTGTTCCATTTTCCACACTGTCTACTACATGTGCTGCATCAGAGCTTTTATGACGCGTGCTTTTCT
CAGCGCTACCTCAGATCACATTTTCTCACCTTTCAGATCACAATGTCTGAATCCGAATATGCTTTGTTTGGA
GATCAAACCTTCTCCCTATCAAAACTATCTGGATGAGAACAAGTCCTTAATTCTGAAGATTGTTGAAAG
CCAGAATTCAGGCAAGCTTAGCGAGTGTGCCGAGAACCAAGCAAGGCTTCAGAGAAATCTCATGTACTT
AGCTGCAATAGCTGATTCTCAACCCCAACCACCCACCATGCCTGGTCAGTACCCTCCGAGTGGGATGATG
CAGCAGGGAGCACACTACATGCAGGCTCAACAACAGACACAGCAGATGTCACCACAACAACTAATGGC
GGCACGCTCGTCCCTTTTGTACGCACAGCAGCCATACTCAGCACTTCAACAGCAGCAAGCCATGCACAGT
GCACTCGGGTCGAGTTCAGGACTCCACATGCTGCAAAGTGAAGGCAGCAATGTGAATGTGGGATCAGGC
AGTGGCTCTGTAGGAGGAGGGTTTCCTGACTTGGTGCGCGGTGGTGGTGGTGGCGGTGGCTCGACAGGG
GAGGGTTTGCACAGTGGTGGAAGGGGTATCATGGGAAGTAGCAAGCAGGAAATTGGGGGTTCAAGTGA
AGGCCGAGGTGGGGGAAGCTCAGAGGGTGGTGAAAACCTTTACCTCAAAATTGCCGACGATGGAAAC SEQ ID NO: 19 GmGRF11-GmGIF1
ATGAACAACAGCAGTGGCGGAGGAGGACGAGGAACTTTGATGGGTTTGAGTAATGGGTATTGTGGGAGG
TCGCCATTCACAGTGTCTCAGTGGCAGGAACTGGAGCACCAAGCTTTGATCTTCAAGTACATGCTTGCGG
GTCTTCCTGTTCCTCTCGATCTCGTGTTCCCCATTCAGAACAGCTTCCACTCTACTATCTCGCTCTCGCACG
CTTTCTTTCACCATCCCACGTTGAGTTACTGTTCCTTCTATGGAAGAAGGTGGACCCTGAGCCAGGACGA
TGCAGGAGGACTGATGAAAAAAGTGGAGGTGCTCCAAGGAAGCATACCCAGACTCCAAGTACTGCGA
GCGCCACATGCACCGTGGCCGCAACCGTTCAAGAAAGCCTGTGGAATCACAAACTATGACTCACTCATCT
TCAACTGTCACATCACTCACTGTCACTGGGGTAGTGGTGCCAGCAAAGGAACTGTAAATTTCCAAAACC
TTTCTACAAATACCTTTGGTAATCTCCAGGGTACCGATTCTGAACAGCTTCCACTACACCAATTATCATGATT
CCATTCCCTATGCGATTCAAGTAAAGAATACAGGTATGTTCAAGGACTTAAATCTGAGGGTGTGGAGCA
CTGCTTTTTTTCTGAAGCTTCTGGAAGCAACAAGGTTCTCCAAATGGAGTCACAGCTGGAAAACACATGG
CCTTTGATGTCAACCAGAGTTGCCTCTTTTTCTACGTCAAAATCAAGTAATGATTCCTGTTGCATAGTGAT
TATCCCCGGCATTCGTTTTATCTGGTGAATATGTGTCGGGAGAACACGTAAAGGAGGAGGGCCAGCCTC
TTCGACCTTTTTTTAATGAATGGCCTAAAAGCAGGGAGTCATGGTCTGGTCTAGAAGATGAGAGATCCAA
CCAAACAGCCTTCTCCACAACTCAACTCTCAATATCCATTCCTATGTCTTCCAATTTCTCTGCAACGAGCTC
```

```
TCAGTCCCCACATGGTGAAGATGAGATTCAATTTAGGgcggccgctgccATGTTCGGGTCTTTGTTCCATTTTC
CACACTGTCTACTACATGTGCTGCATCAGAGCTTTTATGACGCGTGCTTTTCTCAGCGCTACCTCAGATCA
CATTTTCTCACCTTTCAGATCACAATGTCTGAATCCGAATATGCTTTGTTTGGAGATCACAAACCTTCTCCC
TATCAAAACTATCTGGATGAGAACAAGTCCTTAATTCTGAAGATTGTTGAAAGCCAGAATTCAGGCAAGC
TTAGCGAGTGTGCCGAGAACCAAGCAAGGCTTCAGAGAAATCTCATGTACTTAGCTGCAATAGCTGATTC
TCAACCCCAACCACCCACCATGCCTGGTCAGTACCCTCCGAGTGGGATGATGCAGCAGGGAGCACACTA
CATGCAGGCTCAACAACAGACACAGCAGATGTCACCACAACAACTAATGGCGGCACGCTCGTCCCTTTT
GTACGCACAGCAGCCATACTCAGCACTTCAACAGCAGCAAGCCATGCACAGTGCACTCGGGTCGAGTTC
AGGACTCCACATGCTGCAAAGTGAAGGCAGCAATGTGAATGTGGGATCAGGCAGTGGCTCTGTAGGAGG
AGGGTTTCCTGACTTGGTGCGCGGTGGTGGTGGTGGCGGTGGCTCGACAGGGGAGGGTTTGCACAGTGG
TGGAAGGGGTATCATGGGAAGTAGCAAGCAGGAAATTGGGGGTTCAAGTGAAGGCCGAGGTGGGGGAA
GCTCAGAGGGTGGTGAAAACCTTTACCTCAAAATTGCCGACGATGGAAAC SEQ ID NO: 20 GmGRF18-GmGIF1
ATGGATCTTGGGGTGGTGGGTTTGGAGGGGGTGGTGGGTTCAGAAAGTGGTTGTGTGTTTGGTTCTTCTCT
TGTTTCAGATCCTGAGACAAAGCACAAGTGGTACGGATCTGGTTTGCTCAAGCAAGAGAGATCTGCCATA
GCTACTGAAGATGATGAGTGGAGAATTTCCAAAGTTGCTAAAACTGATCATGACATGTCTTCAGCCTCCA
AAGCAATGCTCTTTCAGCAAAGAAACAACTCTTTGTTGAGATCTAATAATGCAACTCTCTTCTCTGATGGT
CATCACCAATCACAAATGTTGAGCTTCTCTTCTCCAAAGTCAGATTCTTTGTTGATAGATAAGGCTTCCTCA
AATGCCACATTGCCTTTTTCTTCCCACCAATTGTCTAGCTACACCAGAAATACAGGTTACAATTCAGGAAG
CATAAGCATGCATGGGGCTTTGGCTAGTGTGAGAGGGCCATTCACTCCATCACAGTGGATGGAGCTTGAA
CACCAAGCCTTGATCTACAAGTACATCACAGCAAATGTTCCTGTGCCAACTCATCTTCTCATTCCCATCAG
AAAAGCACTTGATTCTGTTGGCTTCTGCAACTTCTCAGCCGGACTCCTCAGACCCAACTCATTGGGATGG
GGAGGTTTCCATCTAGGATTCTCGAACAATACAGACCCTGGCAGGGAGGTGTAGGAGAACAGATGGA
AAGAAATGGCGATGTTCAAGAGATGCCGTAGTAGATCAGAAGTATTGCGAGCGGCACATGAACCGAGGA
CGCCATCGTTCAAGAAAGCCTGTGGAAGGCCAATCAGGCCATGCCCTCACCACCACCACCAGTAATACA
CCTAATGCTTCCTCCAACTCTGTGGTGCCTGGCAACAACAACAACACCTTTGCACACAACAATGTGCACC
ACCCTATTCCTCCTCATTCCTCTCCGGTCAACACCATCACTAGGATGTTTACAAGCAACAAAGAGAATAAT
AACAGTACCAGTGAGAGGATGCAGGACCCTGCACTTCCCATGCTTCCTCCCACTCTTGAGCTGAAACCAA
AGGAGAACAATCCTTTCATGATTCATAAACACCAAATCCCATCTGATGAATACTCAAGTAGGAACAACAA
TGAGTTTGGGCTTGTCACTTCTGATTCTTTGCTTAACCCCTCAGAGAAAAGAAGCTTTACTTCTTCACAAAA
GAATGATTCTTCTGAGTCCCAACAACAACATTCCCTCAGGCACTTCATTGATGACTCTCCCAAACCACAGT
CTAATCATCATCATCGTTCGTCGTCTATATGGCCTGAACTTGACAACATGCAGTCAGACAGGACTCAGTTA
TCAATCTCCATACCAATATCTTCCTCAGATCACTTCATGTCATTCACTACTTCCTTGCCCTCGAACGAGAAA
CTCACGTTGTCACCACTTAGGCTTTCAAGGGAGTTAGACCCCATTCAAATGGGGTTGGGAGTGGGAAGTG
CCCCCAATGAAGCAAACACTAGGCAAGCCAATTGGATTCCAATCACTTGGGAGAGTTCAATGGGTGGTC
CTCTTGGAGAGGTTTTGAACCTTAGTAACAATAACAACAGCAATGCTAGTGATCAATGTGGCAAGAACAA
CAACAACACTTCAGCTCTCAACCTCATGAAAGATGGATGGGACAATAATCCTCCATCAGGGTCATCCCCA
ACTGGGGTGCTTCAAAAATCTGCATTTGGATCACTTTCCAATAGCAGTGCTGGGAGCAGTCCAAGGGGGG
CAGAGAACAACAAAGAAGGTGCCACCTTGTGCAATGCCTTGgcggccgctgccATGTTCGGGTCTTTGTTCCA
TTTTCCACACTGTCTACTACATGTGCTGCATCAGAGCTTTTATGACGCGTGCTTTTCTCAGCGCTACCTCAG
ATCACATTTTCTCACCTTTCAGATCACAATGTCTGAATCCGAATATGCTTTGTTTGGAGATCACAAACCTTC
TCCCTATCAAAACTATCTGGATGAGAACAAGTCCTTAATTCTGAAGATTGTTGAAAGCCAGAATTCAGGC
AAGCTTAGCGAGTGTGCCGAGAACCAAGCAAGGCTTCAGAGAAATCTCATGTACTTAGCTGCAATAGCT
GATTCTCAACCCCAACCACCCACCATGCCTGGTCAGTACCCTCCGAGTGGGATGATGCAGCAGGGAGCA
CACTACATGCAGGCTCAACAACAGACACAGCAGATGTCACCACAACAACTAATGGCGGCACGCTCGTCC
CTTTTGTACGCACAGCAGCCATACTCAGCACTTCAACAGCAGCAAGCCATGCACAGTGCACTCGGGTCG
AGTTCAGGACTCCACATGCTGCAAAGTGAAGGCAGCAATGTGAATGTGGGATCAGGCAGTGGCTCTGTA
GGAGGAGGGTTTCCTGACTTGGTGCGCGGTGGTGGTGGTGGCGGTGGCTCGACAGGGGAGGGTTTGCA
CAGTGGTGGAAGGGGTATCATGGGAAGTAGCAAGCAGGAAATTGGGGGTTCAAGTGAAGGCCGAGGTG
GGGGAAGCTCAGAGGGTGGTGAAAACCTTTACCTCAAAATTGCCGACGATGGAAAC SEQ ID NO: 21 TaGRF4-TaGIF1
ATGGCGATGCCGTATGCCTCTCTTTCCCGGCAGGCGACCGCCGCTCCTCCCCGGCCGCCACCGCCACC
GCCTCCCTCCTCCCCTTCTGCCGCTCCTCCCCCTTCTCCGCCGGCGGCAATGGCGGCATGGGGGAGGAG
GCGCGGATGGACGGGAGGTGGATGGCGAGGCCGGTGCCCTTCACGGCGGCGCAGTACGAGGAGCTGG
AGCACCAGGCGCTCATATACAAGTACCTGGTGGCCGGCGTGCTCCTGCCGGATCTCGTGCTCCCCA
TCCGCCGCGGCATCGAGTCCCTCGCCGCCCGCTTCTACCACAACCCCCTCGCCATCGGGTACGGATCGT
ACCTGGGCAAGAAGGTGGATCCGGAGCCGGGCCGGTGCCGGCGCACGGACGGCAAGAAGTGGCGGTG
CGCCAAGGAGGCCGCCTCCGACTCCAAGTATTGCGAGCGCCACATGCACCGCGGCCGCAACCGTTCAA
GAAAGCCTGTGGAAACGCAGCTCGTCTCGCACTCCCAGCCGCCGACGTCCGTCGTGCCGCCCCTCG
CCACCGGCTTCACAACCACTCCCTCTACCCCGCCATCGGCGGCACCAACGGTGGTGGAGGCGGGGGG
AACAACGGCATGTCCATGCCCGGCACGTTCTCCTCCGCGCTGGGGCCGCCTCAGCAGCACATGGGCAAC
AATGCCGCCTCTCCCTACGCGGCTCTCGGCGGCGCCGGAACATGCAAAGATTTCAGGTATACCGCATAT
GGAATAAGATCTTTGGCAGACGAGCAGAGTCAGCTCATGACAGAAGCCATGAACACCTCCGTGGAGAAC
CCATGCGCCTGCCGCCATCTTCTCAAACGACTACATTCCCGCTCTCAAGCTACTCTCCTCAGCTTGGAGC
AACGAGTGACCTGGGTCAGAACAACAGCAGCAACAACAACAGCGGCGTCAAGGCCGAGGGACAGCAG
CAGCAGCAGCCGCTCTCCTTCCCGGGGTGCGGCGACTTCGGCAGCGGCGACTCCGCGAAGCAGGAGAA
CCAGACGCTGCGGCCGTTCTTCGACGAGTGGCCGAAGACGAGGGACTCGTGGTCGGACCTGACCGACG
ACAACTCGAACGTCGCCTCCTTCTCGGCCACCCAGCTGTCGATCTCGATACCCATGACGTCCTCCGACTT
CTCCGCCGCCAGCTCCCAGTCGCCCAACGGCATGCCGCCCCAACGGCATGCTGTTCGCCGGCGAAATGTACgcggccgctgccATGCA
GCAGCAACACCTGATGCAGATGAACCAGAGCATGATGGGGGGCTACGCTTCCTCTACCACTGCCACCAC
TGATCTCATTCAGCAGTACCTGGATGAGAACAAGCAGCTGATCCTGGCCATCCTCGACAACCAGAACAA
CGGCAAGGTGGAGGAGTGCGCACGGAACCAAGCTAAGCTCCAGCAGAACCTCATGTACCTCGCCGCCA
TCGCCGACAGCCAGCCTCCGCAGACGGCATCGCTGTCTCAGTACCCGTCCAACCTGATGATGCAGTCCG
GGCCGCGGTACATGCAGCAGCAGTCGGCGCAGATGATGTCGCCGCAGTCGCTGATGGCGGCGCGGTCG
TCGATGATGTACGCGCAGCAGGCCATGTCGCCGCTCCAGCAGCAGCAGCAGCAGCAGCACCAGGC
```

| Sequences |
| --- |
| GGCCGCGCACGGCCAGCTGGGGATGTCCTCCGGCGCGACCACCGGGTTCAACCTCCTGCACGGTGAGG<br>CCAGCATGGGCGGCGGCGGCGCCACTGGCAACAGCATGATGAACGCCAGCGTCTTCTCGGACTAT<br>GGCCGCGGCGGCAGCGGCGCCAAGGAGGGGTCGACCTCGCTGTCGGCCGACGCTCGCGGCGCCAACT<br>CTGGCGCGCACAGCGGCGACGGGGAGTACCTCAAGGGCACCGAGGAGGAAGGAAGCTAA<br><br>SEQ ID NO: 22 mTaGRF4-TaGIF1<br>ATGGCGATGCCGTATGCCTCTCTTTCCCCGGCAGGCGACCGCCGCTCCTCCCCGGCCGCCACCGCCACC<br>GCCTCCCTCCTCCCCTTCTGCCGCTCCTCCCCCTTCTCCGCCGGCGGCAATGGCGGCATGGGGGAGGAG<br>GCGCGGATGGACGGGAGGTGGATGGCGAGGCCGGTGCCCTTCACGGCGGCGCAGTACGAGGAGCTGG<br>AGCACCAGGCGCTCATATACAAGTACCTGGTGGCCGGCGTGTCCGTCCCGCCGGATCTCGTGCTCCCCA<br>TCCGCCGCGGCATCGAGTCCCTCGCCGCCCGCTTCTACCACAACCCCTCGCCATCGGGTACGGATCGT<br>ACCTGGGCAAGAAGGTGGATCCGGAGCCGGGCCGGTGCCGGCGCACGGACGGCAAGAAGTGGCGGTG<br>CGCCAAGGAGGCCGCCTCCGACTCCAAGTATTGCGAGCGCCACATGCACCGCGGCCGCAACCGTTCtAG<br>AAAaCCaGTaGAgACGCAGCTCGTCTCGCACTCCCAGCCGCCGGCCGCCTCCGTCGTGCCGCCCCTCGCC<br>ACCGGCTTCCACAACCACTCCCTCTACCCCGCCATCGGCGGCGCACCAACGGTGGTGGAGGGGGGGGAA<br>CAACGGCATGTCCATGCCCGGCACGTTCTCCTCCGCGCTGGGGCCGCTCAGCAGCACATGGGCAACAA<br>TGCCGCCTCTCCCTACGCGGCTCTCGGCGGCGCCGGAACATGCAAAGATTTCAGGTATACCGCATATGG<br>AATAAGATCTTTGGCAGACGAGCAGAGTCAGCTCATGACAGAAGCCATGAACACCTCCGTGGAGAACCC<br>ATGGCGCCTGCCGCCATCTTCTCAAACGACTACATTCCCGCTCTCAAGCTACTCCTCAGCTTGGAGCA<br>ACGAGTGACCTGGGTCAGAACAACAGCAGCAACAACAACAGCGCTCAAGGCCGAGGGACAGCAGC<br>AGCAGCAGCCGCTCTCCTTCCCGGGGTGCGGCGACTTCGGCAGCGGCGACTCCGCGAAGCAGGAGAAC<br>CAGACGCTGCGGCCGTTCTTCGACGAGTGGCCGAAGACGAGGGACTCGTGGTCGGACCTGACCGACGA<br>CAACTCGAACGTCGCCTCCTTCTCGGCCACCCAGCTGTCGATCTCGATACCCATGACGTCCTCCGACTTCT<br>CCGCCGCCAGCTCCCAGTCGCCCAACGGCATGCTGTTCGCCGGCGAAATGTACgcggccgctgccATGCAG<br>CAGCAACACCTGATGCAGATGAACCAGAGCATGATGGGGGGCTACGCTTCCTCTACCACTGCCACCACT<br>GATCTCATTCAGCAGTACCTGGATGAGAACAAGCAGCTGATCCTGGCCATCCTCGACAACCAGAACAAC<br>GGCAAGGTGGAGGAGTGCGCACGGAACCAAGCTAAGCTCCAGCAGAACCTCATGTACCTCGCCGCCAT<br>CGCCGACAGCCAGCCTCCGCAGACGGCATCGCTGTCTCAGTACCCGTCCAACCTGATGATGCAGTCCGG<br>GCCGCGGTACATGCAGCAGCAGTCGGCGCAGATGATGTCGCCGCAGTCGCTGATGGCGGCGGGTCGT<br>CGATGATGTACGCGCAGCAGGCCATGTCGCCGCTCCAGCAGCAGCAGCAGCAGCAGCACCAGGCG<br>GCCGCGCACGGCCAGCTGGGGATGTCCTCCGGCGCGACCACCGGGTTCAACCTCCTGCACGGTGAGGC<br>CAGCATGGGCGGCGGCGGCGCCACTGGCAACAGCATGATGAACGCCAGCGTCTTCTCGGACTATG<br>GCCGCGGCGGCAGCGGCGCCAAGGAGGGGTCGACCTCGCTGTCGGCCGACGCTCGCGGCGCCAACTCT<br>GGCGCGCACAGCGGCGACGGGGAGTACCTCAAGGGCACCGAGGAGGAAGGAAGCTAA<br><br>SEQ ID NO: 23 GmGRF5-GmGIF1<br>MGELFGVGKRRNISSSNNNNNSSSSSVLGLDVKVQQSPEALFHNRMMMMAHHNHHHRPLSSPFDNNGDG<br>DGPTTYMSFTNHINLVSGASSVLGPAIDAGCGAAPPAPVRTLQPFDISSYTSSPTTTTTTFNFKPPSAGVMAASL<br>GFPFTSAQWRELERQAMIYKYMMASVPVPHDLLTPSSRSSCMDGGFNLRLANSTDPEPGRCRRTDGKKWRCS<br>RDVAPNHKYCERHMHRGRPRSRKPVEVNTNSTTTPTSVNNNNHQIKKARHECNNNPFATPDVTAAISNPTSR<br>KNGSSPHFLGSTTTQPYLDSSLSLDNFGLKAASFDSVASVSANKEPRGLEWMLNGDPISLGASDSQWQSLMH<br>NKDGMTSVSSCNTTESQYLNSLALYNSGLEQQNRRHPLFLNPLVVPMENLQPEKPRGFIDAWSNAESNANTN<br>TTNKNSAASIGKLSLSSLDLSMGGAAVNEDVGNVNMGLGLMEPNGKTHTGTKISLSNWQNPAPWVASSLGG<br>PLAEVLRSSTVTATTTTNEATSNTPSPATTTHAESPSGVLQKTLVSLSDSSNNSSPRVASSRANSEMALLRFQSN<br>AAAAMFGSLFHFPHCLLHVLHQSFYDACFSQRYLRSHFLTFQITMSESEYALFGDHKPSPYQNYLDENKSLILKIV<br>ESQNSGKLSECAENQARLQRNLMYLAAIADSQPQPPTMPGQYPPSGMMQQGAHYMQAQQQTQQMSPQ<br>QLMAARSSLLYAQQPYSALQQQQAMHSALGSSSGLHMLQSEGSNVNVGSGSGSVGGGFPDLVRGGGGGG<br>GSTGEGLHSGGRGIMGSSKQEIGGSSEGRGGGSSEGGENLYLKIADDGN<br><br>SEQ ID NO: 24 GmGRF6-GmGIF1<br>MMSASARNRSPFTQTQWQELEHQALVFKYMVTGTPIPPDLIYSIKRSLDTSISSRLFPHHPIGWGCFEMGFGRK<br>VDPEPGRCRRTDGKKWRCSKEAYPDSKYCERHMHRGRNRSRKPVEVSSAISTATNTSQTIPSSYTRNLSLTNPN<br>MTPPSSFPFSPLPSSMPIESQPFSQSYQNSSLNPFFYSQSTSSRPPDADFPPQDATTHQLFMDSGSYSHDEKNY<br>RHVHGIREDVDERAFFPEASGSARSYTESYQQLSMSSYKSYSNSNFQNINDATTNPRQQEQQQQQHCFVLGT<br>DPFKSTRPTKEKEAETATGQRPLHRFFGEWPPKNTTDSWLDLASNSRIQTDEAAAAMFGSLFHFPHCLLHVLHQ<br>SFYDACFSQRYLRSHFLTFQITMSESEYALFGDHKPSPYQNYLDENKSLILKIVESQNSGKLSECAENQARLQRNL<br>MYLAAIADSQPQPPTMPGQYPPSGMMQQGAHYMQAQQQTQQMSPQQLMAARSSLLYAQQPYSALQQ<br>QQAMHSALGSSSGLHMLQSEGSNVNVGSGSGSVGGGFPDLVRGGGGGGGSTGEGLHSGGRGIMGSSKQEI<br>GGSSEGRGGGSSEGGENLYLKIADDGN<br><br>SEQ ID NO: 25 GmGRF11-GmGIF1<br>MNNSSGGGRGTLMGLSNGYCGRSPFTVSQWQELEHQALIFKYMLAGLPVPLDLVFPIQNSFHSTISLSHAFF<br>HHPTLSYCSFYGKKVDPEPGRCRRTDGKKWRCSKEAYPDSKYCERHMHRGRNRSRKPVESQTMTHSSSTVTSL<br>TVTGGSGASKGTVNFQNLSTNTFGNLQGTDSGTDHTNYHLDSIPYAIPSKEYRYVQGLKSEGGEHCFFSEASGS<br>NKVLQMESQLENTWPLMSTRVASFSTSKSSNDSLLHSDYPRHSFLSGEYVSGEHVKEEGQPLRPFFNEWPKSRE<br>SWSGLEDERSNQTAFSTTQLSISIPMSSNFSATSSQSPHGEDEIQFRAAAAMFGSLFHFPHCLLHVLHQSFYDA<br>CFSQRYLRSHFLTFQITMSESEYALFGDHKPSPYQNYLDENKSLILKIVESQNSGKLSECAENQARLQRNLMYLA<br>AIADSQPQPPTMPGQYPPSGMMQQGAHYMQAQQQTQQMSPQQLMAARSSLLYAQQPYSALQQQQAM<br>HSALGSSSGLHMLQSEGSNVNVGSGSGSVGGGFPDLVRGGGGGGGSTGEGLHSGGRGIMGSSKQEIGGSSE<br>GRGGGSSEGGENLYLKIADDGN<br><br>SEQ ID NO: 26 GmGRF18-GmGIF1<br>MDLGVVGLEGVVGSESGCVFGSSLVSDPETKHKWYGSGLLKQERSAIATEDDEWRISKVAKTDHDMSSASKA<br>MLFQQRNNSLLRSNNATLFSDGHHQSQMLSFSSPKSDSLLIDKASSNATLPFSSHQLSSYTRNTGYNSGSISMH<br>GALASVRGPFTPSQWMELEHQALIYKYITANVPVPTHLLIPIRKALDSVGFCNFSAGLLRPNSLGWGGFHLGFSN<br>NTDPEPGRCRRTDGKKWRCSRDAVVDQKYCERHMNRGRHRSRKPVEGQSGHALTTTTSNTPNASSNSVVPG<br>NNNNTFAHNNVHHPIPPHSSPVNTITRMFTSNKENNSTSERMQDPALPMLPPTLELKPKENNPFMIHKHQIP |

-continued

| Sequences |
|---|
| SDEYSSRNNNEFGLVTSDSLLNPSEKRSFTSSQKNDSSESQQQHSLRHFIDDSPKPQSNHHHRSSSIWPELDN<br>MQSDRTQLSISIPISSSDHFMSFTTSLPSNEKLTLSPLRLSRELDPIQMGLGVGSAPNEANTRQANWIPITWESSM<br>GGPLGEVLNLSNNNNSNASDQCGKNNNNTSALNLMKDGWDNNPPSGSSPTGVLQKSAFGSLSNSSAGSSP<br>RGAENNKEGATLCNALAAAAMFGSLFHFPHCLLHVLHQSFYDACFSQRYLRSHFLTFQITMSESEYALFGDHKP<br>SPYQNYLDENKSLILKIVESQNSGKLSECAENQARLQRNLMYLAAIADSQPQPPTMPGQYPPSGMMQQGAH<br>YMQAQQQTQQMSPQQLMAARSSLLYAQQPYSALQQQQAMHSALGSSSGLHMLQSEGSNVNVGSGSGSV<br>GGGFPDLVRGGGGGGGSTGEGLHSGGRGIMGSSKQEIGGSSEGRGGGSSEGGENLYLKIADDGN<br><br>SEQ ID NO: 27 TaGRF4-TaGIF1<br>MAMPYASLSPAGDRRSSPAATATASLLPFCRSSPFSAGGNGGMGEEARMDGRWMARPVPFTAAQYEELEHQ<br>ALIYKYLVAGVSVPPDLVLPIRRGIESLAARFYHNPLAIGYGSYLGKKVDPEPGRCRRTDGKKWRCAKEAASDSKY<br>CERHMHRGRNRSRKPVETQLVSHSQPPAASVVPPLATGFHNHSLYPAIGGTNGGGGGNNGMSMPGTFSS<br>ALGPPQQHMGNNAASPYAALGGAGTCKDFRYTAYGIRSLADEQSQLMTEAMNTSVENPWRLPPSSQTTTFP<br>LSSYSPQLGATSDLGQNNSSNNNSGVKAEGQQQQQPLSFPGCGDFGSGDSAKQENQTLRPFFDEWPKTRDS<br>WSDLTDDNSNVASFSATQLSISIPMTSSDFSAASSQSPNGMLFAGEMYAAAAMQQQHLMQMNQSMMGG<br>YASSTTATTDLIQQYLDENKQLILAILDNQNNGKVEECARNQAKLQQNLMYLAAIADSQPPQTASLSQYPSNL<br>MMQSGPRYMQQQSAQMMSPQSLMAARSSMMYAQQAMSPLQQQQQQQQHQAAAHGQLGMSSGATT<br>GFNLLHGEASMGGGGGATGNSMMNASVFSDYGRGGSGAKEGSTSLSADARGANSGAHSGDGEYLKGTEEE<br>GS<br><br>SEQ ID NO: 28 mTaGRF4-TaGIF1<br>MAMPYASLSPAGDRRSSPAATATASLLPFCRSSPFSAGGNGGMGEEARMDGRWMARPVPFTAAQYEEL<br>EHQALIYKYLVAGVSVPPDLVLPIRRGIESLAARFYHNPLAIGYGSYLGKKVDPEPGRCRRTDGKKWRCAKEAAS<br>DSKYCERHMHRGRNRSRKPVETQLVSHSQPPAASVVPPLATGFHNHSLYPAIGGTNGGGGGNNGMSMPG<br>TFSSALGPPQQHMGNNAASPYAALGGAGTCKDFRYTAYGIRSLADEQSQLMTEAMNTSVENPWRLPPSSQT<br>TTFPLSSYSPQLGATSDLGQNNSSNNNSGVKAEGQQQQQPLSFPGCGDFGSGDSAKQENQTLRPFFDEWPK<br>TRDSWSDLTDDNSNVASFSATQLSISIPMTSSDFSAASSQSPNGMLFAGEMYAAAAMQQQHLMQMNQSM<br>MGGYASSTTATTDLIQQYLDENKQLILAILDNQNNGKVEECARNQAKLQQNLMYLAAIADSQPPQTASLSQY<br>PSNLMMQSGPRYMQQQSAQMMSPQSLMAARSSMMYAQQAMSPLQQQQQQQQHQAAAHGQLGMSS<br>GATTGFNLLHGEASMGGGGGATGNSMMNASVFSDYGRGGSGAKEGSTSLSADARGANSGAHSGDGEYLKG<br>TEEEGS |

What we claimed is:

1. A method for improving plant cell regeneration efficiency, the method comprising:
   (a) introducing into a cell of the plant
      i) an expression construct comprising a coding nucleic acid sequence of WUS, an expression construct comprising a coding nucleic acid sequence of BBM, and an expression construct comprising a nucleic acid sequence of SERK, wherein the WUS comprises the amino acid sequence shown in SEQ ID NO: 1, the BBM comprises the amino acid sequence shown in SEQ ID NO: 2, or the SERK comprises the amino acid sequence shown in SEQ ID NO: 3; and/or
      ii) an expression construct comprising a coding nucleic acid sequence of GRF and an expression construct comprising a coding nucleic acid sequence of GIF, wherein the GRF comprises the amino acid sequence of SEQ ID NO: 7 and the GIF1 comprises the amino acid sequence shown in SEQ ID NO: 11; and/or
      iii) an expression construct comprising the nucleotide sequence of SEQ ID NO: 22;
   (b) regenerating an intact plant from the plant cell.

2. A method of transforming at least one exogenous nucleic acid sequence of interest into a plant, the method comprising:
   (a) introducing into a cell of the plant
      i) an expression construct comprising a coding nucleic acid sequence of WUS, an expression construct comprising a coding nucleic acid sequence of BBM and an expression construct comprising a coding nucleic acid sequence of SERK, wherein the WUS comprises the amino acid sequence shown in SEQ ID NO: 1, the BBM comprises the amino acid sequence shown in SEQ ID NO: 2, or the SERK comprises the amino acid sequence shown in SEQ ID NO: 3; and/or
      ii) an expression construct comprising a coding nucleic acid sequence of GRF and an expression construct comprising a coding nucleic acid sequence of GIF, wherein the GRF comprises the amino acid sequence of SEQ ID NO: 7, and the GIF1 comprises the amino acid sequence shown in SEQ ID NO: 11; and/or
      iii) an expression construct comprising the nucleotide sequence of SEQ ID NO: 22;
   (b) introducing at least one expression construct comprising the at least one exogenous nucleic acid sequence of interest into the plant cell; and
   (c) regenerating an intact plant from the plant cell.

3. A method for gene editing in a plant, the method comprising:
   (a) introducing into a cell of the plant
      i) an expression construct comprising a coding nucleic acid sequence of WUS, an expression construct comprising a coding nucleic acid sequence of BBM and an expression construct comprising a coding nucleic acid sequence of SERK, wherein the WUS comprises the amino acid sequence shown in SEQ ID NO: 1, the BBM comprises the amino acid sequence shown in SEQ ID NO: 2, or the SERK comprises the amino acid sequence shown in SEQ ID NO: 3; and/or
      ii) an expression construct comprising a coding nucleic acid sequence of GRF and an expression construct comprising a coding nucleic acid sequence of GIF, wherein the GRF comprises the amino acid sequence of SEQ ID NO: 7, and the GIF1 comprises the amino acid sequence shown in SEQ ID NO: 11; and/or
      iii) an expression construct comprising the nucleotide sequence of SEQ ID NO: 22;
   (b) introducing at least one expression construct comprising the at least one exogenous nucleic acid sequence of interest into the plant cell, wherein the at least one exogenous nucleic acid sequence of interest encodes a component of a gene editing system; or introducing at least one component of the gene editing system into the plant cell; and
   (c) regenerating an intact plant from the plant cell.

4. The method according to any one of claims 1-3, wherein the coding nucleic acid sequence of WUS, the coding nucleic acid sequence of BBM and the coding nucleic acid sequence of SERK are placed in a same expression construct.

5. The method according to claim 4, wherein the coding nucleic acid sequence of WUS, the coding nucleic acid sequence of BBM, the coding nucleic acid sequence of SERK, and the at least one exogenous nucleic acid sequence of interest, if present, are placed in a same expression construct.

6. The method according to any one of claims 1-3, wherein the coding nucleic acid sequence of GRF and the coding nucleic acid sequence of GIF are placed in a same expression construct.

7. The method according to claim 6, wherein the coding nucleic acid sequence of GRF the coding nucleic acid sequence of GIF and the at least one exogenous nucleic acid sequence of interest, if present, are placed in a same expression construct.

8. The method according to any one of claims 1-3, wherein the GRF comprises a mutated miRNA binding site, so as not to be regulated by the miRNA, wherein the miRNA is miR396.

9. The method according to any one of claims 1-3, wherein the GRF is fused to the GIF by a linker, and further wherein the linker comprises an amino acid sequence comprising SEQ ID NO: 12.

10. The method according to claim 3, wherein the gene editing system is selected from the group consisting of CRISPR system, TALEN, meganuclease and zinc finger nuclease.

11. The method according to claim 10, wherein the gene editing system is a base editing system.

12. The method according to claim 3, wherein the gene editing system is a base editor comprising an amino acid sequence comprising SEQ ID NO: 14.

* * * * *

SEQUENCE LISTING

<160> NUMBER OF SEQ ID NOS: 68

<210> SEQ ID NO 1
<211> LENGTH: 302
<212> TYPE: PRT
<213> ORGANISM: Zea mays

<400> SEQUENCE: 1

Met Ala Ala Asn Ala Gly Gly Gly Ala Gly Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Pro Pro Ser Gly Ala Ala
        115                 120                 125

Pro Pro Ser Pro Thr Leu Gly Phe Tyr Ala Ala Gly Asn Gly Gly
    130                 135                 140

Ser Ala Val Leu Leu Asp Thr Ser Ser Asp Trp Gly Ser Ser Gly Ala
145                 150                 155                 160

```
Ala Met Ala Thr Glu Thr Cys Phe Leu Gln Asp Tyr Met Gly Val Thr
            165                 170                 175

Asp Thr Gly Ser Ser Gln Trp Pro Arg Phe Ser Ser Asp Thr
        180                 185                 190

Ile Met Ala Ala Ala Ala Arg Ala Ala Thr Thr Arg Ala Pro Glu
        195                 200                 205

Thr Leu Pro Leu Phe Pro Thr Cys Gly Asp Gly Gly Ser Gly Ser
        210                 215                 220

Ser Ser Tyr Leu Pro Phe Trp Gly Ala Ala Ser Thr Thr Ala Gly Ala
225                 230                 235                 240

Thr Ser Ser Val Ala Ile Gln Gln Gln His Gln Leu Gln Glu Gln Tyr
                245                 250                 255

Ser Phe Tyr Ser Asn Ser Asn Ser Thr Gln Leu Ala Gly Thr Gly Asn
                260                 265                 270

Gln Asp Val Ser Ala Thr Ala Ala Ala Ala Ala Leu Glu Leu Ser
            275                 280                 285

Leu Ser Ser Trp Cys Ser Pro Tyr Pro Ala Ala Gly Ser Met
        290                 295                 300

<210> SEQ ID NO 2
<211> LENGTH: 710
<212> TYPE: PRT
<213> ORGANISM: Zea mays

<400> SEQUENCE: 2

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
                20                  25                  30

Ala Asp His Val Ser Gly Asp Val Cys Phe Asn Ile Pro Gln Asp Trp
            35                  40                  45

Ser Met Arg Gly Ser Glu Leu Ser Ala Leu Val Ala Glu Pro Lys Leu
        50                  55                  60

Glu Asp Phe Leu Gly Gly Ile Ser Phe Ser Glu Gln His His Lys Ala
65                  70                  75                  80

Asn Cys Asn Met Ile Pro Ser Thr Ser Ser Thr Val Cys Tyr Ala Ser
                85                  90                  95

Ser Gly Ala Ser Thr Gly Tyr His His Gln Leu Tyr His Gln Pro Thr
            100                 105                 110

Ser Ser Ala Leu His Phe Ala Asp Ser Val Met Val Ala Ser Ser Ala
        115                 120                 125

Gly Val His Asp Gly Gly Ala Met Leu Ser Ala Ala Ala Ala Asn Gly
    130                 135                 140

Val Ala Gly Ala Ala Ser Ala Asn Gly Gly Ile Gly Leu Ser Met
145                 150                 155                 160

Ile Lys Asn Trp Leu Arg Ser Gln Pro Ala Pro Met Gln Pro Arg Val
                165                 170                 175

Ala Ala Ala Glu Gly Ala Gln Gly Leu Ser Leu Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Gly Ser Gly Val Ala Gly
225                 230                 235                 240
```

```
Ala Leu Val Ala Val Ser Thr Asp Thr Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
    450                 455                 460

Ala Ser Ala Gln His His His Ala Gly Val Val Ser Tyr Asp Val Gly
465                 470                 475                 480

Arg Ile Ala Ser Gln Leu Gly Asp Gly Gly Ala Leu Ala Ala Ala Tyr
                485                 490                 495

Gly Ala His Tyr His Gly Ala Ala Trp Pro Thr Ile Ala Phe Gln Pro
            500                 505                 510

Gly Ala Ala Ser Thr Gly Leu Tyr His Pro Tyr Ala Gln Gln Pro Met
        515                 520                 525

Arg Gly Gly Gly Trp Cys Lys Gln Glu Gln Asp His Ala Val Ile Ala
    530                 535                 540

Ala Ala His Ser Leu Gln Asp Leu His His Leu Asn Leu Gly Ala Ala
545                 550                 555                 560

Gly Ala His Asp Phe Phe Ser Ala Gly Gln Gln Ala Ala Ala Ala Ala
                565                 570                 575

Met His Gly Leu Gly Ser Ile Asp Ser Ala Ser Leu Glu His Ser Thr
            580                 585                 590

Gly Ser Asn Ser Val Val Tyr Asn Gly Gly Val Gly Asp Ser Asn Gly
        595                 600                 605

Ala Ser Ala Val Gly Gly Ser Gly Gly Gly Tyr Met Met Pro Met Ser
    610                 615                 620

Ala Ala Gly Ala Thr Thr Thr Ser Ala Met Val Ser His Glu Gln Val
625                 630                 635                 640

His Ala Arg Ala Tyr Asp Glu Ala Lys Gln Ala Gln Met Gly Tyr
                645                 650                 655
```

-continued

```
Glu Ser Tyr Leu Val Asn Ala Glu Asn Gly Gly Arg Met Ser
            660                 665             670
Ala Trp Gly Thr Val Val Ser Ala Ala Ala Ala Ala Ser Ser
        675                 680             685
Asn Asp Asn Met Ala Ala Asp Val Gly His Gly Gly Ala Gln Leu Phe
690                 695                 700
Ser Val Trp Asn Asp Thr
705             710

<210> SEQ ID NO 3
<211> LENGTH: 564
<212> TYPE: PRT
<213> ORGANISM: Zea mays

<400> SEQUENCE: 3

Met Ala Ala Ala Glu Ala Arg Arg Ser Ala Val Trp Ala Leu Leu
1               5                   10                  15
Pro Leu Leu Leu Arg Leu Leu His Pro Ala Ala Leu Val Leu Ala Asn
                20                  25                  30
Thr Glu Gly Asp Ala Leu His Ser Leu Arg Thr Asn Leu Asn Asp Pro
            35                  40                  45
Asn Asn Val Leu Gln Ser Trp Asp Pro Thr Leu Val Asn Pro Cys Thr
50                  55                  60
Trp Phe His Val Thr Cys Asn Asn Asp Asn Ser Val Ile Arg Val Asp
65                  70                  75                  80
Leu Gly Asn Ala Ala Leu Ser Gly Thr Leu Val Pro Gln Leu Gly Gln
                85                  90                  95
Leu Lys Asn Leu Gln Tyr Leu Glu Leu Tyr Ser Asn Asn Ile Ser Gly
                100                 105                 110
Thr Ile Pro Ser Glu Leu Gly Asn Leu Thr Asn Leu Val Ser Leu Asp
            115                 120                 125
Leu Tyr Leu Asn Asn Phe Thr Gly Pro Ile Pro Asp Ser Leu Gly Lys
130                 135                 140
Leu Leu Lys Leu Arg Phe Leu Arg Leu Asn Asn Asn Ser Leu Ser Gly
145                 150                 155                 160
Ser Ile Pro Lys Ser Leu Thr Ala Ile Thr Ala Leu Gln Val Leu Asp
                165                 170                 175
Leu Ser Asn Asn Asn Leu Ser Gly Glu Val Pro Ser Thr Gly Ser Phe
            180                 185                 190
Ser Leu Phe Thr Pro Ile Ser Phe Gly Asn Asn Pro Asn Leu Cys Gly
            195                 200                 205
Pro Gly Thr Thr Lys Pro Cys Pro Gly Ala Pro Pro Phe Ser Pro Pro
210                 215                 220
Pro Pro Tyr Asn Pro Thr Thr Pro Val Gln Ser Pro Gly Ser Ser Ser
225                 230                 235                 240
Ser Ser Thr Gly Ala Ile Ala Gly Gly Val Ala Ala Gly Ala Ala Leu
                245                 250                 255
Leu Phe Ala Ile Pro Ala Ile Ser Phe Ala Tyr Trp Arg Arg Arg Lys
            260                 265                 270
Pro Gln Glu His Phe Phe Asp Val Pro Ala Glu Glu Asp Pro Glu Val
            275                 280                 285
His Leu Gly Gln Leu Lys Arg Phe Ser Leu Arg Glu Leu Gln Val Ala
        290                 295                 300
Thr Asp Gly Phe Ser Asn Lys Asn Ile Leu Gly Arg Gly Gly Phe Gly
305                 310                 315                 320
```

```
Lys Val Tyr Lys Gly Arg Leu Ala Asp Gly Ser Leu Val Ala Val Lys
                325                 330                 335

Arg Leu Lys Glu Glu Arg Thr Pro Gly Gly Glu Leu Gln Phe Gln Thr
            340                 345                 350

Glu Val Glu Met Ile Ser Met Ala Val His Arg Asn Leu Leu Arg Leu
        355                 360                 365

Arg Gly Phe Cys Met Thr Pro Thr Glu Arg Leu Leu Val Tyr Pro Tyr
    370                 375                 380

Met Ala Asn Gly Ser Val Ala Ser Arg Leu Arg Asp Arg Pro Pro Ala
385                 390                 395                 400

Glu Pro Pro Leu Asp Trp Gln Thr Arg Gln Arg Ile Ala Leu Gly Ser
                405                 410                 415

Ala Arg Gly Leu Ser Tyr Leu His Asp His Cys Asp Pro Lys Ile Ile
            420                 425                 430

His Arg Asp Val Lys Ala Ala Asn Ile Leu Leu Asp Glu Asp Phe Glu
        435                 440                 445

Ala Val Val Gly Asp Phe Gly Leu Ala Lys Leu Met Asp Tyr Lys Asp
    450                 455                 460

Thr His Val Thr Thr Ala Val Arg Gly Thr Ile Gly His Ile Ala Pro
465                 470                 475                 480

Glu Tyr Leu Ser Thr Gly Lys Ser Ser Glu Lys Thr Asp Val Phe Gly
                485                 490                 495

Tyr Gly Ile Thr Leu Leu Glu Leu Ile Thr Gly Gln Arg Ala Phe Asp
            500                 505                 510

Leu Ala Arg Leu Ala Asn Asp Asp Val Met Leu Leu Asp Trp Val
        515                 520                 525

Val Asn Cys Ala Ile Ser Ser Val Gln Ile Val Pro Gln Val Phe Met
    530                 535                 540

Pro Phe Leu Trp Leu Pro Tyr Cys Ala Gly Ala Gly Ala His Leu Phe
545                 550                 555                 560

Leu Cys Asn Cys

<210> SEQ ID NO 4
<211> LENGTH: 407
<212> TYPE: PRT
<213> ORGANISM: Triticum aestivum

<400> SEQUENCE: 4

Met Ala Met Pro Tyr Ala Ser Leu Ser Pro Ala Gly Asp Arg Arg Ser
1               5                   10                  15

Ser Pro Ala Ala Thr Ala Thr Ala Ser Leu Leu Pro Phe Cys Arg Ser
                20                  25                  30

Ser Pro Phe Ser Ala Gly Gly Asn Gly Gly Met Gly Gly Glu Ala Arg
            35                  40                  45

Met Asp Gly Arg Trp Met Ala Arg Pro Val Pro Phe Thr Ala Ala Gln
        50                  55                  60

Tyr Glu Glu Leu Glu His Gln Ala Leu Ile Tyr Lys Tyr Leu Val Ala
65                  70                  75                  80

Gly Val Ser Val Pro Pro Asp Leu Val Leu Pro Ile Arg Arg Gly Ile
                85                  90                  95

Glu Ser Leu Ala Ala Arg Phe Tyr His Asn Pro Leu Ala Ile Gly Tyr
            100                 105                 110

Gly Ser Tyr Leu Gly Lys Lys Val Asp Pro Glu Pro Gly Arg Cys Arg
        115                 120                 125
```

Arg Thr Asp Gly Lys Lys Trp Arg Cys Ala Lys Glu Ala Ala Ser Asp
         130                 135                 140

Ser Lys Tyr Cys Glu Arg His Met His Arg Gly Arg Asn Arg Ser Arg
145                 150                 155                 160

Lys Pro Val Glu Thr Gln Leu Val Ser His Ser Gln Pro Pro Ala Ala
                165                 170                 175

Ser Val Val Pro Pro Leu Ala Thr Gly Phe His Asn His Ser Leu Tyr
            180                 185                 190

Pro Ala Ile Gly Gly Thr Asn Gly Gly Gly Gly Asn Asn Gly
        195                 200                 205

Met Ser Met Pro Gly Thr Phe Ser Ser Ala Leu Gly Pro Gln Gln
210                 215                 220

His Met Gly Asn Asn Ala Ala Ser Pro Tyr Ala Ala Leu Gly Gly Ala
225                 230                 235                 240

Gly Thr Cys Lys Asp Phe Arg Tyr Thr Ala Tyr Gly Ile Arg Ser Leu
                245                 250                 255

Ala Asp Glu Gln Ser Gln Leu Met Thr Glu Ala Met Asn Thr Ser Val
            260                 265                 270

Glu Asn Pro Trp Arg Leu Pro Pro Ser Ser Gln Thr Thr Thr Phe Pro
        275                 280                 285

Leu Ser Ser Tyr Ser Pro Gln Leu Gly Ala Thr Ser Asp Leu Gly Gln
290                 295                 300

Asn Asn Ser Ser Asn Asn Ser Gly Val Lys Ala Glu Gly Gln Gln
305                 310                 315                 320

Gln Gln Gln Pro Leu Ser Phe Pro Gly Cys Gly Asp Phe Gly Ser Gly
                325                 330                 335

Asp Ser Ala Lys Gln Glu Asn Gln Thr Leu Arg Pro Phe Phe Asp Glu
            340                 345                 350

Trp Pro Lys Thr Arg Asp Ser Trp Ser Asp Leu Thr Asp Asp Asn Ser
        355                 360                 365

Asn Val Ala Ser Phe Ser Ala Thr Gln Leu Ser Ile Ser Ile Pro Met
370                 375                 380

Thr Ser Ser Asp Phe Ser Ala Ala Ser Ser Gln Ser Pro Asn Gly Met
385                 390                 395                 400

Leu Phe Ala Gly Glu Met Tyr
                405

<210> SEQ ID NO 5
<211> LENGTH: 407
<212> TYPE: PRT
<213> ORGANISM: Artificial Sequence
<220> FEATURE:
<223> OTHER INFORMATION: miR396 binding site mutated TaGRF4 amino acid
      sequence

<400> SEQUENCE: 5

Met Ala Met Pro Tyr Ala Ser Leu Ser Pro Ala Gly Asp Arg Arg Ser
1               5                   10                  15

Ser Pro Ala Ala Thr Ala Thr Ala Ser Leu Leu Pro Phe Cys Arg Ser
            20                  25                  30

Ser Pro Phe Ser Ala Gly Gly Asn Gly Gly Met Gly Glu Glu Ala Arg
        35                  40                  45

Met Asp Gly Arg Trp Met Ala Arg Pro Val Pro Phe Thr Ala Ala Gln
50                  55                  60

Tyr Glu Glu Leu Glu His Gln Ala Leu Ile Tyr Lys Tyr Leu Val Ala

```
            65                  70                  75                  80
Gly Val Ser Val Pro Asp Leu Val Leu Pro Ile Arg Arg Gly Ile
                85                  90                  95

Glu Ser Leu Ala Ala Arg Phe Tyr His Asn Pro Leu Ala Ile Gly Tyr
            100                 105                 110

Gly Ser Tyr Leu Gly Lys Lys Val Asp Pro Glu Pro Gly Arg Cys Arg
        115                 120                 125

Arg Thr Asp Gly Lys Lys Trp Arg Cys Ala Lys Glu Ala Ala Ser Asp
    130                 135                 140

Ser Lys Tyr Cys Glu Arg His Met His Arg Gly Arg Asn Arg Ser Arg
145                 150                 155                 160

Lys Pro Val Glu Thr Gln Leu Val Ser His Ser Gln Pro Ala Ala
                165                 170                 175

Ser Val Val Pro Pro Leu Ala Thr Gly Phe His Asn His Ser Leu Tyr
            180                 185                 190

Pro Ala Ile Gly Gly Thr Asn Gly Gly Gly Gly Gly Asn Asn Gly
        195                 200                 205

Met Ser Met Pro Gly Thr Phe Ser Ser Ala Leu Gly Pro Gln Gln
    210                 215                 220

His Met Gly Asn Asn Ala Ala Ser Pro Tyr Ala Ala Leu Gly Gly Ala
225                 230                 235                 240

Gly Thr Cys Lys Asp Phe Arg Tyr Thr Ala Tyr Gly Ile Arg Ser Leu
                245                 250                 255

Ala Asp Glu Gln Ser Gln Leu Met Thr Glu Ala Met Asn Thr Ser Val
            260                 265                 270

Glu Asn Pro Trp Arg Leu Pro Pro Ser Ser Gln Thr Thr Phe Pro
        275                 280                 285

Leu Ser Ser Tyr Ser Pro Gln Leu Gly Ala Thr Ser Asp Leu Gly Gln
    290                 295                 300

Asn Asn Ser Ser Asn Asn Asn Ser Gly Val Lys Ala Glu Gly Gln Gln
305                 310                 315                 320

Gln Gln Gln Pro Leu Ser Phe Pro Gly Cys Gly Asp Phe Gly Ser Gly
                325                 330                 335

Asp Ser Ala Lys Gln Glu Asn Gln Thr Leu Arg Pro Phe Phe Asp Glu
            340                 345                 350

Trp Pro Lys Thr Arg Asp Ser Trp Ser Asp Leu Thr Asp Asp Asn Ser
        355                 360                 365

Asn Val Ala Ser Phe Ser Ala Thr Gln Leu Ser Ile Ser Ile Pro Met
    370                 375                 380

Thr Ser Ser Asp Phe Ser Ala Ala Ser Ser Gln Ser Pro Asn Gly Met
385                 390                 395                 400

Leu Phe Ala Gly Glu Met Tyr
                405

<210> SEQ ID NO 6
<211> LENGTH: 225
<212> TYPE: PRT
<213> ORGANISM: Triticum aestivum

<400> SEQUENCE: 6

Met Gln Gln Gln His Leu Met Gln Met Asn Gln Ser Met Met Gly Gly
1               5                   10                  15

Tyr Ala Ser Ser Thr Thr Ala Thr Asp Leu Ile Gln Gln Tyr Leu
            20                  25                  30
```

-continued

```
Asp Glu Asn Lys Gln Leu Ile Leu Ala Ile Leu Asp Asn Gln Asn Asn
             35                  40                  45

Gly Lys Val Glu Glu Cys Ala Arg Asn Gln Ala Lys Leu Gln Gln Asn
 50                  55                  60

Leu Met Tyr Leu Ala Ala Ile Ala Asp Ser Gln Pro Pro Gln Thr Ala
 65                  70                  75                  80

Ser Leu Ser Gln Tyr Pro Ser Asn Leu Met Met Gln Ser Gly Pro Arg
                 85                  90                  95

Tyr Met Gln Gln Gln Ser Ala Gln Met Met Ser Pro Gln Ser Leu Met
            100                 105                 110

Ala Ala Arg Ser Ser Met Met Tyr Ala Gln Gln Ala Met Ser Pro Leu
        115                 120                 125

Gln Gln Gln Gln Gln Gln Gln His Gln Ala Ala His Gly Gln
130                 135                 140

Leu Gly Met Ser Ser Gly Ala Thr Thr Gly Phe Asn Leu Leu His Gly
145                 150                 155                 160

Glu Ala Ser Met Gly Gly Gly Gly Ala Thr Gly Asn Ser Met Met
                165                 170                 175

Asn Ala Ser Val Phe Ser Asp Tyr Gly Arg Gly Gly Ser Gly Ala Lys
            180                 185                 190

Glu Gly Ser Thr Ser Leu Ser Ala Asp Ala Arg Gly Ala Asn Ser Gly
        195                 200                 205

Ala His Ser Gly Asp Gly Glu Tyr Leu Lys Gly Thr Glu Glu Glu Gly
    210                 215                 220

Ser
225

<210> SEQ ID NO 7
<211> LENGTH: 578
<212> TYPE: PRT
<213> ORGANISM: Glycine max

<400> SEQUENCE: 7

Met Gly Glu Leu Phe Gly Val Gly Lys Arg Arg Asn Ile Ser Ser Ser
  1               5                  10                  15

Asn Asn Asn Asn Asn Ser Ser Ser Ser Val Leu Gly Leu Asp Val
                 20                  25                  30

Lys Val Gln Gln Ser Pro Glu Ala Leu Phe His Asn Arg Met Met Met
             35                  40                  45

Met Ala His His Asn His His His Arg Pro Leu Ser Ser Pro Phe Asp
 50                  55                  60

Asn Asn Gly Asp Gly Asp Gly Pro Thr Thr Tyr Met Ser Phe Thr Asn
 65                  70                  75                  80

His Ile Asn Leu Val Ser Gly Ala Ser Ser Val Leu Gly Pro Ala Ile
                 85                  90                  95

Asp Ala Gly Cys Gly Ala Ala Pro Pro Ala Pro Val Arg Thr Leu Gln
            100                 105                 110

Pro Phe Asp Ile Ser Ser Tyr Thr Ser Ser Pro Thr Thr Thr Thr Thr
        115                 120                 125

Thr Phe Asn Phe Lys Pro Pro Ser Ala Gly Val Met Ala Ala Ser Leu
130                 135                 140

Gly Phe Pro Phe Thr Ser Ala Gln Trp Arg Glu Leu Glu Arg Gln Ala
145                 150                 155                 160

Met Ile Tyr Lys Tyr Met Met Ala Ser Val Pro Val Pro His Asp Leu
                165                 170                 175
```

```
Leu Thr Pro Ser Ser Arg Ser Ser Cys Met Asp Gly Phe Asn Leu
            180                 185                 190

Arg Leu Ala Asn Ser Thr Asp Pro Glu Pro Gly Arg Cys Arg Thr
        195                 200                 205

Asp Gly Lys Lys Trp Arg Cys Ser Arg Asp Val Ala Pro Asn His Lys
    210                 215                 220

Tyr Cys Glu Arg His Met His Arg Gly Arg Pro Arg Ser Arg Lys Pro
225                 230                 235                 240

Val Glu Val Asn Thr Asn Ser Thr Thr Pro Thr Ser Val Asn Asn
                245                 250                 255

Asn Asn His Gln Ile Lys Lys Ala Arg His Glu Cys Asn Asn Pro
            260                 265                 270

Phe Ala Thr Pro Asp Val Thr Ala Ala Ile Ser Asn Pro Thr Ser Arg
            275                 280                 285

Lys Asn Gly Ser Ser Pro His Phe Leu Gly Ser Thr Thr Gln Pro
            290                 295                 300

Tyr Leu Asp Ser Ser Leu Ser Leu Asp Asn Phe Gly Leu Lys Ala Ala
305                 310                 315                 320

Ser Phe Asp Ser Val Ala Ser Val Ser Ala Asn Lys Glu Pro Arg Gly
                325                 330                 335

Leu Glu Trp Met Leu Asn Gly Asp Pro Ile Ser Leu Gly Ala Ser Asp
                340                 345                 350

Ser Gln Trp Gln Ser Leu Met His Asn Lys Asp Gly Met Thr Ser Val
            355                 360                 365

Ser Ser Cys Asn Thr Thr Glu Ser Gln Tyr Leu Asn Ser Leu Ala Leu
            370                 375                 380

Tyr Asn Ser Gly Leu Glu Gln Gln Asn Arg Arg His Pro Leu Phe Leu
385                 390                 395                 400

Asn Pro Leu Val Val Pro Met Glu Asn Leu Gln Pro Glu Lys Pro Arg
                405                 410                 415

Gly Phe Ile Asp Ala Trp Ser Asn Ala Glu Ser Asn Ala Asn Thr Asn
                420                 425                 430

Thr Thr Asn Lys Asn Ser Ala Ala Ser Ile Gly Lys Leu Ser Leu Ser
            435                 440                 445

Ser Leu Asp Leu Ser Met Gly Gly Ala Ala Val Asn Glu Asp Val Gly
            450                 455                 460

Asn Val Asn Met Gly Leu Gly Leu Met Glu Pro Asn Gly Lys Thr His
465                 470                 475                 480

Thr Gly Thr Lys Ile Ser Leu Ser Asn Trp Gln Asn Pro Ala Pro Trp
                485                 490                 495

Val Ala Ser Ser Leu Gly Gly Pro Leu Ala Glu Val Leu Arg Ser Ser
            500                 505                 510

Thr Val Thr Ala Thr Thr Thr Asn Glu Ala Thr Ser Asn Thr Pro
            515                 520                 525

Ser Pro Ala Thr Thr Thr His Ala Glu Ser Pro Ser Gly Val Leu Gln
            530                 535                 540

Lys Thr Leu Val Ser Leu Ser Asp Ser Ser Asn Asn Ser Ser Pro Arg
545                 550                 555                 560

Val Ala Ser Ser Arg Ala Asn Ser Glu Met Ala Leu Leu Arg Phe Gln
                565                 570                 575

Ser Asn
```

<210> SEQ ID NO 8
<211> LENGTH: 345
<212> TYPE: PRT
<213> ORGANISM: Glycine max

<400> SEQUENCE: 8

```
Met Met Ser Ala Ser Ala Arg Asn Arg Ser Pro Phe Thr Gln Thr Gln
1               5                   10                  15

Trp Gln Glu Leu Glu His Gln Ala Leu Val Phe Lys Tyr Met Val Thr
            20                  25                  30

Gly Thr Pro Ile Pro Pro Asp Leu Ile Tyr Ser Ile Lys Arg Ser Leu
        35                  40                  45

Asp Thr Ser Ile Ser Ser Arg Leu Phe Pro His His Pro Ile Gly Trp
    50                  55                  60

Gly Cys Phe Glu Met Gly Phe Gly Arg Lys Val Asp Pro Glu Pro Gly
65                  70                  75                  80

Arg Cys Arg Arg Thr Asp Gly Lys Lys Trp Arg Cys Ser Lys Glu Ala
                85                  90                  95

Tyr Pro Asp Ser Lys Tyr Cys Glu Arg His Met His Arg Gly Arg Asn
            100                 105                 110

Arg Ser Arg Lys Pro Val Glu Val Ser Ser Ala Ile Ser Thr Ala Thr
        115                 120                 125

Asn Thr Ser Gln Thr Ile Pro Ser Ser Tyr Thr Arg Asn Leu Ser Leu
    130                 135                 140

Thr Asn Pro Asn Met Thr Pro Pro Ser Ser Phe Pro Phe Ser Pro Leu
145                 150                 155                 160

Pro Ser Ser Met Pro Ile Glu Ser Gln Pro Phe Ser Gln Ser Tyr Gln
                165                 170                 175

Asn Ser Ser Leu Asn Pro Phe Phe Tyr Ser Gln Ser Thr Ser Ser Arg
            180                 185                 190

Pro Pro Asp Ala Asp Phe Pro Pro Gln Asp Ala Thr Thr His Gln Leu
        195                 200                 205

Phe Met Asp Ser Gly Ser Tyr Ser His Asp Glu Lys Asn Tyr Arg His
    210                 215                 220

Val His Gly Ile Arg Glu Asp Val Asp Glu Arg Ala Phe Phe Pro Glu
225                 230                 235                 240

Ala Ser Gly Ser Ala Arg Ser Tyr Thr Glu Ser Tyr Gln Gln Leu Ser
                245                 250                 255

Met Ser Ser Tyr Lys Ser Tyr Ser Asn Ser Asn Phe Gln Asn Ile Asn
            260                 265                 270

Asp Ala Thr Thr Asn Pro Arg Gln Gln Gln Gln Gln Gln Gln Gln His
        275                 280                 285

Cys Phe Val Leu Gly Thr Asp Phe Lys Ser Thr Arg Pro Thr Lys Glu
    290                 295                 300

Lys Glu Ala Glu Thr Ala Thr Gly Gln Arg Pro Leu His Arg Phe Phe
305                 310                 315                 320

Gly Glu Trp Pro Pro Lys Asn Thr Thr Asp Ser Trp Leu Asp Leu Ala
                325                 330                 335

Ser Asn Ser Arg Ile Gln Thr Asp Glu
            340                 345
```

<210> SEQ ID NO 9
<211> LENGTH: 341
<212> TYPE: PRT
<213> ORGANISM: Glycine max

```
<400> SEQUENCE: 9

Met Asn Asn Ser Ser Gly Gly Gly Arg Gly Thr Leu Met Gly Leu
1               5                   10                  15

Ser Asn Gly Tyr Cys Gly Arg Ser Pro Phe Thr Val Ser Gln Trp Gln
            20                  25                  30

Glu Leu Glu His Gln Ala Leu Ile Phe Lys Tyr Met Leu Ala Gly Leu
                35                  40                  45

Pro Val Pro Leu Asp Leu Val Phe Pro Ile Gln Asn Ser Phe His Ser
        50                  55                  60

Thr Ile Ser Leu Ser His Ala Phe Phe His His Pro Thr Leu Ser Tyr
65                  70                  75                  80

Cys Ser Phe Tyr Gly Lys Lys Val Asp Pro Glu Pro Gly Arg Cys Arg
                85                  90                  95

Arg Thr Asp Gly Lys Lys Trp Arg Cys Ser Lys Glu Ala Tyr Pro Asp
            100                 105                 110

Ser Lys Tyr Cys Glu Arg His Met His Arg Gly Arg Asn Arg Ser Arg
        115                 120                 125

Lys Pro Val Glu Ser Gln Thr Met Thr His Ser Ser Thr Val Thr
    130                 135                 140

Ser Leu Thr Val Thr Gly Gly Ser Gly Ala Ser Lys Gly Thr Val Asn
145                 150                 155                 160

Phe Gln Asn Leu Ser Thr Asn Thr Phe Gly Asn Leu Gln Gly Thr Asp
                165                 170                 175

Ser Gly Thr Asp His Thr Asn Tyr His Leu Asp Ser Ile Pro Tyr Ala
            180                 185                 190

Ile Pro Ser Lys Glu Tyr Arg Tyr Val Gln Gly Leu Lys Ser Glu Gly
        195                 200                 205

Gly Glu His Cys Phe Phe Ser Glu Ala Ser Gly Ser Asn Lys Val Leu
    210                 215                 220

Gln Met Glu Ser Gln Leu Glu Asn Thr Trp Pro Leu Met Ser Thr Arg
225                 230                 235                 240

Val Ala Ser Phe Ser Thr Ser Lys Ser Ser Asn Asp Ser Leu Leu His
                245                 250                 255

Ser Asp Tyr Pro Arg His Ser Phe Leu Ser Gly Glu Tyr Val Ser Gly
            260                 265                 270

Glu His Val Lys Glu Gly Gln Pro Leu Arg Pro Phe Phe Asn Glu
        275                 280                 285

Trp Pro Lys Ser Arg Glu Ser Trp Ser Gly Leu Glu Asp Glu Arg Ser
    290                 295                 300

Asn Gln Thr Ala Phe Ser Thr Thr Gln Leu Ser Ile Ser Ile Pro Met
305                 310                 315                 320

Ser Ser Asn Phe Ser Ala Thr Ser Ser Gln Ser Pro His Gly Glu Asp
                325                 330                 335

Glu Ile Gln Phe Arg
            340

<210> SEQ ID NO 10
<211> LENGTH: 600
<212> TYPE: PRT
<213> ORGANISM: Glycine max

<400> SEQUENCE: 10

Met Asp Leu Gly Val Val Gly Leu Glu Gly Val Val Gly Ser Glu Ser
1               5                   10                  15
```

Gly Cys Val Phe Gly Ser Ser Leu Val Ser Asp Pro Glu Thr Lys His
            20                  25                  30

Lys Trp Tyr Gly Ser Gly Leu Leu Lys Gln Glu Arg Ser Ala Ile Ala
            35                  40                  45

Thr Glu Asp Asp Glu Trp Arg Ile Ser Lys Val Ala Lys Thr Asp His
50                  55                  60

Asp Met Ser Ser Ala Ser Lys Ala Met Leu Phe Gln Gln Arg Asn Asn
65                  70                  75                  80

Ser Leu Leu Arg Ser Asn Asn Ala Thr Leu Phe Ser Asp Gly His His
            85                  90                  95

Gln Ser Gln Met Leu Ser Phe Ser Ser Pro Lys Ser Asp Ser Leu Leu
            100                 105                 110

Ile Asp Lys Ala Ser Ser Asn Ala Thr Leu Pro Phe Ser Ser His Gln
            115                 120                 125

Leu Ser Ser Tyr Thr Arg Asn Thr Gly Tyr Asn Ser Gly Ser Ile Ser
            130                 135                 140

Met His Gly Ala Leu Ala Ser Val Arg Gly Pro Phe Thr Pro Ser Gln
145                 150                 155                 160

Trp Met Glu Leu Glu His Gln Ala Leu Ile Tyr Lys Tyr Ile Thr Ala
            165                 170                 175

Asn Val Pro Val Pro Thr His Leu Leu Ile Pro Ile Arg Lys Ala Leu
            180                 185                 190

Asp Ser Val Gly Phe Cys Asn Phe Ser Ala Gly Leu Leu Arg Pro Asn
            195                 200                 205

Ser Leu Gly Trp Gly Gly Phe His Leu Gly Phe Ser Asn Asn Thr Asp
210                 215                 220

Pro Glu Pro Gly Arg Cys Arg Arg Thr Asp Gly Lys Lys Trp Arg Cys
225                 230                 235                 240

Ser Arg Asp Ala Val Val Asp Gln Lys Tyr Cys Glu Arg His Met Asn
            245                 250                 255

Arg Gly Arg His Arg Ser Arg Lys Pro Val Glu Gly Gln Ser Gly His
            260                 265                 270

Ala Leu Thr Thr Thr Thr Ser Asn Thr Pro Asn Ala Ser Ser Asn Ser
            275                 280                 285

Val Val Pro Gly Asn Asn Asn Thr Phe Ala His Asn Asn Val His
            290                 295                 300

His Pro Ile Pro Pro His Ser Ser Pro Val Asn Thr Ile Thr Arg Met
305                 310                 315                 320

Phe Thr Ser Asn Lys Glu Asn Asn Ser Thr Ser Glu Arg Met Gln
            325                 330                 335

Asp Pro Ala Leu Pro Met Leu Pro Pro Thr Leu Glu Leu Lys Pro Lys
            340                 345                 350

Glu Asn Asn Pro Phe Met Ile His Lys His Gln Ile Pro Ser Asp Glu
            355                 360                 365

Tyr Ser Ser Arg Asn Asn Asn Glu Phe Gly Leu Val Thr Ser Asp Ser
            370                 375                 380

Leu Leu Asn Pro Ser Glu Lys Arg Ser Phe Thr Ser Ser Gln Lys Asn
385                 390                 395                 400

Asp Ser Ser Glu Ser Gln Gln Gln His Ser Leu Arg His Phe Ile Asp
            405                 410                 415

Asp Ser Pro Lys Pro Gln Ser Asn His His Arg Ser Ser Ser Ile
            420                 425                 430

Trp Pro Glu Leu Asp Asn Met Gln Ser Asp Arg Thr Gln Leu Ser Ile

```
                435                 440                 445
Ser Ile Pro Ile Ser Ser Asp His Phe Met Ser Phe Thr Thr Ser
    450                 455                 460

Leu Pro Ser Asn Glu Lys Leu Thr Leu Ser Pro Leu Arg Leu Ser Arg
465                 470                 475                 480

Glu Leu Asp Pro Ile Gln Met Gly Leu Gly Val Gly Ser Ala Pro Asn
                485                 490                 495

Glu Ala Asn Thr Arg Gln Ala Asn Trp Ile Pro Ile Thr Trp Glu Ser
                500                 505                 510

Ser Met Gly Gly Pro Leu Gly Glu Val Leu Asn Leu Ser Asn Asn Asn
            515                 520                 525

Asn Ser Asn Ala Ser Asp Gln Cys Gly Lys Asn Asn Asn Thr Ser
530                 535                 540

Ala Leu Asn Leu Met Lys Asp Gly Trp Asp Asn Asn Pro Pro Ser Gly
545                 550                 555                 560

Ser Ser Pro Thr Gly Val Leu Gln Lys Ser Ala Phe Gly Ser Leu Ser
                565                 570                 575

Asn Ser Ser Ala Gly Ser Ser Pro Arg Gly Ala Glu Asn Asn Lys Glu
            580                 585                 590

Gly Ala Thr Leu Cys Asn Ala Leu
            595                 600

<210> SEQ ID NO 11
<211> LENGTH: 257
<212> TYPE: PRT
<213> ORGANISM: Glycine max

<400> SEQUENCE: 11

Met Phe Gly Ser Leu Phe His Phe Pro His Cys Leu Leu His Val Leu
1               5                   10                  15

His Gln Ser Phe Tyr Asp Ala Cys Phe Ser Gln Arg Tyr Leu Arg Ser
                20                  25                  30

His Phe Leu Thr Phe Gln Ile Thr Met Ser Glu Ser Glu Tyr Ala Leu
            35                  40                  45

Phe Gly Asp His Lys Pro Ser Pro Tyr Gln Asn Tyr Leu Asp Glu Asn
        50                  55                  60

Lys Ser Leu Ile Leu Lys Ile Val Glu Ser Gln Asn Ser Gly Lys Leu
65                  70                  75                  80

Ser Glu Cys Ala Glu Asn Gln Ala Arg Leu Gln Arg Asn Leu Met Tyr
                85                  90                  95

Leu Ala Ala Ile Ala Asp Ser Gln Pro Gln Pro Thr Met Pro Gly
            100                 105                 110

Gln Tyr Pro Pro Ser Gly Met Met Gln Gln Gly Ala His Tyr Met Gln
        115                 120                 125

Ala Gln Gln Gln Thr Gln Gln Met Ser Pro Gln Gln Leu Met Ala Ala
    130                 135                 140

Arg Ser Ser Leu Leu Tyr Ala Gln Gln Pro Tyr Ser Ala Leu Gln Gln
145                 150                 155                 160

Gln Gln Ala Met His Ser Ala Leu Gly Ser Ser Ser Gly Leu His Met
                165                 170                 175

Leu Gln Ser Glu Gly Ser Asn Val Asn Val Gly Ser Gly Ser Gly Ser
            180                 185                 190

Val Gly Gly Gly Phe Pro Asp Leu Val Arg Gly Gly Gly Gly Gly
        195                 200                 205
```

```
Gly Ser Thr Gly Glu Gly Leu His Ser Gly Arg Gly Ile Met Gly
    210                 215                 220

Ser Ser Lys Gln Glu Ile Gly Ser Ser Glu Gly Arg Gly Gly
225                 230                 235                 240

Ser Ser Glu Gly Gly Glu Asn Leu Tyr Leu Lys Ile Ala Asp Asp Gly
                245                 250                 255

Asn

<210> SEQ ID NO 12
<211> LENGTH: 4
<212> TYPE: PRT
<213> ORGANISM: Artificial Sequence
<220> FEATURE:
<223> OTHER INFORMATION: linkerA

<400> SEQUENCE: 12

Ala Ala Ala Ala
1

<210> SEQ ID NO 13
<211> LENGTH: 4
<212> TYPE: PRT
<213> ORGANISM: Artificial Sequence
<220> FEATURE:
<223> OTHER INFORMATION: linkerS

<400> SEQUENCE: 13

Ser Gly Gly Ser
1

<210> SEQ ID NO 14
<211> LENGTH: 1701
<212> TYPE: PRT
<213> ORGANISM: Artificial Sequence
<220> FEATURE:
<223> OTHER INFORMATION: A3A base editor amino acid sequence

<400> SEQUENCE: 14

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175
```

```
Asp Gly Leu Asp Glu His Ser Gln Ala Leu Ser Gly Arg Leu Arg Ala
            180                 185                 190

Ile Leu Gln Asn Gln Gly Asn Ser Gly Ser Glu Thr Pro Gly Thr Ser
        195                 200                 205

Glu Ser Ala Thr Pro Glu Ser Leu Lys Asp Lys Lys Tyr Ser Ile Gly
    210                 215                 220

Leu Ala Ile Gly Thr Asn Ser Val Gly Trp Ala Val Ile Thr Asp Glu
225                 230                 235                 240

Tyr Lys Val Pro Ser Lys Lys Phe Lys Val Leu Gly Asn Thr Asp Arg
                245                 250                 255

His Ser Ile Lys Lys Asn Leu Ile Gly Ala Leu Leu Phe Asp Ser Gly
        260                 265                 270

Glu Thr Ala Glu Ala Thr Arg Leu Lys Arg Thr Ala Arg Arg Arg Tyr
    275                 280                 285

Thr Arg Arg Lys Asn Arg Ile Cys Tyr Leu Gln Glu Ile Phe Ser Asn
290                 295                 300

Glu Met Ala Lys Val Asp Asp Ser Phe Phe His Arg Leu Glu Glu Ser
305                 310                 315                 320

Phe Leu Val Glu Glu Asp Lys Lys His Glu Arg His Pro Ile Phe Gly
                325                 330                 335

Asn Ile Val Asp Glu Val Ala Tyr His Glu Lys Tyr Pro Thr Ile Tyr
            340                 345                 350

His Leu Arg Lys Lys Leu Val Asp Ser Thr Asp Lys Ala Asp Leu Arg
        355                 360                 365

Leu Ile Tyr Leu Ala Leu Ala His Met Ile Lys Phe Arg Gly His Phe
370                 375                 380

Leu Ile Glu Gly Asp Leu Asn Pro Asp Asn Ser Asp Val Asp Lys Leu
385                 390                 395                 400

Phe Ile Gln Leu Val Gln Thr Tyr Asn Gln Leu Phe Glu Glu Asn Pro
                405                 410                 415

Ile Asn Ala Ser Gly Val Asp Ala Lys Ala Ile Leu Ser Ala Arg Leu
            420                 425                 430

Ser Lys Ser Arg Arg Leu Glu Asn Leu Ile Ala Gln Leu Pro Gly Glu
        435                 440                 445

Lys Lys Asn Gly Leu Phe Gly Asn Leu Ile Ala Leu Ser Leu Gly Leu
    450                 455                 460

Thr Pro Asn Phe Lys Ser Asn Phe Asp Leu Ala Glu Asp Ala Lys Leu
465                 470                 475                 480

Gln Leu Ser Lys Asp Thr Tyr Asp Asp Asp Leu Asp Asn Leu Leu Ala
                485                 490                 495

Gln Ile Gly Asp Gln Tyr Ala Asp Leu Phe Leu Ala Ala Lys Asn Leu
            500                 505                 510

Ser Asp Ala Ile Leu Leu Ser Asp Ile Leu Arg Val Asn Thr Glu Ile
        515                 520                 525

Thr Lys Ala Pro Leu Ser Ala Ser Met Ile Lys Arg Tyr Asp Glu His
    530                 535                 540

His Gln Asp Leu Thr Leu Leu Lys Ala Leu Val Arg Gln Gln Leu Pro
545                 550                 555                 560

Glu Lys Tyr Lys Glu Ile Phe Phe Asp Gln Ser Lys Asn Gly Tyr Ala
                565                 570                 575

Gly Tyr Ile Asp Gly Gly Ala Ser Gln Glu Glu Phe Tyr Lys Phe Ile
            580                 585                 590
```

```
Lys Pro Ile Leu Glu Lys Met Asp Gly Thr Glu Glu Leu Val Lys
            595                 600                 605

Leu Asn Arg Glu Asp Leu Leu Arg Lys Gln Arg Thr Phe Asp Asn Gly
610                 615                 620

Ser Ile Pro His Gln Ile His Leu Gly Glu Leu His Ala Ile Leu Arg
625                 630                 635                 640

Arg Gln Glu Asp Phe Tyr Pro Phe Leu Lys Asp Asn Arg Glu Lys Ile
                645                 650                 655

Glu Lys Ile Leu Thr Phe Arg Ile Pro Tyr Tyr Val Gly Pro Leu Ala
            660                 665                 670

Arg Gly Asn Ser Arg Phe Ala Trp Met Thr Arg Lys Ser Glu Glu Thr
        675                 680                 685

Ile Thr Pro Trp Asn Phe Glu Glu Val Val Asp Lys Gly Ala Ser Ala
        690                 695                 700

Gln Ser Phe Ile Glu Arg Met Thr Asn Phe Asp Lys Asn Leu Pro Asn
705                 710                 715                 720

Glu Lys Val Leu Pro Lys His Ser Leu Leu Tyr Glu Tyr Phe Thr Val
                725                 730                 735

Tyr Asn Glu Leu Thr Lys Val Lys Tyr Val Thr Glu Gly Met Arg Lys
            740                 745                 750

Pro Ala Phe Leu Ser Gly Glu Gln Lys Lys Ala Ile Val Asp Leu Leu
        755                 760                 765

Phe Lys Thr Asn Arg Lys Val Thr Val Lys Gln Leu Lys Glu Asp Tyr
770                 775                 780

Phe Lys Lys Ile Glu Cys Phe Asp Ser Val Glu Ile Ser Gly Val Glu
785                 790                 795                 800

Asp Arg Phe Asn Ala Ser Leu Gly Thr Tyr His Asp Leu Leu Lys Ile
                805                 810                 815

Ile Lys Asp Lys Asp Phe Leu Asp Asn Glu Glu Asn Glu Asp Ile Leu
            820                 825                 830

Glu Asp Ile Val Leu Thr Leu Thr Leu Phe Glu Asp Arg Glu Met Ile
        835                 840                 845

Glu Glu Arg Leu Lys Thr Tyr Ala His Leu Phe Asp Asp Lys Val Met
850                 855                 860

Lys Gln Leu Lys Arg Arg Arg Tyr Thr Gly Trp Gly Arg Leu Ser Arg
865                 870                 875                 880

Lys Leu Ile Asn Gly Ile Arg Asp Lys Gln Ser Gly Lys Thr Ile Leu
                885                 890                 895

Asp Phe Leu Lys Ser Asp Gly Phe Ala Asn Arg Asn Phe Met Gln Leu
            900                 905                 910

Ile His Asp Asp Ser Leu Thr Phe Lys Glu Asp Ile Gln Lys Ala Gln
        915                 920                 925

Val Ser Gly Gln Gly Asp Ser Leu His Glu His Ile Ala Asn Leu Ala
930                 935                 940

Gly Ser Pro Ala Ile Lys Lys Gly Ile Leu Gln Thr Val Lys Val Val
945                 950                 955                 960

Asp Glu Leu Val Lys Val Met Gly Arg His Lys Pro Glu Asn Ile Val
                965                 970                 975

Ile Glu Met Ala Arg Glu Asn Gln Thr Thr Gln Lys Gly Gln Lys Asn
            980                 985                 990

Ser Arg Glu Arg Met Lys Arg Ile  Glu Glu Gly Ile Lys  Glu Leu Gly
        995                 1000                1005

Ser Gln  Ile Leu Lys Glu His  Pro Val Glu Asn Thr  Gln Leu Gln
```

-continued

```
            1010                1015                1020
Asn Glu Lys Leu Tyr Leu Tyr Tyr Leu Gln Asn Gly Arg Asp Met
    1025                1030                1035
Tyr Val Asp Gln Glu Leu Asp Ile Asn Arg Leu Ser Asp Tyr Asp
    1040                1045                1050
Val Asp His Ile Val Pro Gln Ser Phe Leu Lys Asp Asp Ser Ile
    1055                1060                1065
Asp Asn Lys Val Leu Thr Arg Ser Asp Lys Asn Arg Gly Lys Ser
    1070                1075                1080
Asp Asn Val Pro Ser Glu Glu Val Val Lys Lys Met Lys Asn Tyr
    1085                1090                1095
Trp Arg Gln Leu Leu Asn Ala Lys Leu Ile Thr Gln Arg Lys Phe
    1100                1105                1110
Asp Asn Leu Thr Lys Ala Glu Arg Gly Gly Leu Ser Glu Leu Asp
    1115                1120                1125
Lys Ala Gly Phe Ile Lys Arg Gln Leu Val Glu Thr Arg Gln Ile
    1130                1135                1140
Thr Lys His Val Ala Gln Ile Leu Asp Ser Arg Met Asn Thr Lys
    1145                1150                1155
Tyr Asp Glu Asn Asp Lys Leu Ile Arg Glu Val Lys Val Ile Thr
    1160                1165                1170
Leu Lys Ser Lys Leu Val Ser Asp Phe Arg Lys Asp Phe Gln Phe
    1175                1180                1185
Tyr Lys Val Arg Glu Ile Asn Asn Tyr His His Ala His Asp Ala
    1190                1195                1200
Tyr Leu Asn Ala Val Val Gly Thr Ala Leu Ile Lys Lys Tyr Pro
    1205                1210                1215
Lys Leu Glu Ser Glu Phe Val Tyr Gly Asp Tyr Lys Val Tyr Asp
    1220                1225                1230
Val Arg Lys Met Ile Ala Lys Ser Glu Gln Glu Ile Gly Lys Ala
    1235                1240                1245
Thr Ala Lys Tyr Phe Phe Tyr Ser Asn Ile Met Asn Phe Phe Lys
    1250                1255                1260
Thr Glu Ile Thr Leu Ala Asn Gly Glu Ile Arg Lys Arg Pro Leu
    1265                1270                1275
Ile Glu Thr Asn Gly Glu Thr Gly Glu Ile Val Trp Asp Lys Gly
    1280                1285                1290
Arg Asp Phe Ala Thr Val Arg Lys Val Leu Ser Met Pro Gln Val
    1295                1300                1305
Asn Ile Val Lys Lys Thr Glu Val Gln Thr Gly Gly Phe Ser Lys
    1310                1315                1320
Glu Ser Ile Leu Pro Lys Arg Asn Ser Asp Lys Leu Ile Ala Arg
    1325                1330                1335
Lys Lys Asp Trp Asp Pro Lys Lys Tyr Gly Gly Phe Asp Ser Pro
    1340                1345                1350
Thr Val Ala Tyr Ser Val Leu Val Val Ala Lys Val Glu Lys Gly
    1355                1360                1365
Lys Ser Lys Lys Leu Lys Ser Val Lys Glu Leu Leu Gly Ile Thr
    1370                1375                1380
Ile Met Glu Arg Ser Ser Phe Glu Lys Asn Pro Ile Asp Phe Leu
    1385                1390                1395
Glu Ala Lys Gly Tyr Lys Glu Val Lys Lys Asp Leu Ile Ile Lys
    1400                1405                1410
```

```
Leu Pro Lys Tyr Ser Leu Phe Glu Leu Glu Asn Gly Arg Lys Arg
    1415                1420                1425

Met Leu Ala Ser Ala Gly Glu Leu Gln Lys Gly Asn Glu Leu Ala
    1430                1435                1440

Leu Pro Ser Lys Tyr Val Asn Phe Leu Tyr Leu Ala Ser His Tyr
    1445                1450                1455

Glu Lys Leu Lys Gly Ser Pro Glu Asp Asn Glu Gln Lys Gln Leu
    1460                1465                1470

Phe Val Glu Gln His Lys His Tyr Leu Asp Glu Ile Ile Glu Gln
    1475                1480                1485

Ile Ser Glu Phe Ser Lys Arg Val Ile Leu Ala Asp Ala Asn Leu
    1490                1495                1500

Asp Lys Val Leu Ser Ala Tyr Asn Lys His Arg Asp Lys Pro Ile
    1505                1510                1515

Arg Glu Gln Ala Glu Asn Ile Ile His Leu Phe Thr Leu Thr Asn
    1520                1525                1530

Leu Gly Ala Pro Ala Ala Phe Lys Tyr Phe Asp Thr Thr Ile Asp
    1535                1540                1545

Arg Lys Arg Tyr Thr Ser Thr Lys Glu Val Leu Asp Ala Thr Leu
    1550                1555                1560

Ile His Gln Ser Ile Thr Gly Leu Tyr Glu Thr Arg Ile Asp Leu
    1565                1570                1575

Ser Gln Leu Gly Gly Asp Lys Arg Pro Ala Ala Thr Lys Lys Ala
    1580                1585                1590

Gly Gln Ala Lys Lys Lys Thr Arg Asp Ser Gly Gly Ser Thr
    1595                1600                1605

Asn Leu Ser Asp Ile Ile Glu Lys Glu Thr Gly Lys Gln Leu Val
    1610                1615                1620

Ile Gln Glu Ser Ile Leu Met Leu Pro Glu Glu Val Glu Glu Val
    1625                1630                1635

Ile Gly Asn Lys Pro Glu Ser Asp Ile Leu Val His Thr Ala Tyr
    1640                1645                1650

Asp Glu Ser Thr Asp Glu Asn Val Met Leu Leu Thr Ser Asp Ala
    1655                1660                1665

Pro Glu Tyr Lys Pro Trp Ala Leu Val Ile Gln Asp Ser Asn Gly
    1670                1675                1680

Glu Asn Lys Ile Lys Met Leu Ser Gly Gly Ser Pro Lys Lys Lys
    1685                1690                1695

Arg Lys Val
    1700

<210> SEQ ID NO 15
<211> LENGTH: 1384
<212> TYPE: PRT
<213> ORGANISM: Streptococcus pyogenes

<400> SEQUENCE: 15

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
```

-continued

```
            50                  55                  60
Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                     85                  90                  95

Phe Phe His Arg Leu Glu Glu Ser Phe Leu Val Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
                130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480
```

```
Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895
```

```
Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
```

```
        1295               1300               1305
Ile Ile His Leu Phe Thr Leu Thr Asn Leu Gly Ala Pro Ala Ala
    1310               1315               1320

Phe Lys Tyr Phe Asp Thr Thr Ile Asp Arg Lys Arg Tyr Thr Ser
    1325               1330               1335

Thr Lys Glu Val Leu Asp Ala Thr Leu Ile His Gln Ser Ile Thr
    1340               1345               1350

Gly Leu Tyr Glu Thr Arg Ile Asp Leu Ser Gln Leu Gly Gly Asp
    1355               1360               1365

Lys Arg Pro Ala Ala Thr Lys Lys Ala Gly Gln Ala Lys Lys Lys
    1370               1375               1380

Lys

<210> SEQ ID NO 16
<211> LENGTH: 76
<212> TYPE: DNA
<213> ORGANISM: Artificial Sequence
<220> FEATURE:
<223> OTHER INFORMATION: sgRNA scaffold

<400> SEQUENCE: 16
gttttagagc tagaaatagc aagttaaaat aaggctagtc cgttatcaac ttgaaaaagt      60
ggcaccgagt cggtgc                                                     76

<210> SEQ ID NO 17
<211> LENGTH: 2517
<212> TYPE: DNA
<213> ORGANISM: Artificial Sequence
<220> FEATURE:
<223> OTHER INFORMATION: GmGRF5-GmGIF1

<400> SEQUENCE: 17
atgggtgaat tatttggcgt tggaaaaaga aggaacatca gcagcagcaa caacaacaac      60
aacagttcta gtagtagcgt tcttggggttg gatgtgaagg tgcaacagag ccctgaagca     120
ttattccata taggatgat gatgatggcg catcataatc atcaccaccg tccattgtca      180 tcacccttg ataataatgg tgatggcgat ggtcccacga cttacatgtc ttttactaat      240
catataaacc ttgttagtgg tgcttcttct gttcttggtc ctgctattga tgctggctgt      300
ggtgctgctc ctcctgcacc tgtaagaact ttgcagcctt ttgacatttc ttcttatact      360
tcttctccca ccaccactac cacaaccttc aacttcaaac ccccttcagc aggtgtgatg      420
gcggcttcgt tggggtttcc tttcacaagt gcacaatgga gggagcttga agacaagct      480 atgatataca agtacatgat ggcttctgtt cctgttccac atgatctcct cacaccctct      540
tctcgctctt cctgcatgga tgtggttttc aatctgaggt tggcaaatag cactgaccct      600
gagccaggta ggtgtagaag aacagatggt aaaaaatgga gatgttcaag agatgtggct      660
cctaaccaca agtactgtga gcgccatatg catagaggcc gtccccgttc aagaaagcct      720
gtggaagtta acaccaacag caccaccact cccactagcg tcaacaataa caaccatcaa      780
atcaaaaagg ctcgccatga gtgtaataat aatcctttg ctacacctga cgttactgcg      840
gctatttcca accccacatc cagaaaaaat ggatcttctc cccatttct tgggtctact      900 accactcagc catacctga ttcttccctc tcccttgata actttggtct aaaagctgct      960
agttttgact ccgtggcttc tgtttctgct aataaggaac ccaggggttt agagtggatg     1020
ctgaatggag atcctatttc cctgggtgct tctgactcac aatggcagtc tctgatgcac     1080
```

| | |
|---|---|
| aataaagatg gaatgaccag tgttagttcc tgtaacacca ccgagtctca gtatctgaat | 1140 |
| tcattagcac tatataactc tggactagaa caacagaata gacgccatcc tttgttcctg | 1200 |
| aaccctcttg ttgttcccat ggaaaatctc aaccggaga aaccaagggg ttttattgat | 1260 |
| gcttggtcta acgctgaaag caatgccaac accaacacca caacaagaa ctctgctgca | 1320 |
| tcaattggta aattatccct ttcttctctt gatctatcaa tgggggtgc tgctgtgaat | 1380 |
| gaagatgtgg gtaatgttaa catgggtttg ggcctaatgg agcctaatgg aaaaacgcac | 1440 |
| actggtacta aaatttctct ctccaattgg caaaacccag caccttgggt ggcttcatca | 1500 |
| cttgggggtc cactagctga agttctaagg tcaagcacag tcactgccac caccaccacc | 1560 |
| aatgaagcaa cctccaacac accctcgcca gccaccacta cacatgctga atctccatct | 1620 |
| ggggtgttgc agaaaacgct tgtttcattg tctgatagca gtaacaatag cagcccaagg | 1680 |
| gttgcatcat caagggccaa ttctgagatg gccttgctaa ggtttcaatc aaatgcggcc | 1740 |
| gctgccatgt tcgggtcttt gttccatttt ccacactgtc tactacatgt gctgcatcag | 1800 |
| agcttttatg acgcgtgctt ttctcagcgc tacctcagat cacatttctc cacctttcag | 1860 |
| atcacaatgt ctgaatccga atatgctttg tttggagatc acaaaccttc tccctatcaa | 1920 |
| aactatctgg atgagaacaa gtccttaatt ctgaagattg ttgaaagcca gaattcaggc | 1980 |
| aagcttagcg agtgtgccga gaaccaagca aggcttcaga gaaatctcat gtacttagct | 2040 |
| gcaatagctg attctcaacc ccaaccaccc accatgcctg gtcagtaccc tccgagtggg | 2100 |
| atgatgcagc agggagcaca ctacatgcag gctcaacaac agacacagca gatgtcacca | 2160 |
| caacaactaa tggcggcacg ctcgtcccct ttgtacgcac agcagccata ctcagcactt | 2220 |
| caacagcagc aagccatgca cagtgcactc gggtcgagtt caggactcca catgctgcaa | 2280 |
| agtgaaggca gcaatgtgaa tgtgggatca ggcagtggct ctgtaggagg agggtttcct | 2340 |
| gacttggtgc gcggtggtgg tggtggcggt ggctcgacag gggagggttt gcacagtggt | 2400 |
| ggaaggggta tcatgggaag tagcaagcag gaaattgggg gttcaagtga aggccgaggt | 2460 |
| gggggaagct cagagggtgg tgaaaacctt tacctcaaaa ttgccgacga tggaaaac | 2517 |

<210> SEQ ID NO 18
<211> LENGTH: 1818
<212> TYPE: DNA
<213> ORGANISM: Artificial Sequence
<220> FEATURE:
<223> OTHER INFORMATION: GmGRF6-GmGIF1

<400> SEQUENCE: 18

| | |
|---|---|
| atgatgagtg caagtgcaag aaataggtct cctttcacgc aaactcagtg gcaagagctt | 60 |
| gagcatcaag ctcttgtttt taagtacatg gttacaggaa cacccatccc accagatctc | 120 |
| atctactcta ttaaaagaag tctagacact tcaatttctt caaggctctt cccacatcat | 180 |
| ccaattgggt gggatgtttt tgaaatggga tttggcagaa aagtagaccc agagccaggg | 240 |
| aggtgcagaa gaacagatgg caagaaatgg agatgctcaa aggaggcata tccagactcc | 300 |
| aagtactgtg aaagacacat gcacagaggc agaaaccgtt caagaaagcc tgtggaagtt | 360 |
| tcttcagcaa taagcaccgc cacaaacacc tcccaaacaa tcccatcttc ttatacccga | 420 |
| aacctttcct tgaccaaccc caacatgaca ccaccctctt ccttcccttt ctctccttg | 480 |
| ccctcttcta tgcctattga gtcccaaccc ttttcccaat cctaccaaaa ctcttctctc | 540 |
| aatcccttct tctactccca atcaacctcc tctagacccc cagatgctga ttttccaccc | 600 |
| caagatgcca ccacccacca gctattcatg gactctgggt cttattcgca tgatgaaaag | 660 |

```
aattataggc atgttcatgg aataagagaa gatgtggatg agagagcttt cttcccagaa      720
gcatcaggat cagctaggag ctacactgaa tcataccagc aactatcaat gagctcctac      780
aagtcctatt caaactccaa ctttcagaac atcaatgatg ccaccaccaa cccaagacag      840
caagagcagc aacaacaaca acactgcttt gttttgggga cagacttcaa atcaacaaga      900
ccaactaaag agaaagaagc tgagacagct acgggtcaga accccttca ccgtttcttt       960 ggggagtggc caccaaagaa cacaacagat tcatggctag atcttgcttc caactccaga     1020
atccaaaccg atgaagcggc cgctgccatg ttcgggtctt tgttccattt tccacactgt     1080
ctactacatg tgctgcatca gagctttat gacgcgtgct tttctcagcg ctacctcaga      1140
tcacattttc tcacctttca gatcacaatg tctgaatccg aatatgcttt gtttggagat     1200
cacaaacctt ctccctatca aaactatctg atgagaaca agtccttaat tctgaagatt      1260
gttgaaagcc agaattcagg caagcttagc gagtgtgccg agaaccaagc aaggcttcag     1320
agaaatctca tgtacttagc tgcaatagct gattctcaac cccaaccacc accatgcct      1380 ggtcagtacc ctccgagtgg gatgatgcag cagggagcac actacatgca ggctcaacaa     1440
cagacacagc agatgtcacc acaacaacta atggcggcac gctcgtccct tttgtacgca     1500
cagcagccat actcagcact tcaacagcag caagccatgc acagtgcact cgggtcgagt     1560
tcaggactcc acatgctgca aagtgaaggc agcaatgtga atgtgggatc aggcagtggc     1620
tctgtaggag gagggtttcc tgacttggtg cgcggtggtg gtggtggcgg tggctcgaca     1680
ggggagggtt tgcacagtgg tggaagggggt atcatgggaa gtagcaagca ggaaattggg     1740
ggttcaagtg aaggccgagg tgggggaagc tcagagggtg gtgaaaacct ttacctcaaa     1800
attgccgacg atggaaac                                                   1818

<210> SEQ ID NO 19
<211> LENGTH: 1806
<212> TYPE: DNA
<213> ORGANISM: Artificial Sequence
<220> FEATURE:
<223> OTHER INFORMATION: GmGRF11-GmGIF1

<400> SEQUENCE: 19
atgaacaaca gcagtggcgg aggaggacga ggaactttga tgggtttgag taatgggtat       60
tgtgggaggt cgccattcac agtgtctcag tggcaggaac tggagcacca agctttgatc      120
ttcaagtaca tgcttgcggg tcttcctgtt cctctcgatc tcgtgttccc cattcagaac      180
agcttccact ctactatctc gctctcgcac gctttcttc accatcccac gttgagttac       240
tgttccttct atgggaagaa ggtggaccct gagccaggac gatgcaggag gactgatgga      300
aaaaagtgga ggtgctccaa ggaagcatac ccagactcca gtactgcgga gcgccacatg      360
caccgtggcc gcaaccgttc aagaaagcct gtggaatcac aaactatgac tcactcatct      420
tcaactgtca catcactcac tgtcactggg ggtagtggtg ccagcaaagg aactgtaaat      480
ttccaaaacc tttctacaaa tacctttggt aatctccagg gtaccgattc tggaactgac      540
cacaccaatt atcatctaga ttccattccc tatgcgattc caagtaaaga atacaggtat      600
gttcaaggac ttaaatctga gggtggtgag cactgcttt tttctgaagc ttctggaagc      660
aacaaggttc tccaaatgga gtcacagctg gaaaacacat ggcctttgat gtcaaccaga      720
gttgcctctt tttctacgtc aaaatcaagt aatgattccc tgttgcatag tgattatccc      780
cggcattcgt ttttatctgg tgaatatgtg tcgggagaac acgtaaagga ggagggccag     840
```

| | |
|---|---|
| cctcttcgac ctttttttaa tgaatggcct aaaagcaggg agtcatggtc tggtctagaa | 900 |
| gatgagagat ccaaccaaac agccttctcc acaactcaac tctcaatatc cattcctatg | 960 |
| tcttccaatt tctctgcaac gagctctcag tccccacatg gtgaagatga gattcaattt | 1020 |
| agggcggccg ctgccatgtt cgggtctttg ttccattttc cacactgtct actacatgtg | 1080 |
| ctgcatcaga gcttttatga cgcgtgcttt tctcagcgct acctcagatc acattttctc | 1140 |
| acctttcaga tcacaatgtc tgaatccgaa tatgctttgt ttggagatca caaaccttct | 1200 |
| ccctatcaaa actatctgga tgagaacaag tccttaattc tgaagattgt tgaaagccag | 1260 |
| aattcaggca agcttagcga gtgtgccgag aaccaagcaa ggcttcagag aaatctcatg | 1320 |
| tacttagctg caatagctga ttctcaaccc caaccaccca ccatgcctgg tcagtaccct | 1380 |
| ccgagtggga tgatgcagca gggagcacac tacatgcagg ctcaacaaca gacacagcag | 1440 |
| atgtcaccac aacaactaat ggcggcacgc tcgtcccttt tgtacgcaca gcagccatac | 1500 |
| tcagcacttc aacagcagca agccatgcac agtgcactcg gtcgagttc aggactccac | 1560 |
| atgctgcaaa gtgaaggcag caatgtgaat gtgggatcag gcagtggctc tgtaggagga | 1620 |
| gggtttcctg acttggtgcg cggtggtggt ggtggcggtg gctcgacagg ggagggtttg | 1680 |
| cacagtggtg gaagggg tat catgggaagt agcaagcagg aaattggggg ttcaagtgaa | 1740 |
| ggccgaggtg ggggaagctc agagggtggt gaaaaccttt acctcaaaat tgccgacgat | 1800 |
| ggaaac | 1806 |

<210> SEQ ID NO 20
<211> LENGTH: 2583
<212> TYPE: DNA
<213> ORGANISM: Artificial Sequence
<220> FEATURE:
<223> OTHER INFORMATION: GmGRF18-GmGIF1

<400> SEQUENCE: 20

| | |
|---|---|
| atggatcttg gggtggtggg tttggagggg gtggtgggtt cagaaagtgg ttgtgtgttt | 60 |
| ggttcttctc ttgtttcaga tcctgagaca aagcacaagt ggtacggatc tggtttgctc | 120 |
| aagcaagaga gatctgccat agctactgaa gatgatgagt ggagaatttc caaagttgct | 180 |
| aaaactgatc atgacatgtc ttcagcctcc aaagcaatgc tctttcagca agaaacaac | 240 |
| tctttgttga gatctaataa tgcaactctc ttctctgatg gtcatcacca atcacaaatg | 300 |
| ttgagcttct cttctccaaa gtcagattct tgttgatag ataaggcttc ctcaaatgcc | 360 |
| acattgcctt tttcttccca ccaattgtct agctacacca gaaatacagg ttacaattca | 420 |
| ggaagcataa gcatgcatgg ggctttggct agtgtgagag ggccattcac tccatcacag | 480 |
| tggatggagc ttgaacacca agccttgatc tacaagtaca tcacagcaaa tgttcctgtg | 540 |
| ccaactcatc ttctcattcc catcagaaaa gcacttgatt ctgttggctt ctgcaacttc | 600 |
| tcagccggac tcctcagacc caactcattg ggatggggag gtttccatct aggattctcg | 660 |
| aacaatacag accctgagcc agggaggtgt aggagaacag atggaaagaa atggcgatgt | 720 |
| tcaagagatg ccgtagtaga tcagaagtat tgcgagcggc acatgaaccg aggacgccat | 780 |
| cgttcaagaa agcctgtgga aggccaatca ggccatgccc tcaccaccac caccagtaat | 840 |
| acacctaatg cttcctccaa ctctgtggtg cctggcaaca caacaacac ctttgcacac | 900 |
| aacaatgtgc accaccctat tcctcctcat tcctctccgg tcaacaccat cactaggatg | 960 |
| tttacaagca acaaagagaa taataacagt accagtgaga ggatgcagga ccctgcactt | 1020 |
| cccatgcttc ctcccactct tgagctgaaa ccaaaggaga acaatccttt catgattcat | 1080 |

```
aaacaccaaa tcccatctga tgaatactca agtaggaaca acaatgagtt tgggcttgtc    1140
acttctgatt ctttgcttaa ccccctcagag aaaagaagct ttacttcttc acaaaagaat    1200
gattcttctg agtcccaaca acaacattcc ctcaggcact tcattgatga ctctcccaaa    1260
ccacagtcta atcatcatca tcgttcgtcg tctatatggc ctgaacttga caacatgcag    1320
tcagacagga ctcagttatc aatctccata ccaatatctt cctcagatca cttcatgtca    1380
ttcactactt ccttgccctc gaacgagaaa ctcacgttgt caccacttag ctttcaagg    1440 gagttagacc ccattcaaat ggggttggga gtgggaagtg cccccaatga agcaaacact    1500
aggcaagcca attggattcc aatcacttgg gagagttcaa tggtggtcc tcttggagag    1560 gttttgaacc ttagtaacaa taacaacagc aatgctagtg atcaatgtgg caagaacaac    1620
aacaacactt cagctctcaa cctcatgaaa gatggatggg acaataatcc tccatcaggg    1680
tcatccccaa ctggggtgct tcaaaaatct gcatttggat cactttccaa tagcagtgct    1740
gggagcagtc caaggggggc agagaacaac aaagaaggtg ccaccttgtg caatgccttg    1800
gcggccgctg ccatgttcgg gtctttgttc cattttccac actgtctact acatgtgctg    1860
catcagagct tttatgacgc gtgctttttct cagcgctacc tcagatcaca ttttctcacc    1920
tttcagatca caatgtctga atccgaatat gctttgtttg gagatcacaa accttctccc    1980
tatcaaaact atctggatga gaacaagtcc ttaattctga agattgttga aagccagaat    2040
tcaggcaagc ttagcgagtg tgccgagaac caagcaaggc ttcagagaaa tctcatgtac    2100
ttagctgcaa tagctgattc tcaaccccaa ccacccacca tgcctggtca gtaccctccg    2160
agtgggatga tgcagcaggg agcacactac atgcaggctc aacaacagac acagcagatg    2220
tcaccacaac aactaatggc ggcacgctcg tccttttgt acgcacagca gccatactca    2280
gcacttcaac agcagcaagc catgcacagt gcactcgggt cgagttcagg actccacatg    2340
ctgcaaagtg aaggcagcaa tgtgaatgtg ggatcaggca gtggctctgt aggaggaggg    2400
tttcctgact tggtgcgcgg tggtggtggt ggcggtggct cgacagggga gggtttgcac    2460
agtggtggaa gggtatcat gggaagtagc aagcaggaaa ttgggggttc aagtgaaggc    2520
cgaggtgggg aagctcaga gggtggtgaa aacctttacc tcaaaattgc cgacgatgga    2580
aac                                                                  2583
```

<210> SEQ ID NO 21
<211> LENGTH: 1911
<212> TYPE: DNA
<213> ORGANISM: Artificial Sequence
<220> FEATURE:
<223> OTHER INFORMATION: TaGRF4-TaGIF1

<400> SEQUENCE: 21

```
atggcgatgc cgtatgcctc tctttccccg gcaggcgacc gccgctcctc cccggccgcc    60
accgccaccg cctccctcct ccccttctgc cgctcctccc ccttctccgc cggcggcaat    120
ggcggcatgg gggaggaggc gcggatggac gggaggtgga tggcgaggcc ggtgcccttc    180
acggcggcgc agtacgagga gctggagcac caggcgctca tatacaagta cctggtggcc    240
ggcgtgtccg tcccgccgga tctcgtgctc cccatccgcc gcggcatcga gtccctcgcc    300
gcccgcttct accacaaccc cctcgccatc gggtacggat cgtacctggg caagaaggtg    360
gatccggagc cggccggtg ccggcgcacg acggcaagaa agtggcggtg cgccaaggag    420
gccgcctccg actccaagta ttgcgagcgc cacatgcacc gcggccgcaa ccgttcaaga    480
```

```
aagcctgtgg aaacgcagct cgtctcgcac tcccagccgc cggccgcctc cgtcgtgccg    540
cccctcgcca ccggcttcca caaccactcc ctctaccccg ccatcggcgg caccaacggt    600
ggtggaggcg gggggaacaa cggcatgtcc atgcccggca cgttctcctc cgcgctgggg    660
ccgcctcagc agcacatggg caacaatgcc gcctctccct acgcggctct cggcggcgcc    720
ggaacatgca aagatttcag gtataccgca tatggaataa gatctttggc agacgagcag    780
agtcagctca tgacagaagc catgaacacc tccgtggaga acccatggcg cctgccgcca    840
tcttctcaaa cgactacatt cccgctctca agctactctc ctcagcttgg agcaacgagt    900
gacctgggtc agaacaacag cagcaacaac aacagcggcg tcaaggccga gggacagcag    960
cagcagcagc cgctctcctt cccggggtgc ggcgacttcg gcagcggcga ctccgcgaag    1020
caggagaacc agacgctgcg gccgttcttc gacgagtggc cgaagacgag ggactcgtgg    1080
tcggacctga ccgacgacaa ctcgaacgtc gcctccttct cggccaccca gctgtcgatc    1140
tcgatacccg tgcgtcctc cgacttctcc gccgccagct cccagtcgcc aacggcatg    1200 ctgttcgccg gcgaaatgta cgcggccgct gccatgcagc agcaacacct gatgcagatg    1260
aaccagagca tgatggggg ctacgcttcc tctaccactg ccaccactga tctcattcag    1320
cagtacctgg atgagaacaa gcagctgatc ctggccatcc tcgacaacca gaacaacggc    1380
aaggtggagg agtgcgcacg gaaccaagct aagctccagc agaacctcat gtacctcgcc    1440
gccatcgccg acagccagcc tccgcagacg gcatcgctgt ctcagtaccc gtccaacctg    1500
atgatgcagt ccgggccgcg gtacatgcag cagcagtcgg cgcagatgat gtcgccgcag    1560
tcgctgatgg cggcgcggtc gtcgatgatg tacgcgcagc aggccatgtc gccgctccag    1620
cagcagcagc agcagcagca gcaccaggcg gccgcgcacg gccagctggg gatgtcctcc    1680
ggcgcgacca ccgggttcaa cctcctgcac ggtgaggcca gcatgggcgg cggcggcggc    1740
gccactggca acagcatgat gaacgccagc gtcttctcgg actatggccg cggcggcagc    1800
ggcgccaagg aggggtcgac ctcgctgtcg gccgacgctc gcggcgccaa ctctggcgcg    1860
cacagcggcg acggggagta cctcaagggc accgaggagg aagaagcta a              1911
```

<210> SEQ ID NO 22
<211> LENGTH: 1911
<212> TYPE: DNA
<213> ORGANISM: Artificial Sequence
<220> FEATURE:
<223> OTHER INFORMATION: mTaGRF4-TaGIF1

<400> SEQUENCE: 22

```
atggcgatgc gtatgcctc tctttcccg gcaggcgacc gccgctcctc cccggccgcc    60
accgccaccg cctccctcct cccttctgc cgctcctccc ccttctccgc cggcggcaat    120
ggcggcatgg gggaggaggc gcggatggac gggaggtgga tggcgaggcc ggtgcccttc    180
acggcggcgc agtacgagga gctggagcac caggcgctca tatacaagta cctggtggcc    240
ggcgtgtccg tcccgccgga tctcgtgctc cccatccgcc gcggcatcga gtccctcgcc    300
gcccgcttct accacaaccc cctcgccatc gggtacggat cgtacctggg caagaaggtg    360
gatccggagc cggccggtg ccggcgcacg acggcaagaa gtggcggtg cgccaaggag    420 gccgcctccg actccaagta ttgcgagcgc acatgcacc gcggccgcaa ccgttctaga    480
aaaccagtag agacgcagct cgtctcgcac tcccagccgc cggccgcctc cgtcgtgccg    540
cccctcgcca ccggcttcca caaccactcc ctctaccccg ccatcggcgg caccaacggt    600
ggtggaggcg gggggaacaa cggcatgtcc atgcccggca cgttctcctc cgcgctgggg    660
```

```
ccgcctcagc agcacatggg caacaatgcc gcctctccct acgcggctct cggcggcgcc    720
ggaacatgca aagatttcag gtataccgca tatggaataa gatctttggc agacgagcag    780
agtcagctca tgacagaagc catgaacacc tccgtggaga acccatggcg cctgccgcca    840
tcttctcaaa cgactacatt cccgctctca agctactctc ctcagcttgg agcaacgagt    900
gacctgggtc agaacaacag cagcaacaac aacagcggcg tcaaggccga gggacagcag    960
cagcagcagc cgctctcctt cccggggtgc ggcgacttcg cagcggcga ctccgcgaag    1020
caggagaacc agacgctgcg gccgttcttc gacgagtggc cgaagacgag ggactcgtgg    1080
tcggacctga ccgacgacaa ctcgaacgtc gcctccttct cggccaccca gctgtcgatc    1140
tcgataccca tgacgtcctc cgacttctcc gccgccagct cccagtcgcc caacggcatg    1200
ctgttcgccg gcgaaatgta cgcggccgct gccatgcagc agcaacacct gatgcagatg    1260
aaccagagca tgatgggggg ctacgcttcc tctaccactg ccaccactga tctcattcag    1320
cagtacctgg atgagaacaa gcagctgatc ctggccatcc tcgacaacca gaacaacggc    1380
aaggtggagg agtgcgcacg gaaccaagct aagctccagc agaacctcat gtacctcgcc    1440
gccatcgccg acagccagcc tccgcagacg gcatcgctgt ctcagtaccc gtccaacctg    1500
atgatgcagt ccgggccgcg gtacatgcag cagcagtcgg cgcagatgat gtcgccgcag    1560
tcgctgatgg cggcgcggtc gtcgatgatg tacgcgcagc aggccatgtc gccgctccag    1620
cagcagcagc agcagcagca gcaccaggcg gccgcgcacg gccagctggg gatgtcctcc    1680
ggcgcgacca ccgggttcaa cctcctgcac ggtgaggcca gcatgggcgg cggcggcggc    1740
gccactggca acagcatgat gaacgccagc gtcttctcgg actatggccg cggcggcagc    1800
ggcgccaagg aggggtcgac ctcgctgtcg gccgacgctc gcggcgccaa ctctggcgcg    1860
cacagcggcg acgggagta cctcaagggc accgaggagg aaggaagcta a    1911
```

<210> SEQ ID NO 23
<211> LENGTH: 839
<212> TYPE: PRT
<213> ORGANISM: Artificial Sequence
<220> FEATURE:
<223> OTHER INFORMATION: GmGRF5-GmGIF1

<400> SEQUENCE: 23

```
Met Gly Glu Leu Phe Gly Val Gly Lys Arg Arg Asn Ile Ser Ser Ser
1               5                   10                  15

Asn Asn Asn Asn Asn Ser Ser Ser Ser Ser Val Leu Gly Leu Asp Val
            20                  25                  30

Lys Val Gln Gln Ser Pro Glu Ala Leu Phe His Asn Arg Met Met Met
        35                  40                  45

Met Ala His His Asn His His Arg Pro Leu Ser Ser Pro Phe Asp
    50                  55                  60

Asn Asn Gly Asp Gly Asp Gly Pro Thr Thr Tyr Met Ser Phe Thr Asn
65                  70                  75                  80

His Ile Asn Leu Val Ser Gly Ala Ser Val Leu Gly Pro Ala Ile
                85                  90                  95

Asp Ala Gly Cys Gly Ala Ala Pro Pro Ala Pro Val Arg Thr Leu Gln
            100                 105                 110

Pro Phe Asp Ile Ser Ser Tyr Thr Ser Ser Pro Thr Thr Thr Thr Thr
        115                 120                 125

Thr Phe Asn Phe Lys Pro Pro Ser Ala Gly Val Met Ala Ala Ser Leu
    130                 135                 140
```

-continued

```
Gly Phe Pro Phe Thr Ser Ala Gln Trp Arg Glu Leu Glu Arg Gln Ala
145                 150                 155                 160

Met Ile Tyr Lys Tyr Met Met Ala Ser Val Pro Val Pro His Asp Leu
                165                 170                 175

Leu Thr Pro Ser Ser Arg Ser Ser Cys Met Asp Gly Phe Asn Leu
            180                 185                 190

Arg Leu Ala Asn Ser Thr Asp Pro Glu Pro Gly Arg Cys Arg Arg Thr
                195                 200                 205

Asp Gly Lys Lys Trp Arg Cys Ser Arg Asp Val Ala Pro Asn His Lys
            210                 215                 220

Tyr Cys Glu Arg His Met His Arg Gly Arg Pro Arg Ser Arg Lys Pro
225                 230                 235                 240

Val Glu Val Asn Thr Asn Ser Thr Thr Thr Pro Thr Ser Val Asn Asn
                245                 250                 255

Asn Asn His Gln Ile Lys Lys Ala Arg His Glu Cys Asn Asn Asn Pro
            260                 265                 270

Phe Ala Thr Pro Asp Val Thr Ala Ala Ile Ser Asn Pro Thr Ser Arg
                275                 280                 285

Lys Asn Gly Ser Ser Pro His Phe Leu Gly Ser Thr Thr Thr Gln Pro
290                 295                 300

Tyr Leu Asp Ser Ser Leu Ser Leu Asp Asn Phe Gly Leu Lys Ala Ala
305                 310                 315                 320

Ser Phe Asp Ser Val Ala Ser Val Ser Ala Asn Lys Glu Pro Arg Gly
                325                 330                 335

Leu Glu Trp Met Leu Asn Gly Asp Pro Ile Ser Leu Gly Ala Ser Asp
                340                 345                 350

Ser Gln Trp Gln Ser Leu Met His Asn Lys Asp Gly Met Thr Ser Val
            355                 360                 365

Ser Ser Cys Asn Thr Thr Glu Ser Gln Tyr Leu Asn Ser Leu Ala Leu
            370                 375                 380

Tyr Asn Ser Gly Leu Glu Gln Gln Asn Arg Arg His Pro Leu Phe Leu
385                 390                 395                 400

Asn Pro Leu Val Val Pro Met Glu Asn Leu Gln Pro Glu Lys Pro Arg
                405                 410                 415

Gly Phe Ile Asp Ala Trp Ser Asn Ala Glu Ser Asn Ala Asn Thr Asn
                420                 425                 430

Thr Thr Asn Lys Asn Ser Ala Ala Ser Ile Gly Lys Leu Ser Leu Ser
            435                 440                 445

Ser Leu Asp Leu Ser Met Gly Gly Ala Ala Val Asn Glu Asp Val Gly
            450                 455                 460

Asn Val Asn Met Gly Leu Gly Leu Met Glu Pro Asn Gly Lys Thr His
465                 470                 475                 480

Thr Gly Thr Lys Ile Ser Leu Ser Asn Trp Gln Asn Pro Ala Pro Trp
                485                 490                 495

Val Ala Ser Ser Leu Gly Gly Pro Leu Ala Glu Val Leu Arg Ser Ser
            500                 505                 510

Thr Val Thr Ala Thr Thr Thr Asn Glu Ala Thr Ser Asn Thr Pro
            515                 520                 525

Ser Pro Ala Thr Thr His Ala Glu Ser Pro Ser Gly Val Leu Gln
            530                 535                 540

Lys Thr Leu Val Ser Leu Ser Asp Ser Ser Asn Asn Ser Pro Arg
545                 550                 555                 560
```

```
Val Ala Ser Ser Arg Ala Asn Ser Glu Met Ala Leu Leu Arg Phe Gln
            565                 570                 575

Ser Asn Ala Ala Ala Met Phe Gly Ser Leu Phe His Phe Pro His
        580                 585                 590

Cys Leu Leu His Val Leu His Gln Ser Phe Tyr Asp Ala Cys Phe Ser
            595                 600                 605

Gln Arg Tyr Leu Arg Ser His Phe Leu Thr Phe Gln Ile Thr Met Ser
        610                 615                 620

Glu Ser Glu Tyr Ala Leu Phe Gly Asp His Lys Pro Ser Pro Tyr Gln
625                 630                 635                 640

Asn Tyr Leu Asp Glu Asn Lys Ser Leu Ile Leu Lys Ile Val Glu Ser
                645                 650                 655

Gln Asn Ser Gly Lys Leu Ser Glu Cys Ala Glu Asn Gln Ala Arg Leu
            660                 665                 670

Gln Arg Asn Leu Met Tyr Leu Ala Ala Ile Ala Asp Ser Gln Pro Gln
        675                 680                 685

Pro Pro Thr Met Pro Gly Gln Tyr Pro Pro Ser Gly Met Met Gln Gln
        690                 695                 700

Gly Ala His Tyr Met Gln Ala Gln Gln Gln Thr Gln Gln Met Ser Pro
705                 710                 715                 720

Gln Gln Leu Met Ala Ala Arg Ser Ser Leu Leu Tyr Ala Gln Pro
                725                 730                 735

Tyr Ser Ala Leu Gln Gln Gln Gln Ala Met His Ser Ala Leu Gly Ser
                740                 745                 750

Ser Ser Gly Leu His Met Leu Gln Ser Glu Gly Ser Asn Val Asn Val
            755                 760                 765

Gly Ser Gly Ser Gly Ser Val Gly Gly Phe Pro Asp Leu Val Arg
        770                 775                 780

Gly Gly Gly Gly Gly Gly Ser Thr Gly Glu Gly Leu His Ser Gly
785                 790                 795                 800

Gly Arg Gly Ile Met Gly Ser Ser Lys Gln Glu Ile Gly Gly Ser Ser
                805                 810                 815

Glu Gly Arg Gly Gly Gly Ser Ser Glu Gly Gly Glu Asn Leu Tyr Leu
            820                 825                 830

Lys Ile Ala Asp Asp Gly Asn
        835

<210> SEQ ID NO 24
<211> LENGTH: 606
<212> TYPE: PRT
<213> ORGANISM: Artificial Sequence
<220> FEATURE:
<223> OTHER INFORMATION: GmGRF6-GmGIF1

<400> SEQUENCE: 24

Met Met Ser Ala Ser Ala Arg Asn Arg Ser Pro Phe Thr Gln Thr Gln
1               5                   10                  15

Trp Gln Glu Leu Glu His Gln Ala Leu Val Phe Lys Tyr Met Val Thr
                20                  25                  30

Gly Thr Pro Ile Pro Pro Asp Leu Ile Tyr Ser Ile Lys Arg Ser Leu
            35                  40                  45

Asp Thr Ser Ile Ser Ser Arg Leu Phe Pro His His Pro Ile Gly Trp
        50                  55                  60

Gly Cys Phe Glu Met Gly Phe Gly Arg Lys Val Asp Pro Glu Pro Gly
65                  70                  75                  80
```

```
Arg Cys Arg Arg Thr Asp Gly Lys Lys Trp Arg Cys Ser Lys Glu Ala
                85                  90                  95

Tyr Pro Asp Ser Lys Tyr Cys Glu Arg His Met His Arg Gly Arg Asn
            100                 105                 110

Arg Ser Arg Lys Pro Val Glu Val Ser Ser Ala Ile Ser Thr Ala Thr
        115                 120                 125

Asn Thr Ser Gln Thr Ile Pro Ser Ser Tyr Thr Arg Asn Leu Ser Leu
    130                 135                 140

Thr Asn Pro Asn Met Thr Pro Pro Ser Ser Phe Pro Phe Ser Pro Leu
145                 150                 155                 160

Pro Ser Ser Met Pro Ile Glu Ser Gln Pro Phe Ser Gln Ser Tyr Gln
                165                 170                 175

Asn Ser Ser Leu Asn Pro Phe Phe Tyr Ser Gln Ser Thr Ser Ser Arg
            180                 185                 190

Pro Pro Asp Ala Asp Phe Pro Pro Gln Asp Ala Thr Thr His Gln Leu
        195                 200                 205

Phe Met Asp Ser Gly Ser Tyr His Asp Glu Lys Asn Tyr Arg His
    210                 215                 220

Val His Gly Ile Arg Glu Asp Val Asp Glu Arg Ala Phe Phe Pro Glu
225                 230                 235                 240

Ala Ser Gly Ser Ala Arg Ser Tyr Thr Glu Ser Tyr Gln Gln Leu Ser
                245                 250                 255

Met Ser Ser Tyr Lys Ser Tyr Ser Asn Ser Asn Phe Gln Asn Ile Asn
            260                 265                 270

Asp Ala Thr Thr Asn Pro Arg Gln Gln Glu Gln Gln Gln Gln His
        275                 280                 285

Cys Phe Val Leu Gly Thr Asp Phe Lys Ser Thr Arg Pro Thr Lys Glu
290                 295                 300

Lys Glu Ala Glu Thr Ala Thr Gly Gln Arg Pro Leu His Arg Phe Phe
305                 310                 315                 320

Gly Glu Trp Pro Pro Lys Asn Thr Thr Asp Ser Trp Leu Asp Leu Ala
                325                 330                 335

Ser Asn Ser Arg Ile Gln Thr Asp Glu Ala Ala Ala Met Phe Gly
            340                 345                 350

Ser Leu Phe His Phe Pro His Cys Leu Leu His Val Leu His Gln Ser
        355                 360                 365

Phe Tyr Asp Ala Cys Phe Ser Gln Arg Tyr Leu Arg Ser His Phe Leu
    370                 375                 380

Thr Phe Gln Ile Thr Met Ser Glu Ser Glu Tyr Ala Leu Phe Gly Asp
385                 390                 395                 400

His Lys Pro Ser Pro Tyr Gln Asn Tyr Leu Asp Glu Asn Lys Ser Leu
                405                 410                 415

Ile Leu Lys Ile Val Glu Ser Gln Asn Ser Gly Lys Leu Ser Glu Cys
            420                 425                 430

Ala Glu Asn Gln Ala Arg Leu Gln Arg Asn Leu Met Tyr Leu Ala Ala
        435                 440                 445

Ile Ala Asp Ser Gln Pro Gln Pro Thr Met Pro Gly Gln Tyr Pro
    450                 455                 460

Pro Ser Gly Met Met Gln Gly Ala His Tyr Met Gln Ala Gln Gln
465                 470                 475                 480

Gln Thr Gln Gln Met Ser Pro Gln Gln Leu Met Ala Ala Arg Ser Ser
                485                 490                 495

Leu Leu Tyr Ala Gln Gln Pro Tyr Ser Ala Leu Gln Gln Gln Gln Ala
```

```
                          500                 505                 510
Met His Ser Ala Leu Gly Ser Ser Gly Leu His Met Leu Gln Ser
                  515                 520                 525

Glu Gly Ser Asn Val Asn Val Gly Ser Gly Ser Gly Ser Val Gly Gly
              530                 535                 540

Gly Phe Pro Asp Leu Val Arg Gly Gly Gly Gly Gly Gly Ser Thr
545                 550                 555                 560

Gly Glu Gly Leu His Ser Gly Gly Arg Gly Ile Met Gly Ser Ser Lys
                  565                 570                 575

Gln Glu Ile Gly Gly Ser Ser Glu Gly Arg Gly Gly Gly Ser Ser Glu
              580                 585                 590

Gly Gly Glu Asn Leu Tyr Leu Lys Ile Ala Asp Asp Gly Asn
                  595                 600                 605

<210> SEQ ID NO 25
<211> LENGTH: 602
<212> TYPE: PRT
<213> ORGANISM: Artificial Sequence
<220> FEATURE:
<223> OTHER INFORMATION: GmGRF11-GmGIF1

<400> SEQUENCE: 25

Met Asn Asn Ser Ser Gly Gly Gly Gly Arg Gly Thr Leu Met Gly Leu
1                   5                   10                  15

Ser Asn Gly Tyr Cys Gly Arg Ser Pro Phe Thr Val Ser Gln Trp Gln
                20                  25                  30

Glu Leu Glu His Gln Ala Leu Ile Phe Lys Tyr Met Leu Ala Gly Leu
            35                  40                  45

Pro Val Pro Leu Asp Leu Val Phe Pro Ile Gln Asn Ser Phe His Ser
        50                  55                  60

Thr Ile Ser Leu Ser His Ala Phe Phe His His Pro Thr Leu Ser Tyr
65                  70                  75                  80

Cys Ser Phe Tyr Gly Lys Lys Val Asp Pro Glu Pro Gly Arg Cys Arg
                85                  90                  95

Arg Thr Asp Gly Lys Lys Trp Arg Cys Ser Lys Glu Ala Tyr Pro Asp
                100                 105                 110

Ser Lys Tyr Cys Glu Arg His Met His Arg Gly Arg Asn Arg Ser Arg
            115                 120                 125

Lys Pro Val Glu Ser Gln Thr Met Thr His Ser Ser Ser Thr Val Thr
        130                 135                 140

Ser Leu Thr Val Thr Gly Gly Ser Gly Ala Ser Lys Gly Thr Val Asn
145                 150                 155                 160

Phe Gln Asn Leu Ser Thr Asn Thr Phe Gly Asn Leu Gln Gly Thr Asp
                165                 170                 175

Ser Gly Thr Asp His Thr Asn Tyr His Leu Asp Ser Ile Pro Tyr Ala
            180                 185                 190

Ile Pro Ser Lys Glu Tyr Arg Tyr Val Gln Gly Leu Lys Ser Glu Gly
        195                 200                 205

Gly Glu His Cys Phe Phe Ser Glu Ala Ser Gly Ser Asn Lys Val Leu
    210                 215                 220

Gln Met Glu Ser Gln Leu Glu Asn Thr Trp Pro Leu Met Ser Thr Arg
225                 230                 235                 240

Val Ala Ser Phe Ser Thr Ser Lys Ser Ser Asn Asp Ser Leu Leu His
                245                 250                 255

Ser Asp Tyr Pro Arg His Ser Phe Leu Ser Gly Glu Tyr Val Ser Gly
```

```
                    260                 265                 270
Glu His Val Lys Glu Glu Gly Gln Pro Leu Arg Pro Phe Phe Asn Glu
            275                 280                 285

Trp Pro Lys Ser Arg Glu Ser Trp Ser Gly Leu Glu Asp Glu Arg Ser
        290                 295                 300

Asn Gln Thr Ala Phe Ser Thr Thr Gln Leu Ser Ile Ser Ile Pro Met
305                 310                 315                 320

Ser Ser Asn Phe Ser Ala Thr Ser Gln Ser Pro His Gly Glu Asp
                325                 330                 335

Glu Ile Gln Phe Arg Ala Ala Ala Met Phe Gly Ser Leu Phe His
            340                 345                 350

Phe Pro His Cys Leu Leu His Val Leu His Gln Ser Phe Tyr Asp Ala
        355                 360                 365

Cys Phe Ser Gln Arg Tyr Leu Arg Ser His Phe Leu Thr Phe Gln Ile
        370                 375                 380

Thr Met Ser Glu Ser Glu Tyr Ala Leu Phe Gly Asp His Lys Pro Ser
385                 390                 395                 400

Pro Tyr Gln Asn Tyr Leu Asp Glu Asn Lys Ser Leu Ile Leu Lys Ile
                405                 410                 415

Val Glu Ser Gln Asn Ser Gly Lys Leu Ser Glu Cys Ala Glu Asn Gln
            420                 425                 430

Ala Arg Leu Gln Arg Asn Leu Met Tyr Leu Ala Ala Ile Ala Asp Ser
        435                 440                 445

Gln Pro Gln Pro Pro Thr Met Pro Gly Gln Tyr Pro Pro Ser Gly Met
450                 455                 460

Met Gln Gln Gly Ala His Tyr Met Gln Ala Gln Gln Thr Gln Gln
465                 470                 475                 480

Met Ser Pro Gln Gln Leu Met Ala Ala Arg Ser Ser Leu Leu Tyr Ala
                485                 490                 495

Gln Gln Pro Tyr Ser Ala Leu Gln Gln Gln Ala Met His Ser Ala
            500                 505                 510

Leu Gly Ser Ser Ser Gly Leu His Met Leu Gln Ser Glu Gly Ser Asn
        515                 520                 525

Val Asn Val Gly Ser Gly Ser Gly Val Gly Gly Phe Pro Asp
        530                 535                 540

Leu Val Arg Gly Gly Gly Gly Gly Ser Thr Gly Glu Gly Leu
545                 550                 555                 560

His Ser Gly Gly Arg Gly Ile Met Gly Ser Ser Lys Gln Glu Ile Gly
                565                 570                 575

Gly Ser Ser Glu Gly Arg Gly Gly Ser Ser Glu Gly Gly Glu Asn
            580                 585                 590

Leu Tyr Leu Lys Ile Ala Asp Asp Gly Asn
        595                 600

<210> SEQ ID NO 26
<211> LENGTH: 861
<212> TYPE: PRT
<213> ORGANISM: Artificial Sequence
<220> FEATURE:
<223> OTHER INFORMATION: GmGRF18-GmGIF1

<400> SEQUENCE: 26

Met Asp Leu Gly Val Val Gly Leu Glu Gly Val Val Gly Ser Glu Ser
1               5                   10                  15

Gly Cys Val Phe Gly Ser Ser Leu Val Ser Asp Pro Glu Thr Lys His
```

```
              20                  25                  30
Lys Trp Tyr Gly Ser Gly Leu Leu Lys Gln Glu Arg Ser Ala Ile Ala
             35                  40                  45

Thr Glu Asp Asp Glu Trp Arg Ile Ser Lys Val Ala Lys Thr Asp His
 50                  55                  60

Asp Met Ser Ser Ala Ser Lys Ala Met Leu Phe Gln Gln Arg Asn Asn
 65                  70                  75                  80

Ser Leu Leu Arg Ser Asn Asn Ala Thr Leu Phe Ser Asp Gly His His
                 85                  90                  95

Gln Ser Gln Met Leu Ser Phe Ser Ser Pro Lys Ser Asp Ser Leu Leu
                100                 105                 110

Ile Asp Lys Ala Ser Ser Asn Ala Thr Leu Pro Phe Ser Ser His Gln
            115                 120                 125

Leu Ser Ser Tyr Thr Arg Asn Thr Gly Tyr Asn Ser Gly Ser Ile Ser
            130                 135                 140

Met His Gly Ala Leu Ala Ser Val Arg Gly Phe Thr Pro Ser Gln
145                 150                 155                 160

Trp Met Glu Leu Glu His Gln Ala Leu Ile Tyr Lys Tyr Ile Thr Ala
                165                 170                 175

Asn Val Pro Val Pro Thr His Leu Leu Ile Pro Ile Arg Lys Ala Leu
            180                 185                 190

Asp Ser Val Gly Phe Cys Asn Phe Ser Ala Gly Leu Leu Arg Pro Asn
            195                 200                 205

Ser Leu Gly Trp Gly Gly Phe His Leu Gly Phe Ser Asn Asn Thr Asp
            210                 215                 220

Pro Glu Pro Gly Arg Cys Arg Arg Thr Asp Gly Lys Lys Trp Arg Cys
225                 230                 235                 240

Ser Arg Asp Ala Val Val Asp Gln Lys Tyr Cys Glu Arg His Met Asn
                245                 250                 255

Arg Gly Arg His Arg Ser Arg Lys Pro Val Glu Gly Gln Ser Gly His
                260                 265                 270

Ala Leu Thr Thr Thr Thr Ser Asn Thr Pro Asn Ala Ser Ser Asn Ser
            275                 280                 285

Val Val Pro Gly Asn Asn Asn Thr Phe Ala His Asn Asn Val His
            290                 295                 300

His Pro Ile Pro Pro His Ser Pro Val Asn Thr Ile Thr Arg Met
305                 310                 315                 320

Phe Thr Ser Asn Lys Glu Asn Asn Ser Thr Ser Glu Arg Met Gln
                325                 330                 335

Asp Pro Ala Leu Pro Met Leu Pro Thr Leu Glu Leu Lys Pro Lys
            340                 345                 350

Glu Asn Asn Pro Phe Met Ile His Lys His Gln Ile Pro Ser Asp Glu
            355                 360                 365

Tyr Ser Ser Arg Asn Asn Asn Glu Phe Gly Leu Val Thr Ser Asp Ser
            370                 375                 380

Leu Leu Asn Pro Ser Glu Lys Arg Ser Phe Thr Ser Ser Gln Lys Asn
385                 390                 395                 400

Asp Ser Ser Glu Ser Gln Gln Gln His Ser Leu Arg His Phe Ile Asp
                405                 410                 415

Asp Ser Pro Lys Pro Gln Ser Asn His His His Arg Ser Ser Ser Ile
            420                 425                 430

Trp Pro Glu Leu Asp Asn Met Gln Ser Asp Arg Thr Gln Leu Ser Ile
            435                 440                 445
```

```
Ser Ile Pro Ile Ser Ser Ser Asp His Phe Met Ser Phe Thr Thr Ser
    450                 455                 460
Leu Pro Ser Asn Glu Lys Leu Thr Leu Ser Pro Leu Arg Leu Ser Arg
465                 470                 475                 480
Glu Leu Asp Pro Ile Gln Met Gly Leu Gly Val Gly Ser Ala Pro Asn
                485                 490                 495
Glu Ala Asn Thr Arg Gln Ala Asn Trp Ile Pro Ile Thr Trp Glu Ser
                500                 505                 510
Ser Met Gly Gly Pro Leu Gly Glu Val Leu Asn Leu Ser Asn Asn Asn
            515                 520                 525
Asn Ser Asn Ala Ser Asp Gln Cys Gly Lys Asn Asn Asn Thr Ser
    530                 535                 540
Ala Leu Asn Leu Met Lys Asp Gly Trp Asp Asn Asn Pro Pro Ser Gly
545                 550                 555                 560
Ser Ser Pro Thr Gly Val Leu Gln Lys Ser Ala Phe Gly Ser Leu Ser
                565                 570                 575
Asn Ser Ser Ala Gly Ser Ser Pro Arg Gly Ala Glu Asn Asn Lys Glu
                580                 585                 590
Gly Ala Thr Leu Cys Asn Ala Leu Ala Ala Ala Met Phe Gly Ser
    595                 600                 605
Leu Phe His Phe Pro His Cys Leu Leu His Val Leu His Gln Ser Phe
    610                 615                 620
Tyr Asp Ala Cys Phe Ser Gln Arg Tyr Leu Arg Ser His Phe Leu Thr
625                 630                 635                 640
Phe Gln Ile Thr Met Ser Glu Ser Glu Tyr Ala Leu Phe Gly Asp His
                645                 650                 655
Lys Pro Ser Pro Tyr Gln Asn Tyr Leu Asp Glu Asn Lys Ser Leu Ile
                660                 665                 670
Leu Lys Ile Val Glu Ser Gln Asn Ser Gly Lys Leu Ser Glu Cys Ala
    675                 680                 685
Glu Asn Gln Ala Arg Leu Gln Arg Asn Leu Met Tyr Leu Ala Ala Ile
    690                 695                 700
Ala Asp Ser Gln Pro Gln Pro Pro Thr Met Pro Gly Gln Tyr Pro Pro
705                 710                 715                 720
Ser Gly Met Met Gln Gln Gly Ala His Tyr Met Gln Ala Gln Gln
                725                 730                 735
Thr Gln Gln Met Ser Pro Gln Gln Leu Met Ala Ala Arg Ser Ser Leu
                740                 745                 750
Leu Tyr Ala Gln Gln Pro Tyr Ser Ala Leu Gln Gln Gln Ala Met
    755                 760                 765
His Ser Ala Leu Gly Ser Ser Ser Gly Leu His Met Leu Gln Ser Glu
    770                 775                 780
Gly Ser Asn Val Asn Val Gly Ser Gly Ser Val Gly Gly
785                 790                 795                 800
Phe Pro Asp Leu Val Arg Gly Gly Gly Gly Gly Ser Thr Gly
                805                 810                 815
Glu Gly Leu His Ser Gly Gly Arg Gly Ile Met Gly Ser Ser Lys Gln
                820                 825                 830
Glu Ile Gly Gly Ser Ser Glu Gly Arg Gly Gly Ser Ser Glu Gly
    835                 840                 845
Gly Glu Asn Leu Tyr Leu Lys Ile Ala Asp Asp Gly Asn
    850                 855                 860
```

<210> SEQ ID NO 27
<211> LENGTH: 636
<212> TYPE: PRT
<213> ORGANISM: Artificial Sequence
<220> FEATURE:
<223> OTHER INFORMATION: TaGRF4-TaGIF1

<400> SEQUENCE: 27

```
Met Ala Met Pro Tyr Ala Ser Leu Ser Pro Ala Gly Asp Arg Arg Ser
1               5                   10                  15

Ser Pro Ala Ala Thr Ala Thr Ala Ser Leu Leu Pro Phe Cys Arg Ser
            20                  25                  30

Ser Pro Phe Ser Ala Gly Gly Asn Gly Gly Met Gly Glu Glu Ala Arg
        35                  40                  45

Met Asp Gly Arg Trp Met Ala Arg Pro Val Pro Phe Thr Ala Ala Gln
    50                  55                  60

Tyr Glu Glu Leu Glu His Gln Ala Leu Ile Tyr Lys Tyr Leu Val Ala
65                  70                  75                  80

Gly Val Ser Val Pro Pro Asp Leu Val Leu Pro Ile Arg Arg Gly Ile
                85                  90                  95

Glu Ser Leu Ala Ala Arg Phe Tyr His Asn Pro Leu Ala Ile Gly Tyr
            100                 105                 110

Gly Ser Tyr Leu Gly Lys Lys Val Asp Pro Glu Pro Gly Arg Cys Arg
        115                 120                 125

Arg Thr Asp Gly Lys Lys Trp Arg Cys Ala Lys Glu Ala Ala Ser Asp
    130                 135                 140

Ser Lys Tyr Cys Glu Arg His Met His Arg Gly Arg Asn Arg Ser Arg
145                 150                 155                 160

Lys Pro Val Glu Thr Gln Leu Val Ser His Ser Gln Pro Pro Ala Ala
                165                 170                 175

Ser Val Val Pro Pro Leu Ala Thr Gly Phe His Asn His Ser Leu Tyr
            180                 185                 190

Pro Ala Ile Gly Gly Thr Asn Gly Gly Gly Gly Gly Asn Asn Gly
        195                 200                 205

Met Ser Met Pro Gly Thr Phe Ser Ser Ala Leu Gly Pro Pro Gln Gln
    210                 215                 220

His Met Gly Asn Asn Ala Ala Ser Pro Tyr Ala Ala Leu Gly Gly Ala
225                 230                 235                 240

Gly Thr Cys Lys Asp Phe Arg Tyr Thr Ala Tyr Gly Ile Arg Ser Leu
                245                 250                 255

Ala Asp Glu Gln Ser Gln Leu Met Thr Glu Ala Met Asn Thr Ser Val
            260                 265                 270

Glu Asn Pro Trp Arg Leu Pro Pro Ser Ser Gln Thr Thr Thr Phe Pro
        275                 280                 285

Leu Ser Ser Tyr Ser Pro Gln Leu Gly Ala Thr Ser Asp Leu Gly Gln
    290                 295                 300

Asn Asn Ser Ser Asn Asn Ser Gly Val Lys Ala Glu Gly Gln Gln
305                 310                 315                 320

Gln Gln Gln Pro Leu Ser Phe Pro Gly Cys Gly Asp Phe Gly Ser Gly
                325                 330                 335

Asp Ser Ala Lys Gln Glu Asn Gln Thr Leu Arg Pro Phe Phe Asp Glu
            340                 345                 350

Trp Pro Lys Thr Arg Asp Ser Trp Ser Asp Leu Thr Asp Asn Ser
        355                 360                 365
```

```
Asn Val Ala Ser Phe Ser Ala Thr Gln Leu Ser Ile Ser Ile Pro Met
    370                 375                 380

Thr Ser Ser Asp Phe Ser Ala Ala Ser Ser Gln Ser Pro Asn Gly Met
385                 390                 395                 400

Leu Phe Ala Gly Glu Met Tyr Ala Ala Ala Met Gln Gln Gln His
            405                 410                 415

Leu Met Gln Met Asn Gln Ser Met Met Gly Gly Tyr Ala Ser Ser Thr
            420                 425                 430

Thr Ala Thr Thr Asp Leu Ile Gln Gln Tyr Leu Asp Glu Asn Lys Gln
            435                 440                 445

Leu Ile Leu Ala Ile Leu Asp Asn Gln Asn Asn Gly Lys Val Glu Glu
450                 455                 460

Cys Ala Arg Asn Gln Ala Lys Leu Gln Gln Asn Leu Met Tyr Leu Ala
465                 470                 475                 480

Ala Ile Ala Asp Ser Gln Pro Pro Gln Thr Ala Ser Leu Ser Gln Tyr
                485                 490                 495

Pro Ser Asn Leu Met Met Gln Ser Gly Pro Arg Tyr Met Gln Gln Gln
                500                 505                 510

Ser Ala Gln Met Met Ser Pro Gln Ser Leu Met Ala Ala Arg Ser Ser
                515                 520                 525

Met Met Tyr Ala Gln Gln Ala Met Ser Pro Leu Gln Gln Gln Gln Gln
            530                 535                 540

Gln Gln Gln His Gln Ala Ala His Gly Gln Leu Gly Met Ser Ser
545                 550                 555                 560

Gly Ala Thr Thr Gly Phe Asn Leu Leu His Gly Glu Ala Ser Met Gly
                565                 570                 575

Gly Gly Gly Gly Ala Thr Gly Asn Ser Met Met Asn Ala Ser Val Phe
                580                 585                 590

Ser Asp Tyr Gly Arg Gly Gly Ser Gly Ala Lys Glu Gly Ser Thr Ser
                595                 600                 605

Leu Ser Ala Asp Ala Arg Gly Ala Asn Ser Gly Ala His Ser Gly Asp
            610                 615                 620

Gly Glu Tyr Leu Lys Gly Thr Glu Glu Glu Gly Ser
625                 630                 635

<210> SEQ ID NO 28
<211> LENGTH: 636
<212> TYPE: PRT
<213> ORGANISM: Artificial Sequence
<220> FEATURE:
<223> OTHER INFORMATION: mTaGRF4-TaGIF1

<400> SEQUENCE: 28

Met Ala Met Pro Tyr Ala Ser Leu Ser Pro Ala Gly Asp Arg Arg Ser
1               5                   10                  15

Ser Pro Ala Ala Thr Ala Thr Ala Ser Leu Leu Pro Phe Cys Arg Ser
                20                  25                  30

Ser Pro Phe Ser Ala Gly Gly Asn Gly Gly Met Gly Glu Glu Ala Arg
            35                  40                  45

Met Asp Gly Arg Trp Met Ala Arg Pro Val Pro Phe Thr Ala Ala Gln
50                  55                  60

Tyr Glu Glu Leu Glu His Gln Ala Leu Ile Tyr Lys Tyr Leu Val Ala
65                  70                  75                  80

Gly Val Ser Val Pro Pro Asp Leu Val Leu Pro Ile Arg Arg Gly Ile
                85                  90                  95
```

```
Glu Ser Leu Ala Ala Arg Phe Tyr His Asn Pro Leu Ala Ile Gly Tyr
                100                 105                 110

Gly Ser Tyr Leu Gly Lys Lys Val Asp Pro Glu Pro Gly Arg Cys Arg
            115                 120                 125

Arg Thr Asp Gly Lys Lys Trp Arg Cys Ala Lys Glu Ala Ala Ser Asp
        130                 135                 140

Ser Lys Tyr Cys Glu Arg His Met His Arg Gly Arg Asn Arg Ser Arg
145                 150                 155                 160

Lys Pro Val Glu Thr Gln Leu Val Ser His Ser Gln Pro Pro Ala Ala
                165                 170                 175

Ser Val Val Pro Pro Leu Ala Thr Gly Phe His Asn His Ser Leu Tyr
            180                 185                 190

Pro Ala Ile Gly Gly Thr Asn Gly Gly Gly Gly Gly Asn Asn Gly
            195                 200                 205

Met Ser Met Pro Gly Thr Phe Ser Ser Ala Leu Gly Pro Pro Gln Gln
210                 215                 220

His Met Gly Asn Asn Ala Ala Ser Pro Tyr Ala Ala Leu Gly Gly Ala
225                 230                 235                 240

Gly Thr Cys Lys Asp Phe Arg Tyr Thr Ala Tyr Gly Ile Arg Ser Leu
            245                 250                 255

Ala Asp Glu Gln Ser Gln Leu Met Thr Glu Ala Met Asn Thr Ser Val
            260                 265                 270

Glu Asn Pro Trp Arg Leu Pro Ser Ser Gln Thr Thr Phe Pro
            275                 280                 285

Leu Ser Ser Tyr Ser Pro Gln Leu Gly Ala Thr Ser Asp Leu Gly Gln
            290                 295                 300

Asn Asn Ser Ser Asn Asn Asn Ser Gly Val Lys Ala Glu Gly Gln Gln
305                 310                 315                 320

Gln Gln Gln Pro Leu Ser Phe Pro Gly Cys Gly Asp Phe Gly Ser Gly
                325                 330                 335

Asp Ser Ala Lys Gln Glu Asn Gln Thr Leu Arg Pro Phe Phe Asp Glu
            340                 345                 350

Trp Pro Lys Thr Arg Asp Ser Trp Ser Asp Leu Thr Asp Asp Asn Ser
            355                 360                 365

Asn Val Ala Ser Phe Ser Ala Thr Gln Leu Ser Ile Ser Ile Pro Met
370                 375                 380

Thr Ser Ser Asp Phe Ser Ala Ala Ser Ser Gln Ser Pro Asn Gly Met
385                 390                 395                 400

Leu Phe Ala Gly Glu Met Tyr Ala Ala Ala Met Gln Gln Gln His
            405                 410                 415

Leu Met Gln Met Asn Gln Ser Met Met Gly Gly Tyr Ala Ser Ser Thr
            420                 425                 430

Thr Ala Thr Thr Asp Leu Ile Gln Gln Tyr Leu Asp Glu Asn Lys Gln
            435                 440                 445

Leu Ile Leu Ala Ile Leu Asp Asn Gln Asn Gly Lys Val Glu Glu
            450                 455                 460

Cys Ala Arg Asn Gln Ala Lys Leu Gln Gln Asn Leu Met Tyr Leu Ala
465                 470                 475                 480

Ala Ile Ala Asp Ser Gln Pro Pro Gln Thr Ala Ser Leu Ser Gln Tyr
            485                 490                 495

Pro Ser Asn Leu Met Met Gln Ser Gly Pro Arg Tyr Met Gln Gln Gln
            500                 505                 510

Ser Ala Gln Met Met Ser Pro Gln Ser Leu Met Ala Ala Arg Ser Ser
```

```
                    515                 520                 525
Met Met Tyr Ala Gln Gln Ala Met Ser Pro Leu Gln Gln Gln Gln
                530                 535                 540

Gln Gln Gln His Gln Ala Ala His Gly Gln Leu Gly Met Ser Ser
545                 550                 555                 560

Gly Ala Thr Thr Gly Phe Asn Leu Leu His Gly Glu Ala Ser Met Gly
                    565                 570                 575

Gly Gly Gly Gly Ala Thr Gly Asn Ser Met Met Asn Ala Ser Val Phe
                580                 585                 590

Ser Asp Tyr Gly Arg Gly Gly Ser Gly Ala Lys Glu Gly Ser Thr Ser
                595                 600                 605

Leu Ser Ala Asp Ala Arg Gly Ala Asn Ser Gly Ala His Ser Gly Asp
610                 615                 620

Gly Glu Tyr Leu Lys Gly Thr Glu Glu Glu Gly Ser
625                 630                 635

<210> SEQ ID NO 29
<211> LENGTH: 22
<212> TYPE: DNA
<213> ORGANISM: Artificial Sequence
<220> FEATURE:
<223> OTHER INFORMATION: miRNA site

<400> SEQUENCE: 29
ccgttcaaga aagcctgtgg aa                                              22

<210> SEQ ID NO 30
<211> LENGTH: 22
<212> TYPE: DNA
<213> ORGANISM: Artificial Sequence
<220> FEATURE:
<223> OTHER INFORMATION: miRNA site

<400> SEQUENCE: 30
ccgttctaga aaaccagtag ag                                              22

<210> SEQ ID NO 31
<211> LENGTH: 71
<212> TYPE: DNA
<213> ORGANISM: Artificial Sequence
<220> FEATURE:
<223> OTHER INFORMATION: WT

<400> SEQUENCE: 31
tccttcctca acccttttcc ctcattgcat ggccaatcta ttgggttctc caaggttgcc    60
ttctcactgg t                                                         71

<210> SEQ ID NO 32
<211> LENGTH: 61
<212> TYPE: DNA
<213> ORGANISM: Artificial Sequence
<220> FEATURE:
<223> OTHER INFORMATION: mutant sequence

<400> SEQUENCE: 32
tccttcctca acccttttcc ctcattgcat ggccaatctc caaggttgcc ttctcactgg    60
t                                                                    61

<210> SEQ ID NO 33
<211> LENGTH: 68
<212> TYPE: DNA
```

```
<213> ORGANISM: Artificial Sequence
<220> FEATURE:
<223> OTHER INFORMATION: mutant sequence

<400> SEQUENCE: 33
tccttcctca acccttttcc ctcattgcat ggccaatctt ggttctccaa ggttgccttc      60
tcactggt                                                              68

<210> SEQ ID NO 34
<211> LENGTH: 58
<212> TYPE: DNA
<213> ORGANISM: Artificial Sequence
<220> FEATURE:
<223> OTHER INFORMATION: mutant sequence

<400> SEQUENCE: 34
tccttcctca acccttttcc ctcattgcat ggccctccaa ggttgccttc tcactggt       58

<210> SEQ ID NO 35
<211> LENGTH: 69
<212> TYPE: DNA
<213> ORGANISM: Artificial Sequence
<220> FEATURE:
<223> OTHER INFORMATION: mutant sequence

<400> SEQUENCE: 35
tccttcctca acccttttcc ctcattgcat ggcctctatt gggttctcca aggttgcctt     60
ctcactggt                                                             69

<210> SEQ ID NO 36
<211> LENGTH: 70
<212> TYPE: DNA
<213> ORGANISM: Artificial Sequence
<220> FEATURE:
<223> OTHER INFORMATION: mutant sequence

<400> SEQUENCE: 36
tccttcctca acccttttcc ctcattgcat ggccaactat tgggttctcc aaggttgcct     60
tctcactggt                                                            70

<210> SEQ ID NO 37
<211> LENGTH: 69
<212> TYPE: DNA
<213> ORGANISM: Artificial Sequence
<220> FEATURE:
<223> OTHER INFORMATION: mutant sequence

<400> SEQUENCE: 37
tccttcctca acccttttcc ctcattgcat ggccaatcta ttgttctcca aggttgcctt     60
ctcactggt                                                             69

<210> SEQ ID NO 38
<211> LENGTH: 60
<212> TYPE: DNA
<213> ORGANISM: Artificial Sequence
<220> FEATURE:
<223> OTHER INFORMATION: mutant sequence

<400> SEQUENCE: 38
tccttcctca acccttttcc ctcattgcat ggccaactcc aaggttgcct tctcactggt     60

<210> SEQ ID NO 39
<211> LENGTH: 69
```

```
<212> TYPE: DNA
<213> ORGANISM: Artificial Sequence
<220> FEATURE:
<223> OTHER INFORMATION: mutant sequence

<400> SEQUENCE: 39
tccttcctca acccttttcc ctcattgcat ggccaatcta ttggtctcca aggttgcctt    60
ctcactggt                                                            69

<210> SEQ ID NO 40
<211> LENGTH: 67
<212> TYPE: DNA
<213> ORGANISM: Artificial Sequence
<220> FEATURE:
<223> OTHER INFORMATION: mutant sequence

<400> SEQUENCE: 40
tccttcctca acccttttcc ctcattgcat ggccaatcta ttgctccaag gttgccttct    60
cactggt                                                              67

<210> SEQ ID NO 41
<211> LENGTH: 68
<212> TYPE: DNA
<213> ORGANISM: Artificial Sequence
<220> FEATURE:
<223> OTHER INFORMATION: mutant sequence

<400> SEQUENCE: 41
tccttcctca acccttttcc ctcattgcat ggccaatcta ttggctccaa ggttgccttc    60
tcactggt                                                             68

<210> SEQ ID NO 42
<211> LENGTH: 63
<212> TYPE: DNA
<213> ORGANISM: Artificial Sequence
<220> FEATURE:
<223> OTHER INFORMATION: mutant sequence

<400> SEQUENCE: 42
tccttcctca acccttttcc ctcattgcat ggccaatcta ttgaaggttg ccttctcact    60
ggt                                                                  63

<210> SEQ ID NO 43
<211> LENGTH: 67
<212> TYPE: DNA
<213> ORGANISM: Artificial Sequence
<220> FEATURE:
<223> OTHER INFORMATION: mutant sequence

<400> SEQUENCE: 43
tccttcctca acccttttcc ctcattgcat ggccaatcta ttggtccaag gttgccttct    60
cactggt                                                              67

<210> SEQ ID NO 44
<211> LENGTH: 64
<212> TYPE: DNA
<213> ORGANISM: Artificial Sequence
<220> FEATURE:
<223> OTHER INFORMATION: mutant sequence

<400> SEQUENCE: 44
tccttcctca acccttttcc ctcattgcat ggccaatctt ctccaaggtt gccttctcac    60
```

```
tggt                                                                  64

<210> SEQ ID NO 45
<211> LENGTH: 62
<212> TYPE: DNA
<213> ORGANISM: Artificial Sequence
<220> FEATURE:
<223> OTHER INFORMATION: mutant sequence

<400> SEQUENCE: 45
tccttcctca acccttttcc ctcattgcat ggccaattct ccaaggttgc cttctcactg     60
gt                                                                    62

<210> SEQ ID NO 46
<211> LENGTH: 61
<212> TYPE: DNA
<213> ORGANISM: Artificial Sequence
<220> FEATURE:
<223> OTHER INFORMATION: mutant sequence

<400> SEQUENCE: 46
tccttcctca acccttttcc ctcattgcat ggccaatctc caaggttgcc ttctcactgg     60
t                                                                     61

<210> SEQ ID NO 47
<211> LENGTH: 66
<212> TYPE: DNA
<213> ORGANISM: Artificial Sequence
<220> FEATURE:
<223> OTHER INFORMATION: mutant sequence

<400> SEQUENCE: 47
tccttcctca acccttttcc ctcattgcat ggccaatcta ttctccaagg ttgccttctc     60
actggt                                                                66

<210> SEQ ID NO 48
<211> LENGTH: 69
<212> TYPE: DNA
<213> ORGANISM: Artificial Sequence
<220> FEATURE:
<223> OTHER INFORMATION: mutant sequence

<400> SEQUENCE: 48
tccttcctca acccttttcc ctcattgcat ggccaatcta ttggtctcca aggttgcctt     60
ctcactggt                                                             69

<210> SEQ ID NO 49
<211> LENGTH: 65
<212> TYPE: DNA
<213> ORGANISM: Artificial Sequence
<220> FEATURE:
<223> OTHER INFORMATION: mutant sequence

<400> SEQUENCE: 49
tccttcctca acccttttcc ctcattgcat ggccaatcta tttccaaggt tgccttctca     60
ctggt                                                                 65

<210> SEQ ID NO 50
<211> LENGTH: 69
<212> TYPE: DNA
<213> ORGANISM: Artificial Sequence
<220> FEATURE:
<223> OTHER INFORMATION: mutant sequence
```

<400> SEQUENCE: 50
tccttcctca acccttttcc ctcattgcat ggccaatcta ttggtctcca aggttgcctt    60
ctcactggt    69

<210> SEQ ID NO 51
<211> LENGTH: 67
<212> TYPE: DNA
<213> ORGANISM: Artificial Sequence
<220> FEATURE:
<223> OTHER INFORMATION: mutant sequence

<400> SEQUENCE: 51
tccttcctca acccttttcc ctcattgcat ggccaatcta ttgctccaag gttgccttct    60
cactggt    67

<210> SEQ ID NO 52
<211> LENGTH: 67
<212> TYPE: DNA
<213> ORGANISM: Artificial Sequence
<220> FEATURE:
<223> OTHER INFORMATION: mutant sequence

<400> SEQUENCE: 52
tccttcctca acccttttcc ctcattgcat ggccaatcta tttctccaag gttgccttct    60
cactggt    67

<210> SEQ ID NO 53
<211> LENGTH: 67
<212> TYPE: DNA
<213> ORGANISM: Artificial Sequence
<220> FEATURE:
<223> OTHER INFORMATION: mutant sequence

<400> SEQUENCE: 53
tccttcctca acccttttcc ctcattgcat ggccaatcta tttctccaag gttgccttct    60
cactggt    67

<210> SEQ ID NO 54
<211> LENGTH: 68
<212> TYPE: DNA
<213> ORGANISM: Artificial Sequence
<220> FEATURE:
<223> OTHER INFORMATION: mutant sequence

<400> SEQUENCE: 54
tccttcctca acccttttcc ctcattgcat ggccaatcta ttggctccaa ggttgccttc    60
tcactggt    68

<210> SEQ ID NO 55
<211> LENGTH: 54
<212> TYPE: DNA
<213> ORGANISM: Artificial Sequence
<220> FEATURE:
<223> OTHER INFORMATION: mutant sequence

<400> SEQUENCE: 55
tccttcctca acccttttcc ctcatttttc atccaaggtt gccttctcac tggt    54

<210> SEQ ID NO 56
<211> LENGTH: 68
<212> TYPE: DNA

<213> ORGANISM: Artificial Sequence
<220> FEATURE:
<223> OTHER INFORMATION: mutant sequence

<400> SEQUENCE: 56
tccttcctca acccttttcc ctcattgcat ggccaatcta ttggctccaa ggttgccttc    60
tcactggt    68

<210> SEQ ID NO 57
<211> LENGTH: 66
<212> TYPE: DNA
<213> ORGANISM: Artificial Sequence
<220> FEATURE:
<223> OTHER INFORMATION: mutant sequence

<400> SEQUENCE: 57
tccttcctca acccttttcc ctcattgcat ggccaatcta ttctccaagg ttgccttctc    60
actggt    66

<210> SEQ ID NO 58
<211> LENGTH: 60
<212> TYPE: DNA
<213> ORGANISM: Artificial Sequence
<220> FEATURE:
<223> OTHER INFORMATION: mutant sequence

<400> SEQUENCE: 58
tccttcctca acccttttcc ctcattgcat ggccatctcc aaggttgcct tctcactggt    60

<210> SEQ ID NO 59
<211> LENGTH: 69
<212> TYPE: DNA
<213> ORGANISM: Artificial Sequence
<220> FEATURE:
<223> OTHER INFORMATION: mutant sequence

<400> SEQUENCE: 59
tccttcctca acccttttcc ctcattgcat ggccaatcta ttggtctcca aggttgcctt    60
ctcactggt    69

<210> SEQ ID NO 60
<211> LENGTH: 54
<212> TYPE: DNA
<213> ORGANISM: Artificial Sequence
<220> FEATURE:
<223> OTHER INFORMATION: mutant sequence

<400> SEQUENCE: 60
tccttcctca acccttttcc ctcattgcat ctccaaggtt gccttctcac tggt    54

<210> SEQ ID NO 61
<211> LENGTH: 65
<212> TYPE: DNA
<213> ORGANISM: Artificial Sequence
<220> FEATURE:
<223> OTHER INFORMATION: mutant sequence

<400> SEQUENCE: 61
tccttcctca acccttttcc ctcattgcat ggccaatcta tctccaaggt tgccttctca    60
ctggt    65

<210> SEQ ID NO 62
<211> LENGTH: 23

```
<212> TYPE: DNA
<213> ORGANISM: Artificial Sequence
<220> FEATURE:
<223> OTHER INFORMATION: target

<400> SEQUENCE: 62
gtatccgcaa cagcactgaa agg                                           23

<210> SEQ ID NO 63
<211> LENGTH: 24
<212> TYPE: DNA
<213> ORGANISM: Artificial Sequence
<220> FEATURE:
<223> OTHER INFORMATION: WT

<400> SEQUENCE: 63
tccgcaacag cactgaaagg agaa                                          24

<210> SEQ ID NO 64
<211> LENGTH: 24
<212> TYPE: DNA
<213> ORGANISM: Artificial Sequence
<220> FEATURE:
<223> OTHER INFORMATION: Fa-6

<400> SEQUENCE: 64
tccgcaacaa cactgaaagg agaa                                          24

<210> SEQ ID NO 65
<211> LENGTH: 24
<212> TYPE: DNA
<213> ORGANISM: Artificial Sequence
<220> FEATURE:
<223> OTHER INFORMATION: Fa-21

<400> SEQUENCE: 65
tccccaaggc ccctgaaagg agaa                                          24

<210> SEQ ID NO 66
<211> LENGTH: 25
<212> TYPE: DNA
<213> ORGANISM: Artificial Sequence
<220> FEATURE:
<223> OTHER INFORMATION: Fa-34

<400> SEQUENCE: 66
tccccaacca cccttgaaag gagaa                                         25

<210> SEQ ID NO 67
<211> LENGTH: 23
<212> TYPE: DNA
<213> ORGANISM: Artificial Sequence
<220> FEATURE:
<223> OTHER INFORMATION: TaALS target

<400> SEQUENCE: 67
caggtccccc gccgcatgat cgg                                           23
```

```
<210> SEQ ID NO 68
<211> LENGTH: 23
<212> TYPE: DNA
<213> ORGANISM: Artificial Sequence
<220> FEATURE:
<223> OTHER INFORMATION: GmFAD2 target

<400> SEQUENCE: 68
cattgcatgg ccaatctatt ggg                                              23
```